(12) United States Patent
Simpson et al.

(10) Patent No.: US 10,667,733 B2
(45) Date of Patent: Jun. 2, 2020

(54) TRANSCUTANEOUS ANALYTE SENSOR

(71) Applicant: DexCom, Inc., San Diego, CA (US)

(72) Inventors: Peter C. Simpson, Cardiff, CA (US);
Robert J. Boock, Carlsbad, CA (US);
Sebastian Böhm, San Diego, CA (US);
James H. Brauker, Addison, MI (US);
Paul V. Neale, San Diego, CA (US)

(73) Assignee: DexCom, Inc., San Diego, CA (US)

( * ) Notice: Subject to any disclaimer, the term of this patent is extended or adjusted under 35 U.S.C. 154(b) by 0 days.

(21) Appl. No.: 14/968,643

(22) Filed: Dec. 14, 2015

(65) Prior Publication Data
US 2016/0095542 A1 Apr. 7, 2016

Related U.S. Application Data

(63) Continuation of application No. 12/893,850, filed on Sep. 29, 2010, now Pat. No. 9,357,951.
(Continued)

(51) Int. Cl.
*A61B 5/1486* (2006.01)
*A61B 5/1468* (2006.01)
(Continued)

(52) U.S. Cl.
CPC ........ *A61B 5/14865* (2013.01); *A61B 5/1468* (2013.01); *A61B 5/1473* (2013.01);
(Continued)

(58) Field of Classification Search
CPC .... A61B 2560/0443; A61B 2562/0209; A61B 2562/04; A61B 5/14503; A61B 5/14532;
(Continued)

(56) References Cited

U.S. PATENT DOCUMENTS 4,671,288 A  6/1987 Gough
4,777,953 A  10/1988 Ash et al.
(Continued)

FOREIGN PATENT DOCUMENTS

EP  0 098 592  1/1984
EP  0 107 634  5/1984
(Continued)

OTHER PUBLICATIONS

US 7,530,950 B2, 05/2009, Brister et al. (withdrawn)
(Continued)

*Primary Examiner* — Navin Natnithithadha
(74) *Attorney, Agent, or Firm* — Knobbe, Martens, Olson & Bear, LLP

(57) ABSTRACT

A transcutaneous sensor device configured for continuously measuring analyte concentrations in a host is provided. In some embodiments, the transcutaneous sensor device 100 comprises an in vivo portion 160 configured for insertion under the skin 180 of the host and an ex vivo portion 170 configured to remain above the surface of the skin 180 of the host after sensor insertion of the in vivo portion. The in vivo portion may comprise a tissue piercing element 110 configured for piercing the skin 180 of the host and a sensor body 120 comprising a material or support member 130 that provides sufficient column strength to allow the sensor body to be pushable in a host tissue without substantial buckling. The ex vivo portion 170 may be configured to comprise (or operably connect to) a sensor electronics unit and may comprise a mounting unit 150. Also described here are various configurations of the sensor body and the tissue piercing element that may be used to protect the membrane of the sensor body.

9 Claims, 28 Drawing Sheets

Related U.S. Application Data

(60) Provisional application No. 61/247,463, filed on Sep. 30, 2009.

(51) Int. Cl.
    *A61B 5/1473*       (2006.01)
    *A61B 5/145*        (2006.01)
    *A61B 5/00*         (2006.01)

(52) U.S. Cl.
    CPC ........ *A61B 5/1486* (2013.01); *A61B 5/14503* (2013.01); *A61B 5/14532* (2013.01); *A61B 5/14546* (2013.01); *A61B 5/6843* (2013.01); *A61B 5/6848* (2013.01); *A61B 5/6849* (2013.01); *A61B 2560/0443* (2013.01); *A61B 2562/04* (2013.01)

(58) Field of Classification Search
CPC . A61B 5/14546; A61B 5/1468; A61B 5/1473; A61B 5/1486; A61B 5/14865; A61B 5/6843; A61B 5/6848; A61B 5/6849; A61B 2560/063; A61B 5/0002; A61B 5/1451; A61B 5/14542
USPC .......................................... 600/309, 345–366
See application file for complete search history.

(56) References Cited

U.S. PATENT DOCUMENTS

| | | | |
|---|---|---|---|
| 4,832,034 A | 5/1989 | Pizziconi et al. | |
| 4,854,322 A | 8/1989 | Ash et al. | |
| 4,953,552 A | 9/1990 | DeMarzo | |
| 5,050,612 A | 9/1991 | Matsumura | |
| 5,109,850 A | 5/1992 | Blanco et al. | |
| 5,165,407 A | 11/1992 | Wilson et al. | |
| 5,269,891 A | 12/1993 | Colin | |
| 5,390,671 A * | 2/1995 | Lord ................. | A61B 5/14865 204/403.01 |
| 5,582,184 A | 12/1996 | Ericson et al. | |
| 5,746,217 A * | 5/1998 | Erickson ............ | A61B 5/14514 600/310 |
| 5,800,420 A | 9/1998 | Gross et al. | |
| 5,807,375 A | 9/1998 | Gross et al. | |
| 5,820,570 A | 10/1998 | Erickson et al. | |
| 5,820,622 A | 10/1998 | Gross et al. | |
| 5,931,814 A * | 8/1999 | Alex ................. | A61M 5/14248 604/131 |
| 6,071,294 A * | 6/2000 | Simons .............. | A61B 5/14532 606/181 |
| 6,091,975 A | 7/2000 | Daddona et al. | |
| 6,103,033 A | 8/2000 | Say et al. | |
| 6,132,449 A * | 10/2000 | Lum ................. | A61B 5/150022 606/181 |
| 6,186,982 B1 * | 2/2001 | Gross ................ | A61M 5/14248 604/132 |
| 6,248,067 B1 | 6/2001 | Causey, III et al. | |
| 6,254,586 B1 | 7/2001 | Mann et al. | |
| 6,256,522 B1 | 7/2001 | Schultz | |
| 6,275,717 B1 | 8/2001 | Gross et al. | |
| 6,442,413 B1 | 8/2002 | Silver | |
| 6,454,710 B1 | 9/2002 | Ballerstadt et al. | |
| 6,484,045 B1 | 11/2002 | Holker et al. | |
| 6,537,242 B1 * | 3/2003 | Palmer .............. | A61M 37/0015 600/309 |
| 6,579,690 B1 | 6/2003 | Bonnecaze et al. | |
| 6,589,229 B1 | 7/2003 | Connelly et al. | |
| 6,770,030 B1 | 8/2004 | Schaupp et al. | |
| 6,809,653 B1 | 10/2004 | Mann et al. | |
| 6,895,265 B2 | 5/2005 | Silver | |
| 6,936,006 B2 | 8/2005 | Sabra | |
| 7,003,336 B2 | 2/2006 | Holker et al. | |
| 7,033,322 B2 | 4/2006 | Silver | |
| 7,060,059 B2 | 6/2006 | Keith et al. | |
| 7,066,884 B2 | 6/2006 | Custer et al. | |
| 7,098,803 B2 | 8/2006 | Mann et al. | |
| 7,120,483 B2 | 10/2006 | Russell et al. | |
| 7,146,202 B2 * | 12/2006 | Ward ................. | A61B 5/145 600/345 |
| 7,310,543 B2 * | 12/2007 | Smart ............... | A61B 5/14532 600/345 |
| 7,310,544 B2 | 12/2007 | Brister et al. | |
| 7,366,566 B2 | 4/2008 | Brister et al. | |
| 7,424,318 B2 | 9/2008 | Brister et al. | |
| 7,460,898 B2 | 12/2008 | Brister et al. | |
| 7,467,003 B2 | 12/2008 | Brister et al. | |
| 7,494,465 B2 | 2/2009 | Brister et al. | |
| 7,497,827 B2 | 3/2009 | Brister et al. | |
| 7,577,470 B2 | 8/2009 | Shah et al. | |
| 7,615,007 B2 | 11/2009 | Shults et al. | |
| 7,831,287 B2 | 11/2010 | Brister et al. | |
| 7,885,697 B2 | 2/2011 | Brister et al. | |
| 7,896,809 B2 | 3/2011 | Simpson et al. | |
| 7,899,511 B2 | 3/2011 | Shults et al. | |
| 7,901,354 B2 | 3/2011 | Shults et al. | |
| 7,949,381 B2 | 5/2011 | Brister et al. | |
| 8,133,178 B2 | 3/2012 | Brauker et al. | |
| 8,224,410 B2 * | 7/2012 | Hadvary ............ | A61B 5/14514 600/310 |
| 8,483,792 B2 | 7/2013 | Slomski et al. | |
| 8,512,243 B2 * | 8/2013 | Stafford ............ | A61B 5/14532 600/309 |
| 9,357,951 B2 * | 6/2016 | Simpson ............ | A61B 5/14532 |
| 9,480,421 B2 * | 11/2016 | Stafford ............ | A61B 5/14532 |
| 2002/0072720 A1 | 6/2002 | Hague et al. | |
| 2002/0137998 A1 * | 9/2002 | Smart ............... | A61B 5/14532 600/347 |
| 2002/1285465 | 9/2002 | Silver | |
| 2003/0100040 A1 | 5/2003 | Bonnecase et al. | |
| 2003/0125613 A1 | 7/2003 | Enegren et al. | |
| 2003/0212346 A1 | 11/2003 | Hyuzhakov et al. | |
| 2004/0010207 A1 | 1/2004 | Flaherty et al. | |
| 2004/0039298 A1 | 2/2004 | Abreu | |
| 2004/0078219 A1 | 4/2004 | Kaylor | |
| 2004/0152622 A1 | 8/2004 | Keith et al. | |
| 2004/0176672 A1 | 9/2004 | Silver et al. | |
| 2004/0180391 A1 | 9/2004 | Gratzl et al. | |
| 2004/0242982 A1 | 12/2004 | Sakata et al. | |
| 2005/0051427 A1 | 3/2005 | Brauker et al. | |
| 2006/0001550 A1 | 1/2006 | Mann et al. | |
| 2006/0016700 A1 | 1/2006 | Brister et al. | |
| 2006/0019327 A1 | 1/2006 | Brister et al. | |
| 2006/0020188 A1 | 1/2006 | Kamath et al. | |
| 2006/0020190 A1 | 1/2006 | Kamath et al. | |
| 2006/0020191 A1 | 1/2006 | Brister et al. | |
| 2006/0020192 A1 | 1/2006 | Brister et al. | |
| 2006/0036139 A1 | 2/2006 | Brister et al. | |
| 2006/0036140 A1 | 2/2006 | Brister et al. | |
| 2006/0036141 A1 | 2/2006 | Kamath et al. | |
| 2006/0036142 A1 | 2/2006 | Brister et al. | |
| 2006/0036143 A1 | 2/2006 | Brister et al. | |
| 2006/0036145 A1 | 2/2006 | Brister et al. | |
| 2006/0052745 A1 | 3/2006 | Van Antwerp et al. | |
| 2006/0079740 A1 | 4/2006 | Silver et al. | |
| 2006/0094946 A1 | 5/2006 | Kellogg et al. | |
| 2006/0142651 A1 | 6/2006 | Brister et al. | |
| 2006/0155180 A1 | 7/2006 | Brister et al. | |
| 2006/0133934 A1 | 8/2006 | Dobbles et al. | |
| 2006/0183985 A1 | 8/2006 | Brister et al. | |
| 2006/0200020 A1 | 9/2006 | Brister et al. | |
| 2006/0200970 A1 | 9/2006 | Brister et al. | |
| 2006/0222566 A1 | 10/2006 | Brauker et al. | |
| 2006/0229512 A1 | 10/2006 | Petisce et al. | |
| 2006/0235285 A1 | 10/2006 | Brister et al. | |
| 2006/0253085 A1 | 11/2006 | Geismar et al. | |
| 2006/0258929 A1 | 11/2006 | Goode et al. | |
| 2006/0263839 A1 | 11/2006 | Ward et al. | |
| 2006/0293576 A1 | 12/2006 | Van Antwerp et al. | |
| 2007/0016381 A1 | 1/2007 | Kamath et al. | |
| 2007/0027370 A1 | 2/2007 | Brauker et al. | |
| 2007/0027384 A1 | 2/2007 | Brister et al. | |
| 2007/0032717 A1 | 2/2007 | Brister et al. | |
| 2007/0059196 A1 | 3/2007 | Brister et al. | |
| 2007/0066873 A1 | 3/2007 | Kamath et al. | |

(56) References Cited

U.S. PATENT DOCUMENTS

| | | | |
|---|---|---|---|
| 2007/0078322 A1* | 4/2007 | Stafford | A61B 5/14532 600/347 |
| 2007/0093704 A1 | 4/2007 | Brister et al. | |
| 2007/0129619 A1 | 6/2007 | Ward et al. | |
| 2007/0163880 A1 | 7/2007 | Woo et al. | |
| 2007/0173710 A1 | 7/2007 | Petisce et al. | |
| 2007/0197890 A1 | 8/2007 | Boock et al. | |
| 2007/0203966 A1 | 8/2007 | Brauker et al. | |
| 2007/0208244 A1 | 9/2007 | Brauker et al. | |
| 2007/0208245 A1 | 9/2007 | Brauker et al. | |
| 2007/0208246 A1 | 9/2007 | Brauker et al. | |
| 2007/0213611 A1 | 9/2007 | Simpson et al. | |
| 2007/0225675 A1 | 9/2007 | Robinson et al. | |
| 2007/0232879 A1 | 10/2007 | Brister et al. | |
| 2008/0033269 A1 | 2/2008 | Zhang | |
| 2008/0086042 A1 | 4/2008 | Brister et al. | |
| 2008/0086044 A1 | 4/2008 | Brister et al. | |
| 2008/0108942 A1 | 5/2008 | Brister et al. | |
| 2008/0119703 A1 | 5/2008 | Brister et al. | |
| 2008/0119704 A1 | 5/2008 | Brister et al. | |
| 2008/0119706 A1 | 5/2008 | Brister et al. | |
| 2008/0197024 A1 | 8/2008 | Simpson et al. | |
| 2008/0200788 A1 | 8/2008 | Brister et al. | |
| 2008/0200789 A1 | 8/2008 | Brister et al. | |
| 2008/0200791 A1 | 8/2008 | Simpson et al. | |
| 2008/0208025 A1 | 8/2008 | Shults et al. | |
| 2008/0214915 A1 | 9/2008 | Brister et al. | |
| 2008/0242961 A1 | 10/2008 | Brister et al. | |
| 2008/0275313 A1 | 11/2008 | Brister et al. | |
| 2009/0018424 A1 | 1/2009 | Kamath et al. | |
| 2009/0076360 A1 | 3/2009 | Brister et al. | |
| 2009/0076361 A1 | 3/2009 | Kamath et al. | |
| 2009/0099436 A1 | 4/2009 | Brister et al. | |
| 2009/0124879 A1 | 5/2009 | Brister et al. | |
| 2009/0131768 A1 | 5/2009 | Simpson et al. | |
| 2009/0131769 A1 | 5/2009 | Leach et al. | |
| 2009/0131776 A1 | 5/2009 | Simpson et al. | |
| 2009/0131777 A1 | 5/2009 | Simpson et al. | |
| 2009/0137886 A1 | 5/2009 | Shariati et al. | |
| 2009/0137887 A1 | 5/2009 | Shariati et al. | |
| 2009/0143659 A1 | 6/2009 | Li et al. | |
| 2009/0143660 A1 | 6/2009 | Brister et al. | |
| 2010/0331642 A1 | 12/2010 | Bruce et al. | |
| 2011/0073475 A1 | 3/2011 | Kastanos et al. | |
| 2011/0077490 A1 | 3/2011 | Simpson et al. | |
| 2012/0190952 A1 | 7/2012 | Stafford et al. | |
| 2013/0253289 A1* | 9/2013 | Hadvary | A61B 5/14514 600/309 |
| 2014/0213866 A1 | 7/2014 | Simpson et al. | |
| 2015/0289788 A1 | 10/2015 | Simpson et al. | |
| 2016/0113556 A1 | 4/2016 | Simpson et al. | |
| 2018/0042529 A1 | 2/2018 | Simpson et al. | |

FOREIGN PATENT DOCUMENTS

| | | |
|---|---|---|
| EP | 0 127 958 | 12/1984 |
| EP | 0 320 109 | 6/1989 |
| EP | 0 351 892 | 1/1990 |
| EP | 0 512 122 | 11/1992 |
| EP | 0 539 751 | 5/1993 |
| EP | 0 351 891 | 9/1993 |
| EP | 0 478 550 | 1/1995 |
| EP | 1 077 634 | 2/2001 |
| EP | 1 078 258 | 2/2001 |
| EP | 1 266 607 | 12/2002 |
| EP | 1 077 636 | 1/2004 |
| EP | 1 413 245 A2 | 4/2004 |
| EP | 1 522 255 B1 | 5/2008 |
| WO | WO 1989/002720 | 4/1989 |
| WO | WO 1990/007575 | 7/1990 |
| WO | WO 1990/010861 | 9/1990 |
| WO | WO 1995/013838 | 5/1995 |
| WO | WO 1996/001611 | 1/1996 |
| WO | WO 1996/014026 | 5/1996 |
| WO | WO 1996/025089 | 8/1996 |
| WO | WO 1997/001986 | 1/1997 |
| WO | WO 1997/002811 | 1/1997 |
| WO | WO 1997/006727 | 2/1997 |
| WO | WO 1997/022291 | 6/1997 |
| WO | WO 1998/066423 | 2/1998 |
| WO | WO 1998/030891 | 7/1998 |
| WO | WO 1998/034541 | 8/1998 |
| WO | WO 1998/038906 | 9/1998 |
| WO | WO 1998/056293 | 12/1998 |
| WO | WO 1999/056613 | 4/1999 |
| WO | WO 1999/033504 | 7/1999 |
| WO | WO 1999/058051 | 11/1999 |
| WO | WO 1999/058973 | 11/1999 |
| WO | WO 1999/059657 | 11/1999 |
| WO | WO 2000/019887 | 4/2000 |
| WO | WO 2000/035530 | 6/2000 |
| WO | WO 2000/045696 | 8/2000 |
| WO | WO 2000/049940 | 8/2000 |
| WO | WO 2000/059373 | 10/2000 |
| WO | WO 2001/012158 | 2/2001 |
| WO | WO 2001/058348 | 8/2001 |
| WO | WO 2001/068901 | 9/2001 |
| WO | WO 2001/069222 | 9/2001 |
| WO | WO 2001/088534 | 11/2001 |
| WO | WO 2002/002755 | 1/2002 |
| WO | WO 2002/089666 | 11/2002 |
| WO | WO 2003/011131 | 2/2003 |
| WO | WO 2003/063700 | 8/2003 |
| WO | WO 2004/063718 | 7/2004 |
| WO | WO 2004/098685 | 11/2004 |
| WO | WO 2005/026689 | 3/2005 |
| WO | WO 2006/017358 | 3/2005 |
| WO | WO 2006/018425 | 2/2006 |
| WO | WO 2006/029293 | 3/2006 |
| WO | WO 2006/105146 | 10/2006 |
| WO | WO 2006/122048 | 11/2006 |
| WO | WO 2006/124759 | 11/2006 |
| WO | WO 2007/041070 | 4/2007 |
| WO | WO 2007/097754 | 8/2007 |
| WO | WO 2007/114943 | 10/2007 |
| WO | WO 2008/001091 | 1/2008 |
| WO | WO 2008/005780 | 1/2008 |
| WO | WO 2008/031106 | 3/2008 |
| WO | WO 2008/031110 | 3/2008 |
| WO | WO 2008/073813 | 6/2008 |

OTHER PUBLICATIONS

Abel et al. 2002. Biosensors for in vivo glucose measurement: can we cross the experimental stage. Biosensenors & Bioelectronics 17:1059-1070.

Armour et al. Dec. 1990. Application of Chronic Intravascular Blood Glucose Sensor in Dogs. Diabetes 39:1519-1526.

Bani Amer M. M. 2002. A n accurate amperometric glucose sensor based glucometer with eliminated cross-sensitivity. J Med Engindeering Technology 26(5):208-213.

Bindra et al. 1991. Design and In Vitro Studies of a Needle-Type Glucose Sensor for Subcutaneous Monitoring Analytical Chemistry 63:1692-1696.

Bruckel et al. 1989. In vivo measurement of subcutaneous glucose concentrations with an enzymatic glucose sensor and a wick method. Klin Wochenschr 67:491-495.

Cameron et al. 1997. Micromodular Implants to provide electrical stimulation of paralyzed muscles and limbs. IEEE Transactions Biomedical Engineering 44(9):781-790.

Claremont et al. 1986. Subcutaneous implantation of a ferrocene-mediated glucose sensor in pigs. Diabetologia 29:817-821.

Claremont et al. Jul. 1986. Potentially-implantable ferrocene-mediated glucose sensor. J. Biomed. Eng. 8:272-274.

Csoregi et al. 1994. Design characterization and one-point in vivo calibration of a subcutaneously implanted glucose electrode. Analytical Chemistry 66(19):3131-3138.

El-Khatib et al. 2007. Adaptive closed-loop control provides blood-glucose regulation using dual subcutaneous insulin and glucagon infusion in diabetic swine. Journal of Diabetes Science and Technology 1(2)181-192.

(56) References Cited

OTHER PUBLICATIONS

Fischer et al. 1987. Assessment of subcutaneous glucose concentration: validation of the wick technique as a reference for implanted electrochemical sensors in normal and diabetic dogs. Diabetologia 30:940-945.
Ganesh et al. Mar. 2008. Evaluation of the VIA® blood chemistry monitor for glucose in healthy and diabetic volunteers. Journal of Diabetes Science and Technology 2(2): 182-193.
Gerritsen et al. 1999. Performance of subcutaneously implanted glucose sensors for continuous monitoring. The Netherlands Journal of Medicine 54:167-179.
Hamilton Syringe Selection Guide. 2006. Syringe Selection www.hamiltoncompany.com (20 pages).
Heller A. 1992. Electrical Connection of Enzyme Redox Centers to Electrodes. J. Phys. Chem. 96:3579-3587.
Heller A. 1999. Implanted electrochemical glucose sensors for the management of diabetes. Annu Rev Biomed Eng 1:153-175.
Hrapovic et al. 2003. Picoamperometric detection of glucose at ultrasmall platinum-based biosensors: preparation and characterization. Analytical Chemistry 75:3308-3315.
Hunter et al. Mar. 31, 2000. Minimally Invasive Glucose Sensor and Insulin Delivery System. MIT Home Automation and Healthcare Consortium. Progress Report No. 2-5. (17 pages).
Jaremko et al. 1998. Advances toward the implantable artificial pancreas for treatment of diabetes. Diabetes Care 21(3):444-450.
Johnson et al. 1992. In vivo evaluation of an eiectroenzymatic glucose sensor implanted subcutaneous tissue. Biosensors & Bioelectronics 7:709-714.
Kang et al. 2003. In vitro and short-term in vivo characteristics of a Kel-F thin film modified glucose sensor. Analytical Science 19:1481-1486.
Kerner et al. 1993. The function of a hydrogen peroxide-detecting electroenzymatic glucose electrode is markedly impaired in human sub-cutaneous tissue and plasma. Biosensors & Bioelectronics 8:473-482.
Klueh et al. 2003. Use of Vascular Endothelial Cell Growth Factor Gene Transfer to Enhance Implantable Sensor Function in Vivo. J. Biomed. Mat Res 67A:1072-1086.
Klueh et al. 2007. Inflammation and glucose sensors: use of dexamethasone to extend glucose sensor function and life span in vivo. Journal of Diabetes Science and Technology 1(4):496-504.
Koschinsky et al. 2001. Sensors for glucose monitoring: Technical and clinical aspects. Diabetes Metab. Res. Rev. 17:113-123.
Kusano H. 1989. Glucose enzyme electrode with percutaneous interface which operates independently of dissolved oxygen. Clin Phys Physiol Meas. 10(1):1-9.
Makale et al. 2003. Tissue window chamber system for validation of implanted oxygen sensors. Am. J. Physiol. Heart Circ. Physiol. 284:H2288-2294.
Mastrototaro et al. 1991. An electroenzymatic glucose sensor fabricated on a flexible substrate. Sensors and Actuators B 5:139-44.
Miller et al. 2012. Multiplexed microneedle-based biosensor array for characterization of metabolic acidosis. Short Communication—Talana 88:739-742. (Available online Nov. 22, 2011).
Ohara et al. 1994. "Wired" enzyme electrodes for amperometric determination of glucose or lactate in the presence of interfering substances. Analytical Chemistry 66:2451-2457.
Ohara et al. Dec. 1993. Glucose electrodes based on cross-linked bis(22'-bipyridine)chloroosmium(+/2+) complexed poly(l-vinylimidazole) films. Analytical Chemistry 65:3512-3517.
Palmisano et al. 2000. Simultaneous monitoring of glucose and lactate by an interference and crosstalk free dual electrode amperometric biosensor based on electropolymerized thin films. Biosensors & Bioelectronics 15:531-539.
Pickup et al. 1988. Progress towards in vivo glucose sensing with a ferrocene-mediated amperometric enzyme electrode. Horm. Metab. Res. Supp. 20:34-36.
Pineda et al. 1996. Bone regeneration with resorbable polymeric membranes. III. Effect of poly(L-lactide) membrane pore size on the bone healing process in large defects. J. Biomedical Materials Research 31:385-394.
Quinn et al. 1995. Kinetics of glucose delivery to subcutaneous tissue in rats measured with 0.3-mm amperometric microsensors. Am. J. Physiol. 269 (Endocrinol. Metab. 32)E155-E161.
Quinn et al. 1997. Biocompatible glucose-permeable hydrogel for in situ coating of implantable biosensors. Biomaterials 18:1665-1670.
Rebrin et al. 1992. Subcutaneous glucose monitoring by means of electrochemical: fiction or reality? J. Biomed. Eng. 14:33-40.
Sanders et al. 2003. Fibrous Encapsulation of Single Polymer Microfibers Depends on their Vertical Dimension in subcutaneous Tissue Polymer Microfibers. J. Biomed Mater Res 67A:1181-1187.
Schmidt et al. 1993. Glucose concentration in subcutaneous extracellular space. Diabetes Care 16(5):695-700.
Schmidtke et al. Jan. 1998. Measurement and modeling of the transient difference between blood and subcutaneous glucose concentrations in the rat after injection of insulin. Proc Natl Acad Sci U S A 95: 294-299.
Schoemaker et al. 2003. The SCGM1 system: Subcutaneous continuous glucose monitoring based on microdialysis technique. Diabetes Technology & Therapeutics 5(4)599-608.
Sharkawy et al. 1997. Engineering the tissue which encapsulates subcutaneous implants. I. Diffusion properties. J Biomed Mater Res 37:401-412.
Shults et al. 1994. A telemetry-instrumentation system for monitoring multiple subcutaneously implanted glucose sensors. IEEE Transactions on Biomedical Engineering 41(10):937-942.
Sternberg et al. 1988. Covalent enzyme coupling on cellulose acetate membranes for glucose sensor development. Analytical Chemistry 60: 2781-2786.
Tang et al. 1993. Fibrin(ogen) mediates acute inflammatory responses to biomaterials. J Exp Med 178:2147-2156.
Trajanoski et al. 1998. Neural predictive controller for insulin delivery using the subcutaneous route. IEEE Transactions on Biomedical Engineering 45(9): 1122-1134.
Updike et al. 1997. Principles of long-term fully implanted sensors with emphasis on radiotelemetric monitoring of blood glucose form inside a subcutaneous foreign body capsule (FBC). Fraser D.M. (Ed.) Biosensors in the Body. New York. John Wiley & Sons Ltd. pp. 117-137.
Vadgama. 1988. Diffusion limited enzyme electrodes. NATO ASI Series: Series C Math and Phys. Sci. 226:359-377.
Valdes-Ramirez et al. 2012. Multiplexed and switchable release of distinct fluids from microneedle platforms via conducting polymer nanoactuators for potential drug delivery. Sensors & Actuators B 161: 1018-1024.
Wagner et al. 1998. Continuous amperometric monitoring of glucose in a brittle diabetic chimpanzee with a miniature subcutaneous electrode. Proc. Natl. Acad. Sci. A 95:6379-6382.
Wang et al. 1994. Highly Selective Membrane-Free Mediator-Free Glucose Biosensor. Analytical Chemistry 66:3600-3603.
Ward et al. 2000. Rise in background current overtime in a subcutaneous glucose sensor in the rabbit: Relevance to calibration and accuracy. Biosensors & Bioelectronics 15:53-61.
Wientjes K. J. C. 2000. Development of a glucose sensor for diabetic patients (Ph.D. Thesis).
Wikipedia 2006. "Intravenous therapy" http://en.wikipedia.org/wiki/Intravenous_therapy Aug. 15, 2006 (6 pages).
Wilkins et al. 1996. Glucose monitoring: state of the art and future possibilities. Med Eng Phys 18:273-288.
Windmiller et al. 2011. Bicomponent Microneedle Array Biosensor for Minimally-invasive Glutamate Monitoring. Electroanalysis 23(10): 2302-2309.
Windmiller et al. 2011. Microneedle array-based carbon paste amperometric sensors and biosensors. Analyst 136:1846-1851.
Yang et al. 1998. Development of needle-type glucose sensor with high selectivity. Science and Actuators B 46:249-256.
Zhang et al. 1994. Elimination of the acetaminophen interference in an implantable glucose sensor. Analytical Chemistry 66(7): 1183-1188.

(56) References Cited

OTHER PUBLICATIONS

Ziaie et al. 1997. A single-channel implantable microstimulator for functional neuromuscular stimulation. IEEE Transactions on Biomedical Engineering 44(10):909-920.
PCT/US2010/050788, filed 29-SE-2010: International Search Report and Written Opinion dated May 13, 2011.
PCT/US2010/050788, filed 29-SE-2010: International Preliminary Report on Patentability dated Apr. 3, 2012.

\* cited by examiner

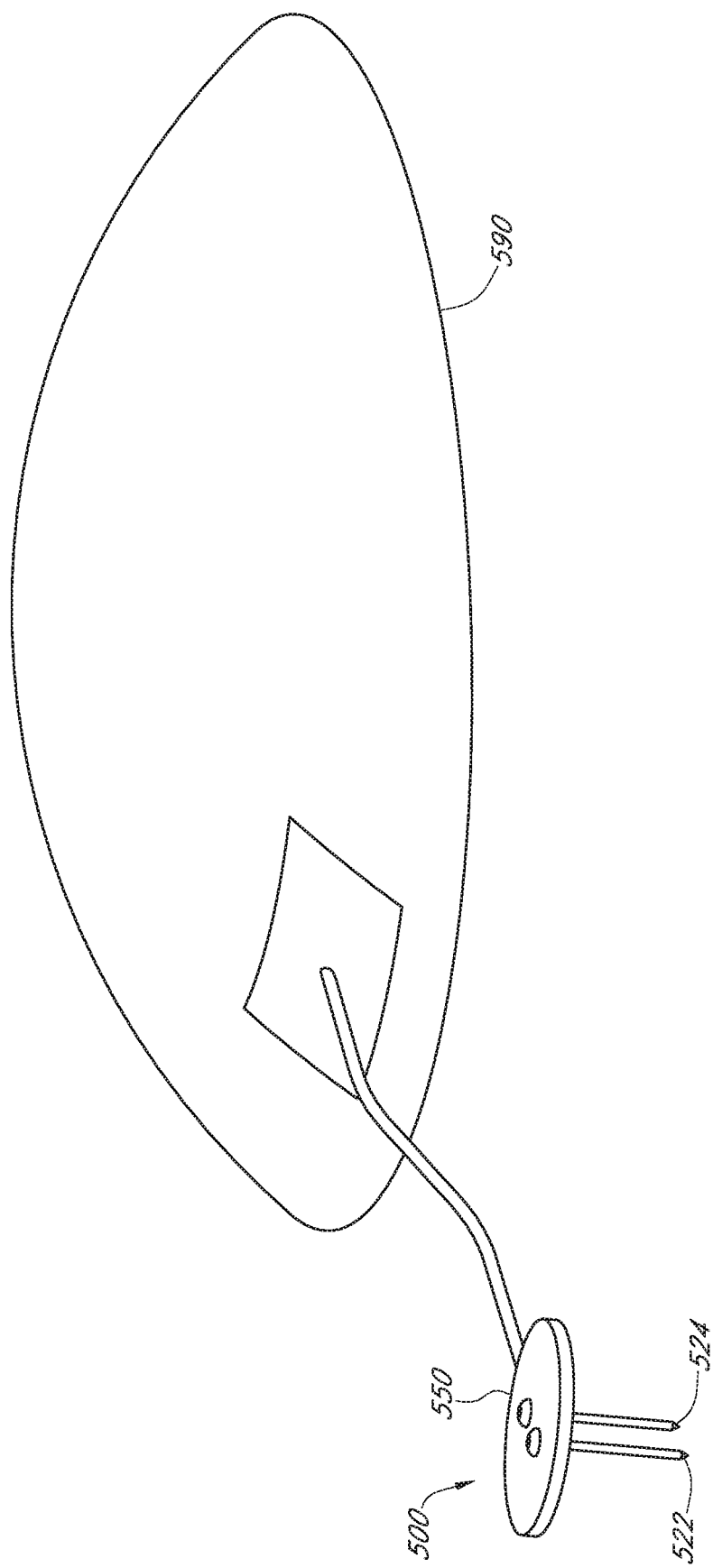

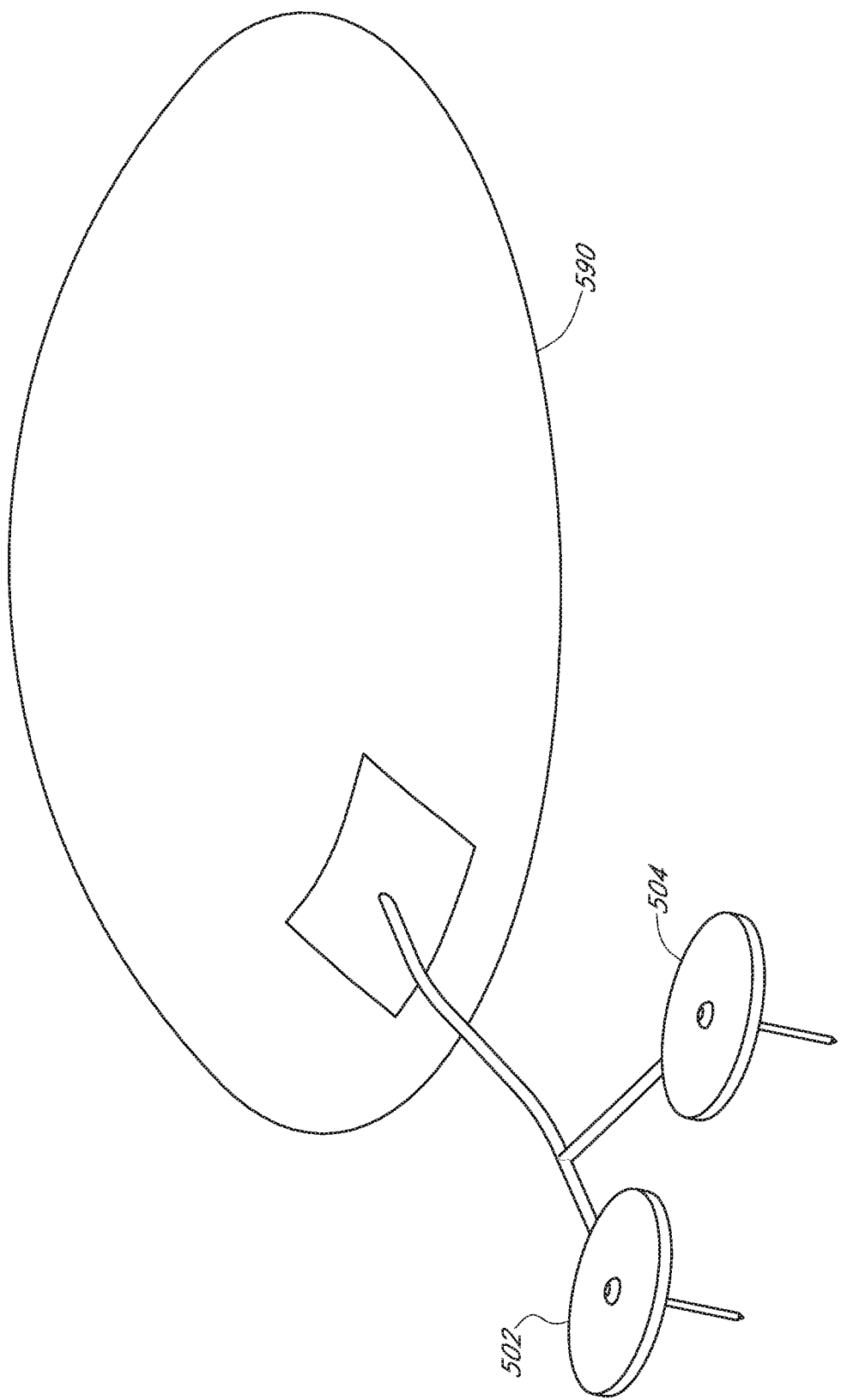

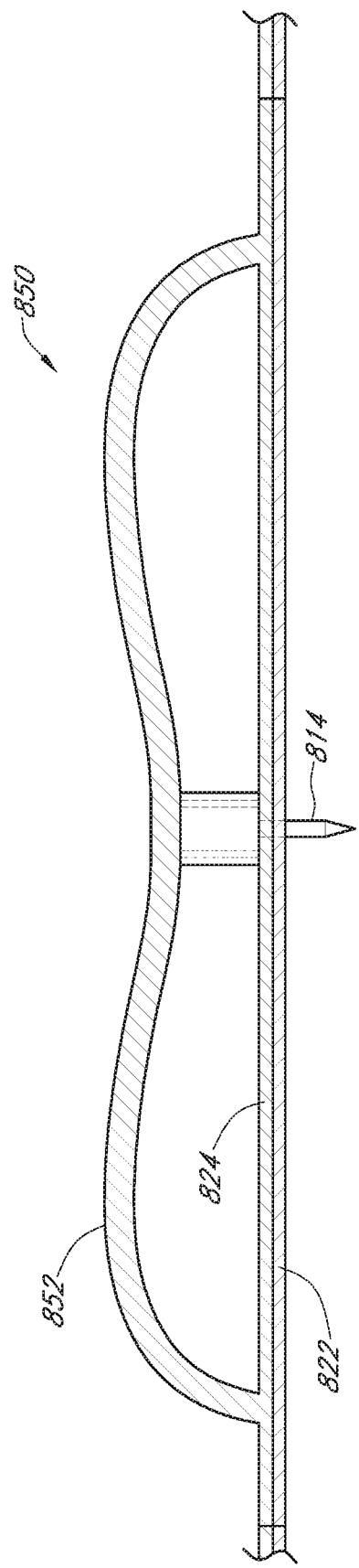

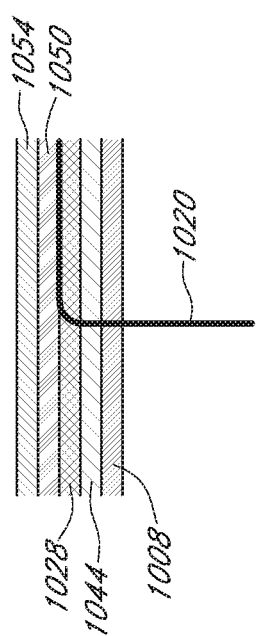
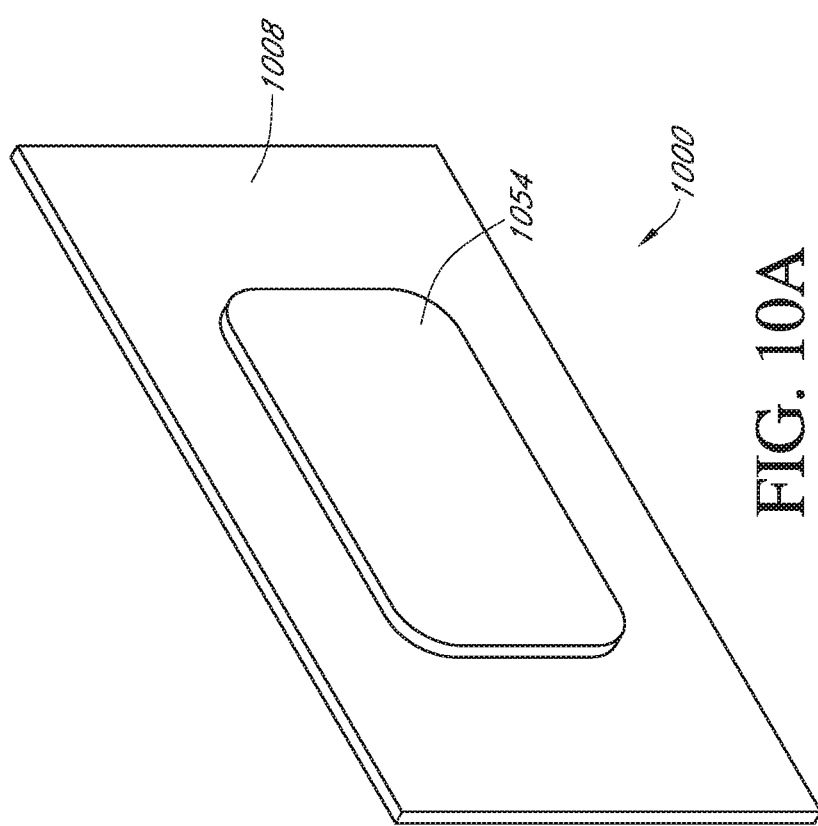
FIG. 10B
FIG. 10A

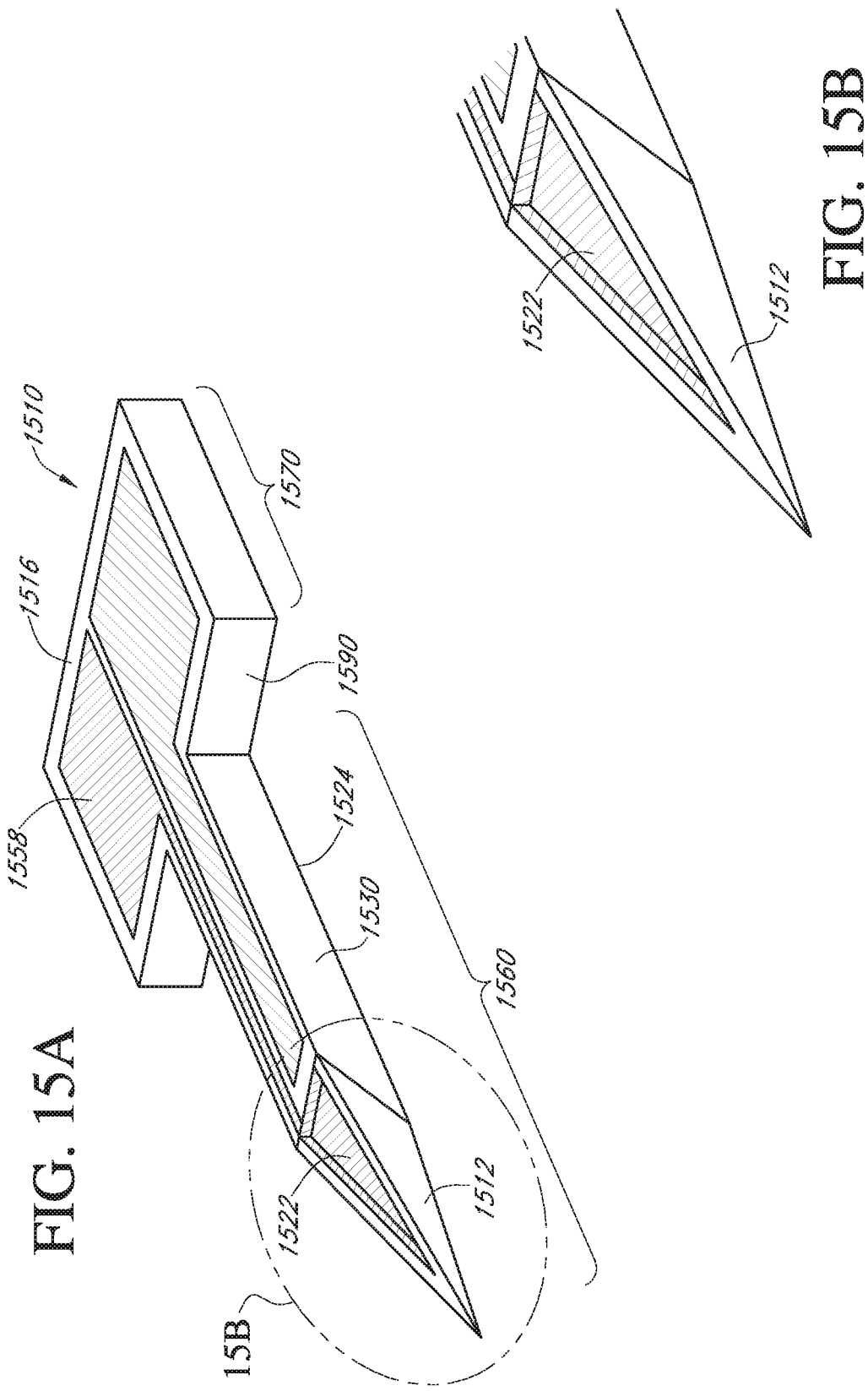

TRANSCUTANEOUS ANALYTE SENSOR

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 12/893,850, filed on Sep. 29, 2010, which claims the benefit of priority under 35 U.S.C. § 119(e) to Provisional Application No. 61/247,463, filed on Sep. 30, 2009. Each of the aforementioned applications is incorporated by reference herein in its entirety, and each is hereby expressly made a part of this specification.

FIELD OF THE INVENTION

The embodiments described herein relate generally to analyte sensors.

BACKGROUND OF THE INVENTION

Diabetes mellitus is a chronic disease, which occurs when the pancreas does not produce enough insulin (Type I), or when the body cannot effectively use the insulin it produces (Type II). This condition typically leads to an increased concentration of glucose in the blood (hyperglycemia), which can cause an array of physiological derangements (e.g., kidney failure, skin ulcers, or bleeding into the vitreous of the eye) associated with the deterioration of small blood vessels. Or, a hypoglycemic reaction (low blood sugar) is induced by an inadvertent overdose of insulin, or after a normal dose of insulin or glucose-lowering agent accompanied by extraordinary exercise or insufficient food intake.

A variety of transcutaneous sensor devices have been developed for continuously measuring blood glucose concentrations. Typically, these types of sensor devices employ an applicator or other similar insertion tool for inserting a transcutaneous sensor under a host's skin. Conventionally, the applicator comprises a plunger and a needle formed with a lumen configured to receive the sensor. Because of the additional parts (e.g., an applicator with a plunger) and steps (e.g., a sensor unit retraction step) required for sensor deployment, use of a separate applicator or other similar tools for sensor insertion can be cumbersome, or difficult, particularly for a new user.

SUMMARY OF THE INVENTION

In a first aspect, a sensor device is provided for measuring an analyte concentration, the sensor device comprising: a sensor unit comprising a tissue piercing element and a sensor body, the sensor body comprising at least one electrode and a membrane covering at least a portion of the at least one electrode, wherein the sensor unit is configured to have a column strength sufficient to allow the sensor unit to be inserted through a skin of a host without substantial buckling; and a mounting unit configured to support the sensor device on an exterior surface of the skin of the host.

In an embodiment of the first aspect, the sensor unit is configured to have a length that allows for at least a portion of the sensor body to reside within a stratum germinativum of the skin, e.g., from about 0.1 mm to about 1.5 mm.

In an embodiment of the first aspect, the sensor unit is configured to have a length that allows for at least a portion of the sensor body to reside within a dermis of the skin, e.g., from about 1 mm to about 7 mm.

In an embodiment of the first aspect, the sensor unit is configured to have a length that allows for at least a portion of the sensor body to reside within a subcutaneous layer of the skin, e.g., from about 3 mm to about 10 mm.

In an embodiment of the first aspect, the tissue piercing element is configured to protect the membrane from damage during insertion of the sensor unit.

In an embodiment of the first aspect, the tissue piercing element is configured to withstand an axial load greater than about 1 Newton without substantial buckling.

In an embodiment of the first aspect, the tissue piercing element comprises at least one material selected from the group consisting of metals, ceramics, semiconductors, organics, polymers, composites, and combinations thereof.

In an embodiment of the first aspect, a largest dimension of a cross section transverse to a longitudinal axis of the tissue piercing element is greater than a largest dimension of a cross section transverse to a longitudinal axis of the sensor body.

In an embodiment of the first aspect, a largest dimension of a cross section transverse to a longitudinal axis of the tissue piercing element is less than about 0.1 mm.

In an embodiment of the first aspect, a largest dimension of a cross section transverse to a longitudinal axis of the sensor body is less than about 0.05 mm.

In an embodiment of the first aspect, the at least one electrode comprises a working electrode and a reference electrode.

In an embodiment of the first aspect, the sensor body further comprises a support member configured to protect the membrane from damage during insertion of the sensor unit.

In an embodiment of the first aspect, the support member comprises at least one material selected from the group consisting of stainless steel, titanium, tantalum, platinum, platinum-iridium, iridium, polymers, ceramics, composites, and combinations thereof.

In an embodiment of the first aspect, the support member is configured to withstand an axial load greater than about 1 Newton without substantial buckling.

In an embodiment of the first aspect, the at least one electrode forms the support member.

In an embodiment of the first aspect, the support member is configured to support at least a portion of the at least one electrode.

In an embodiment of the first aspect, the support member is configured to partially surround the at least one electrode.

In an embodiment of the first aspect, the support member is configured to substantially surround the at least one electrode.

In an embodiment of the first aspect, the support member comprises at least one window portion configured to allow passage of a biological fluid to the membrane.

In an embodiment of the first aspect, the mounting unit comprises a guiding portion configured to provide guidance and enhance a column strength of the sensor unit as the sensor unit is inserted through the skin.

In an embodiment of the first aspect, the mounting unit comprises a sensor electronics unit operatively connected to the sensor body.

In an embodiment of the first aspect, the sensor electronics unit is connected to the sensor body via contacts configured to provide mechanical and electrical connection between the sensor electronics unit and the sensor body In an embodiment of the first aspect, the sensor body is directly hardwired to the sensor electronics unit.

In an embodiment of the first aspect, the sensor electronics unit is configured to be located over a sensor insertion site.

In an embodiment of the first aspect, the sensor electronics unit is configured to be detachably connected to the mounting unit via a tethered connection In an embodiment of the first aspect, the sensor electronics unit is configured to be releasably attached to the mounting unit.

In an embodiment of the first aspect, the mounting unit comprises a color display element configured to display at least one of a first color when analyte concentration is below a preselected target range, a second color when analyte concentration is within a preselected target range, or a third color when analyte concentration is above a preselected target range.

In an embodiment of the first aspect, the color display element is configured to display a color gradation that represents a degree of change in an analyte concentration.

In an embodiment of the first aspect, the mounting unit comprises a user interface.

In an embodiment of the first aspect, the user interface is configured to display a representation of a range of analyte values that are associated with an analyte concentration.

In an embodiment of the first aspect, the user interface is configured to display a directional trend of the analyte concentration.

In an embodiment of the first aspect, the user interface is configured to display at least one graphical illustration indicating at least one area of increasing clinical risk.

In an embodiment of the first aspect, the user interface is configured to change at least one of colors or illustrations that represent a nearness to a clinical risk.

In a second aspect, a device is provided for measuring an analyte concentration in a host, the device comprising: a sensor configured for press insertion through a skin of a host, the sensor comprising at least one electrode, a membrane covering at least a portion of the at least one electrode, and a distal tip configured for piercing tissue, wherein the at least one electrode has sufficient column strength to allow the sensor to be inserted through the skin of the host without substantial buckling.

In an embodiment of the second aspect, the sensor is configured to have a length that allows for at least a portion of the at least one electrode to reside within a stratum germinativum of the skin, e.g., from about 0.2 mm to about 1.5 mm.

In an embodiment of the second aspect, the sensor is configured to have a length that allows for at least a portion of the at least one electrode to reside within a dermis of the skin, e.g., from about 1 mm to about 7 mm.

In an embodiment of the second aspect, the sensor is configured to have a length that allows for at least a portion of the at least one electrode to reside within a subcutaneous layer of the skin, e.g., from about 3 mm to about 10 mm.

In an embodiment of the second aspect, the distal tip is configured to protect the membrane from damage during insertion of the sensor.

In an embodiment of the second aspect, the sensor is configured to withstand an axial load greater than about 1 Newton without substantial buckling.

In an embodiment of the second aspect, the distal tip comprises at least one material selected from the group consisting of metals, ceramics, semiconductors, organics, polymers, composites, and combinations thereof.

In an embodiment of the second aspect, wherein a largest dimension of a cross section transverse to a longitudinal axis of the distal tip is greater than a largest dimension of a cross section transverse to a longitudinal axis of the at least one electrode.

In an embodiment of the second aspect, a largest dimension of a cross section transverse to a longitudinal axis of the distal tip is less than about 0.1 mm.

In an embodiment of the second aspect, a largest dimension of a cross section transverse to a longitudinal axis of the at least one electrode is less than about 0.05 mm.

In an embodiment of the second aspect, the at least one electrode comprises a working electrode and a reference electrode.

In an embodiment of the second aspect, the at least one electrode comprises at least one material selected from the group consisting of stainless steel, titanium, tantalum, platinum, platinum-iridium, iridium, polymers, ceramics, composites, and combinations thereof.

In an embodiment of the second aspect, the at least one electrode is configured to withstand an axial load greater than about 1 Newton without substantial buckling.

In a third aspect, a sensor device is provided for measuring an analyte concentration in a host, the sensor device comprising: at least one electrode comprising a distal end, an electroactive surface, and a membrane located over at least a portion of the electroactive surface, the membrane configured to limit transport of analyte to the electroactive surface; and a tip portion attached to the distal end of the at least one electrode and configured to pierce tissue; wherein a largest dimension of a cross section transverse to a longitudinal axis of the tip portion is greater than a largest dimension of a cross section transverse to a longitudinal axis of the at least one electrode.

In an embodiment of the third aspect, the sensor device is configured to have a length allowing for at least a portion of the at least one electrode to reside within a stratum germinativum of the skin.

In an embodiment of the third aspect, the sensor device is configured to have a length allowing for at least a portion of the at least one electrode to reside within a dermis of the skin.

In an embodiment of the third aspect, the sensor device is configured to have a length allowing for at least a portion of the at least one electrode to reside within a subcutaneous layer of the skin.

In an embodiment of the third aspect, the tip portion is configured to protect the membrane from damage during insertion of the sensor device.

In an embodiment of the third aspect, the tip portion is configured to withstand an axial load greater than about 1 Newton without substantial buckling.

In an embodiment of the third aspect, the tip portion comprises at least one material selected from the group consisting of metals, ceramics, semiconductors, organics, polymers, composites, and combinations thereof.

In an embodiment of the third aspect, the largest dimension of the cross section transverse to the longitudinal axis of the tip portion is less than about 0.1 mm.

In an embodiment of the third aspect, the largest dimension of the cross section transverse to the longitudinal axis of the at least one electrode is less than about 0.05 mm.

In an embodiment of the third aspect, the at least one electrode comprises a working electrode and a reference electrode.

In an embodiment of the third aspect, the at least one electrode comprises at least one material selected from the group consisting of stainless steel, titanium, tantalum, platinum, platinum-iridium, iridium, polymers, ceramics, composites, and combinations thereof.

In an embodiment of the third aspect, the at least one electrode is configured to withstand an axial load greater than about 1 Newton without substantial buckling.

In a fourth aspect, a sensor device is provided for measuring an analyte concentration in a host, the sensor device comprising: a tissue piercing element; a sensor comprising at least one electrode configured to measure a concentration of analyte in a host and a membrane disposed over at least a portion of the at least one electrode and configured to limit transport of analyte to the at least one electrode; and a support member configured to substantially surround the sensor, the support member comprising at least one opening configured to allow passage of a biological fluid to the membrane.

In an embodiment of the fourth aspect, the tissue piercing element is configured to protect the membrane from damage during insertion of the sensor device.

In an embodiment of the fourth aspect, the tissue piercing element is configured to withstand an axial load greater than about 1 Newton without substantial buckling.

In an embodiment of the fourth aspect, the tissue piercing element comprises at least one material selected from the group consisting of metals, ceramics, semiconductors, organics, polymers, composites, and combinations thereof.

In an embodiment of the fourth aspect, the at least one electrode comprises a working electrode and a reference electrode.

In an embodiment of the fourth aspect, the support member comprises at least one material selected from the group consisting of stainless steel, titanium, tantalum, platinum, platinum-iridium, iridium, polymers, ceramics, composites, and combinations thereof.

In an embodiment of the fourth aspect, the support member is configured to withstand an axial load greater than about 1 Newton without substantial buckling.

In a fifth aspect, a device for measuring an analyte concentration in a host is provided, the device comprising: a sensor unit comprising a distal tip and a sensor body comprising an electrode body and a membrane disposed over at least a portion of the electrode body, the electrode body comprising at least one material providing the electrode body with sufficient column strength to allow the sensor body to be inserted through a skin of a host without substantial buckling; and a mounting unit adapted to receive a pressure from a user for insertion of the sensor unit through the skin.

In an embodiment of the fifth aspect, the distal tip is configured to protect the membrane from damage during insertion of the sensor body.

In an embodiment of the fifth aspect, the distal tip is configured to withstand an axial load greater than about 1 Newton without substantial buckling.

In an embodiment of the fifth aspect, the distal tip comprises at least one material selected from the group consisting of metals, ceramics, semiconductors, organics, polymers, composites, and combinations thereof.

In an embodiment of the fifth aspect, the at least one electrode body comprises a working electrode and a reference electrode.

In an embodiment of the fifth aspect, the electrode body comprises at least one material selected from the group consisting of stainless steel, titanium, tantalum, platinum, platinum-iridium, iridium, polymers, ceramics, composites, and combinations thereof.

In an embodiment of the fifth aspect, the electrode body is configured to withstand an axial load greater than about 1 Newtons without substantial buckling.

In an embodiment of the fifth aspect, the mounting unit comprises a guiding portion configured to provide guidance and enhance the column strength of the sensor body as the sensor body is inserted through the skin.

In an embodiment of the fifth aspect, the mounting unit comprises a sensor electronics unit operatively connected to the sensor body.

In an embodiment of the fifth aspect, the sensor electronics unit is connected to the sensor body via contacts configured to provide mechanical and electrical connection between the sensor electronics unit and the sensor body In an embodiment of the fifth aspect, the sensor body is directly hardwired to the sensor electronics unit.

In an embodiment of the fifth aspect, the sensor electronics unit is configured to be located over a sensor insertion site.

In an embodiment of the fifth aspect, the sensor electronics unit is configured to be detachably connected to the mounting unit via a tethered connection In an embodiment of the fifth aspect, the sensor electronics unit is configured to be releasably attached to the mounting unit.

In an embodiment of the fifth aspect, the sensor unit is configured to be in a retracted state hidden inside the mounting unit prior to insertion of the sensor unit.

In an embodiment of the fifth aspect, the mounting unit comprises a color display element configured to display at least one of a first color when analyte concentration is below a preselected target range, a second color when analyte concentration is within a preselected target range, or a third color when analyte concentration is above a preselected target range.

In an embodiment of the fifth aspect, the color display element is configured to display a color gradation that represents a degree of change in analyte concentration.

In an embodiment of the fifth aspect, the mounting unit comprises a user interface.

In an embodiment of the fifth aspect, the user interface is configured to display a representation of a range of analyte values that are associated with analyte concentration.

In an embodiment of the fifth aspect, the user interface is configured to display a directional trend of the analyte concentration.

In an embodiment of the fifth aspect, the user interface is configured to display at least one graphical illustration indicating at least one area of increasing clinical risk.

In an embodiment of the fifth aspect, the user interface is configured to change at least one of colors or illustrations that represent a nearness to a clinical risk.

In a sixth aspect, a sensor array for measuring an analyte concentration is provided, the sensor array comprising: a laminate comprising an adhesive layer configured for adhering the laminate to a skin of a host; and a plurality of sensor devices, each comprising a tissue piercing element configured for piercing tissue and a sensor with an enzyme-containing membrane, wherein the plurality of sensor devices are each attached to the laminate and are each configured for insertion through the skin at a different insertion site.

In an embodiment of the sixth aspect, the laminate comprises sensor electronics operatively connected to the sensor body.

In an embodiment of the sixth aspect, the laminate comprises a transmitter configured to transmit sensor data to a remote computer system.

In an embodiment of the sixth aspect, the plurality of sensor devices is configured to provide parallel measurements of analyte concentration.

In an embodiment of the sixth aspect, the plurality of sensor devices comprise a first sensor device and a second sensor device, wherein the first sensor device comprises a first sensor configured to measure analyte concentration at a first range of analyte concentrations and the second sensor device comprises a second sensor configured to measure analyte concentration at a second range of analyte concentrations, and wherein the first range is different from the second range.

In an embodiment of the sixth aspect, the plurality of sensor devices comprise a first sensor device and a second sensor device, wherein the first sensor device comprises a first sensor configured to reside in a host tissue at a first depth and a second sensor configured to reside in the host tissue at a second depth, and wherein the first depth is different from the second depth.

In an embodiment of the sixth aspect, the sensors and tissue piercing elements of the plurality of sensor devices are each configured to have sufficient column strength to allow for insertion through the skin without substantial buckling.

In an embodiment of the sixth aspect, the tissue piercing element is configured to protect the enzyme-containing membrane from damage during insertion of the sensor.

In an embodiment of the sixth aspect, each of the plurality of sensor devices further comprises a support member configured to substantially surround the sensor, the support member comprising at least one opening configured to allow passage of a biological fluid to the enzyme-containing membrane.

In an embodiment of the sixth aspect, the plurality of sensor devices comprise a first sensor device and a second sensor device, wherein the first sensor device comprises working electrode and the second sensor comprises a reference electrode.

In an embodiment of the sixth aspect, each of the plurality of sensor devices comprises a working electrode and a reference electrode.

In a seventh aspect, a sensor device for measuring an analyte concentration is provided, the sensor device comprising: a sensor unit comprising an in vivo portion having a tissue piercing element and a sensor body, the sensor body comprising at least one electrode and a membrane covering at least a portion of the at least one electrode; and a mounting unit configured to support the sensor device on an exterior surface of a host's skin.

In an embodiment of the seventh aspect, the mounting unit comprises a guiding portion configured to guide insertion of the in vivo portion of the sensor unit through the host's skin and to support a column strength of the sensor unit such that the in vivo portion is capable of being inserted through the host's skin without substantial buckling; and wherein the guiding portion is configured to remain ex vivo during insertion of the in vivo portion of the sensor unit.

In an embodiment of the seventh aspect, the tissue piercing element, with the support of the guiding portion, is capable of withstanding an axial load greater than about 1 Newton without substantial buckling.

In an embodiment of the seventh aspect, the tissue piercing element is configured to protect the membrane from damage during insertion of the in vivo portion of the sensor unit.

In an embodiment of the seventh aspect, a largest dimension of a cross section transverse to a longitudinal axis of the tissue piercing element is greater than a largest dimension of a cross section transverse to a longitudinal axis of the sensor body.

In an embodiment of the seventh aspect, the at least one electrode comprises a working electrode and a reference electrode.

In an embodiment of the seventh aspect, the sensor body further comprises a support member configured to protect the membrane from damage during insertion of the sensor unit.

In an embodiment of the seventh aspect, the at least one electrode is a support member.

In an embodiment of the seventh aspect, the support member, with the support of a guiding member of the mounting unit, is capable of withstanding an axial load greater than about 1 Newton without substantial buckling.

In an embodiment of the seventh aspect, the support member is configured to support at least a portion of the at least one electrode.

In an embodiment of the seventh aspect, the support member is configured to substantially surround the at least one electrode.

In an embodiment of the seventh aspect, the mounting unit comprises a sensor electronics unit operatively and detachably connected to the sensor body.

In an embodiment of the seventh aspect, the sensor electronics unit is configured to be located over a sensor insertion site.

In an eighth embodiment, a sensor array for measuring an analyte concentration is provided, the sensor array comprising: a laminate comprising an adhesive layer configured for adhering the laminate to a host's skin; and a plurality of sensor devices each attached to the laminate and each configured for insertion through the skin at a different insertion site, wherein each sensor device comprises a sensor unit and a mounting unit configured to support the sensor device on an exterior surface of the host's skin, the sensor unit comprising an in vivo portion having a tissue piercing element and a sensor body, the sensor body comprising at least one electrode and a membrane covering at least a portion of the at least one electrode.

In an embodiment of the eighth aspect, the laminate comprises sensor electronics operatively connected to the sensor devices.

In an embodiment of the eighth aspect, the plurality of sensor devices is configured to provide parallel measurements of analyte concentration.

In an embodiment of the eighth aspect, the plurality of sensor devices comprises a first sensor device and a second sensor device, wherein the first sensor device is configured to measure analyte concentration at a first range of analyte concentrations and the second sensor device is configured to measure analyte concentration at a second range of analyte concentrations, wherein the first range is different from the second range.

In an embodiment of the eighth aspect, the plurality of sensor devices comprises a first sensor device and a second sensor device, wherein the first sensor device comprises a first sensor body configured to reside in a host tissue at a first depth, wherein the second sensor device comprises a second sensor body configured to reside in the host tissue at a second depth, and wherein the first depth is different from the second depth.

BRIEF DESCRIPTION OF THE DRAWINGS

FIG. 5C illustrates a perspective view of an embodiment of the sensor device that is connected to the sensor electronics unit via a tether; FIG. 5F illustrates a perspective view of a plurality of sensor devices that are connected to the sensor electronics unit.

FIG. 8D illustrates the embodiment of FIG. 8C, after the sensor insertion process.

FIG. 10A is a perspective view of one embodiment of a sensor device having a disposable thin laminate sensor housing; and FIG. 10B is a cut-away side cross-sectional view of the embodiment illustrated in FIG. 10A.

FIGS. 15A and 15B depict one embodiment of the sensor device that incorporates Micro Electro Mechanical Systems (MEMS)-based technology.

DETAILED DESCRIPTION OF THE PREFERRED EMBODIMENT

Figure 1:
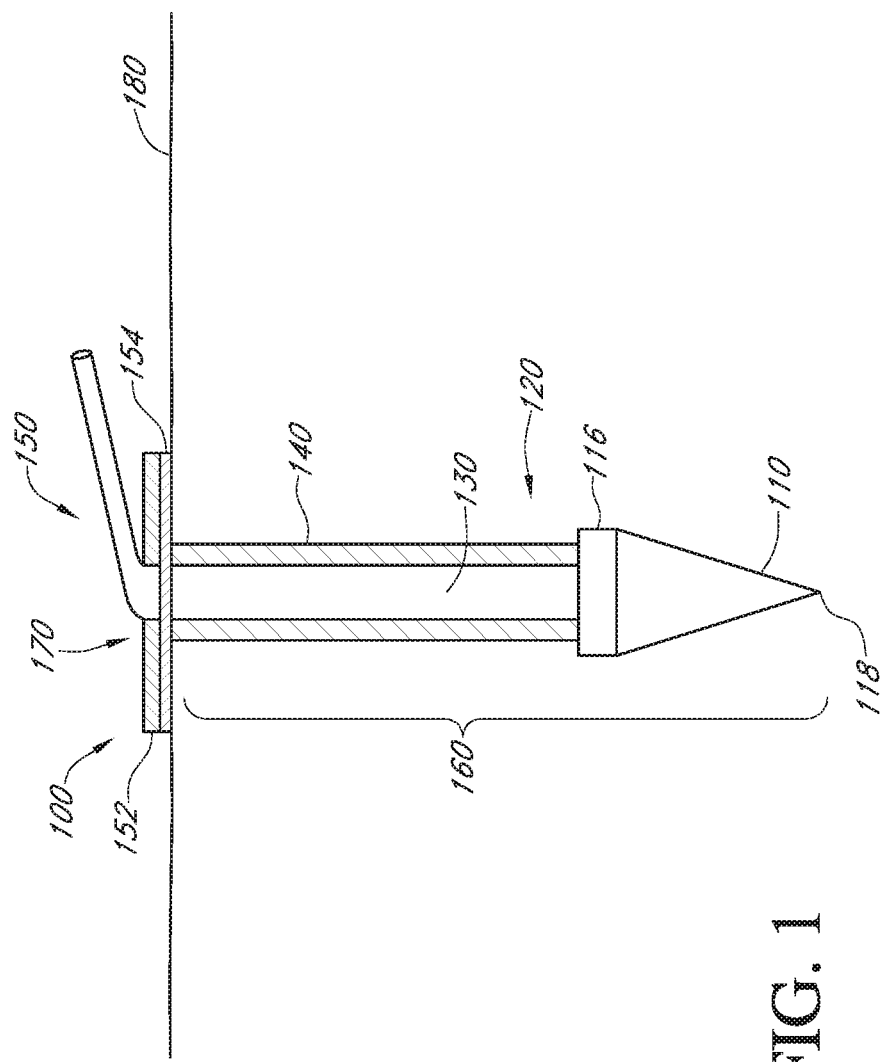
FIG. 1 illustrates a schematic side view of one embodiment of the sensor device.

The following description and examples describe in detail some exemplary embodiments of devices and methods for providing continuous measurement of an analyte concentration. It should be understood that there are numerous variations and modifications of the devices, systems, and methods described herein that are encompassed by the present invention. Accordingly, the description of a certain exemplary embodiment should not be deemed to limit the scope of the present invention.

Definitions

In order to facilitate an understanding of the devices and methods described herein, a number of terms are defined below.

The term "analyte" as used herein is a broad term, and is to be given its ordinary and customary meaning to a person of ordinary skill in the art (and is not to be limited to a special or customized meaning), and refers without limitation to a substance or chemical constituent in a biological fluid (for example, blood, interstitial fluid, cerebral spinal fluid, lymph fluid, urine, sweat, saliva, etc.) that can be analyzed. Analytes can include naturally occurring substances, artificial substances, metabolites, or reaction products. In some embodiments, the analyte for measurement by the sensing regions, devices, and methods is glucose. However, other analytes are contemplated as well, including, but not limited to: acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); glucagon; ketones (e.g., acetone); ephedrine; terbutaline; $O_2$; $CO_2$; potassium; $PCO_2$; $PO_2$; sodium, hematocrit; reactive oxygen species; nitric oxide; diols; pyruvate dehydroxgenase; NADPH oxidase; xanthine oxidase; acyl CoA oxidase; plasma amine oxidase; bilirubin; cholesterol; creatinine; gentisic acid; ibuprofen; L-Dopa; methyl Dopa; salicylate; tetracycline; tolazamide; tolbutamide; human chorionic gonadotropin; anesthetic drugs (e.g., lidocaine); acetyl CoA; intermediaries in the Kreb's cycle (e.g., citrate, cis-aconitate, D-isocitrate, succinate, fumarate; malate, etc.); anti-seizure drugs (e.g., ACTH, lorazepam, carbamezepine, carnitine, Acetazolamide, Phenytoin sodium, depakote, divalproex sodium, tiagabine hydrochloride, levetiracetam, clonazepam, lamotrigine, nitrazepam, primidone, gabapentin, paraldehyde, phenobarbital, carbamazepine, topiramate, clorazepate dipotassium, carbazepine, diazepam, Ethosuximide, Zonisamide); glutamine; cytochrome oxidase, heparin andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alcohol oxidase, alpha 1-antitrypsin, cystic fibrosis, Duchenne/Becker muscular dystrophy, glucose-6- phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; triglycerides; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; glucose-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (e.g., Immunoglobulin M, Immunoglobulin M, IgG adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae*, Myoglobin, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni, Toxoplasma gondii, Trepenoma pallidium, Trypanosoma cruzi/rangeli, vesicular stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins, and hormones naturally occurring in blood or interstitial fluids can also constitute analytes in certain embodiments. The analyte can be naturally present in the biological fluid or endogenous, for example, a metabolic product, a hormone, an antigen, an antibody, and the like. Alternatively, the analyte can be introduced into the body or exogenous, for example, a contrast agent for imaging, a radioisotope, a chemical agent, a fluorocarbon-based synthetic blood, or a drug or pharmaceutical composition, including but not limited to: insulin; ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body can also be analyzed, such as, for example, ascorbic acid, uric acid, dopamine, noradrenaline, 3-methoxytyramine (3MT), 3,4-dihydroxyphenylacetic acid (DOPAC), homovanillic acid (HVA), 5-hydroxytryptamine (5HT), and 5-hydroxyindoleacetic acid (FHIAA).

The phrase "continuously measuring" and like phrases as used herein are broad terms, and are to be given their ordinary and customary meaning to a person of ordinary skill in the art (and are not to be limited to a special or customized meaning), and refer without limitation to the period in which monitoring of analyte concentration is continuously, continually, and or intermittently (but regularly) performed, for example, about every 5 to 10 minutes.

The term "operably connected" and like terms as used herein are broad terms, and are to be given their ordinary and customary meaning to a person of ordinary skill in the art (and are not to be limited to a special or customized meaning), and refer without limitation to one or more components linked to another component(s) in a manner that allows transmission of signals between the components. For example, one or more electrodes can be used to detect the amount of analyte in a sample and convert that information into a signal; the signal can then be transmitted to a circuit. In this case, the electrode is "operably connected" to the electronic circuitry.

The term "host" as used herein is a broad term, and is to be given its ordinary and customary meaning to a person of ordinary skill in the art (and is not to be limited to a special or customized meaning), and refers without limitation to animals (e.g., humans) and plants.

The term "in vivo portion" as used herein is a broad term and is to be given its ordinary and customary meaning to a person of ordinary skill in the art (and is not to be limited to a special or customized meaning), and refers without limitation to the portion of the device (for example, a sensor body, a tissue piercing element, or a sensor unit) adapted for insertion into and/or existence within a living body of a host.

The term "ex vivo portion" as used herein is a broad term and is to be given it ordinary and customary meaning to a person of ordinary skill in the art (and are not to be limited to a special or customized meaning), and refers without limitation to the portion of the device (for example, a mounting unit) adapted to remain and/or exist outside of a living body of a host.

The terms "electrochemically reactive surface", "electroactive surface", and like terms as used herein are broad terms, and are to be given their ordinary and customary meaning to a person of ordinary skill in the art (and are not to be limited to a special or customized meaning), and refer without limitation to the surface of an electrode where an electrochemical reaction takes place. As one example, in a working electrode, $H_2O_2$ (hydrogen peroxide) produced by an enzyme-catalyzed reaction of an analyte being detected reacts and thereby creates a measurable electric current. For example, in the detection of glucose, glucose oxidase produces $H_2O_2$ as a byproduct. The $H_2O_2$ reacts with the surface of the working electrode to produce two protons ($2H^+$), two electrons ($2e^-$), and one molecule of oxygen ($O_2$), which produces the electric current being detected. In the case of the counter electrode, a reducible species, for example, $O_2$ is reduced at the electrode surface in order to balance the current being generated by the working electrode.

The terms "sensing region", "sensor", and like terms as used herein are broad terms, and are to be given their ordinary and customary meaning to a person of ordinary skill in the art (and is not to be limited to a special or customized meaning), and refer without limitation to the region or mechanism of a monitoring device responsible for the detection of a particular analyte.

The terms "raw data stream" and "data stream" as used herein are broad terms, and are to be given their ordinary and customary meaning to a person of ordinary skill in the art (and are not to be limited to a special or customized meaning), and refer without limitation to an analog or digital signal directly related to the measured glucose concentration from the glucose sensor. In one example, the raw data stream is digital data in "counts" converted by an A/D converter from an analog signal (for example, voltage or amps) representative of a glucose concentration. The terms broadly encompass a plurality of time spaced data points from a substantially continuous glucose sensor, which comprises individual measurements taken at time intervals ranging from fractions of a second up to, for example, 1, 2, or 5 minutes or longer.

The term "counts" as used herein is a broad term, and is to be given its ordinary and customary meaning to a person of ordinary skill in the art (and is not to be limited to a special or customized meaning), and refers without limitation to a unit of measurement of a digital signal. In one example, a raw data stream measured in counts is directly related to a voltage (for example, converted by an A/D converter), which is directly related to current from the working electrode. In another example, counter electrode voltage measured in counts is directly related to a voltage.

The phrase "distal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a sensor include a membrane system having a diffusion resistance layer and an enzyme layer. If the sensor is deemed to be the point of reference and the diffusion resistance layer is positioned farther from the sensor than the enzyme layer, then the diffusion resistance layer is more distal to the sensor than the enzyme layer.

The phrase "proximal to" as used herein is a broad term, and is to be given its ordinary and customary meaning to a person of ordinary skill in the art (and is not to be limited to a special or customized meaning), and refers without limitation to the spatial relationship between various elements in comparison to a particular point of reference. For example, some embodiments of a device include a membrane system having a diffusion resistance layer and an enzyme layer. If the sensor is deemed to be the point of reference and the enzyme layer is positioned nearer to the sensor than the diffusion resistance layer, then the enzyme layer is more proximal to the sensor than the diffusion resistance layer.

The terms "membrane system" and "membrane" as used herein are broad terms, and are to be given their ordinary and customary meaning to a person of ordinary skill in the art (and are not to be limited to a special or customized meaning), and refer without limitation to a permeable or semi-permeable membrane that can comprise one or more layers and constructed of materials, which are permeable to oxygen and may or may not be permeable to an analyte of interest. In one example, the membrane system comprises an immobilized glucose oxidase enzyme, which enables an electrochemical reaction to occur to measure a concentration of glucose.

The term "domain" as used herein is a broad term, and is to be given its ordinary and customary meaning to a person of ordinary skill in the art (and is not to be limited to a special or customized meaning), and refers without limitation to regions of a membrane that can be layers, uniform or non-uniform gradients (i.e., anisotropic) or provided as portions of the membrane.

The terms "interferents", "interfering species", and like terms as used herein are broad terms, and are to be given their ordinary and customary meaning to a person of ordinary skill in the art (and are not to be limited to a special or customized meaning), and refer without limitation to effects or species that interfere with the measurement of an analyte of interest in a sensor to produce a signal that does not accurately represent the analyte measurement. In an exemplary electrochemical sensor, interfering species can include compounds with an oxidation potential that overlaps with that of the analyte to be measured.

Overview

The embodiments described herein provide various mechanisms for directly inserting a transcutaneous sensor into a host without the use of a separate applicator or the like, i.e., other than the sensor device itself. Direct press insertion of a transcutaneous sensor (e.g., an electrode) having a wire-like geometry, especially a fine wire, can be technically challenging because of buckling risks associated with the sensor. Direct press insertion of a sensor also presents challenges relating to damage during the insertion process to the membrane disposed on the sensor. Without membrane protection, the membrane can be stripped off from the sensor or be mechanically damaged during the insertion process. The embodiments described herein are designed to overcome the aforementioned challenges by providing miniaturized sensor devices capable of providing structural support (e.g., in the form of mechanical/structural properties such as column strength) for direct insertion of a transcutaneous sensor and capable of protecting the membrane from damage during the insertion process.

FIG. 1 provides a schematic side view of an exemplary embodiment of a transcutaneous sensor device 100 configured to continuously measure analyte concentration (e.g., glucose concentration) in a host to provide a data stream representative of the host's analyte concentration. In the particular embodiment illustrated in FIG. 1, the sensor device 100 comprises an in vivo portion 160 (also referred to as a sensor unit) configured for insertion under the skin of the host and an ex vivo portion 170 configured to remain above the host's skin surface after sensor insertion. The in vivo portion 160 comprises a tissue piercing element 110 configured for piercing the skin 180 of the host and a sensor body 120 comprising a support member 130 that is comprised of one or more electrodes and a membrane 140 disposed over at least a portion of the support member 130. The ex vivo portion 170 comprises a mounting unit 150 that may comprise a sensor electronics unit embedded or detachably attached therein, or alternatively may be configured to operably connect to a separate sensor electronics unit.

In some embodiments, the sensor device may be substantially modular and formed of multiple separate components (e.g., the tissue piercing element, the sensor body, the mounting unit, the sensor electronics unit) that are detachable from each other. In these embodiments, pressure-resistant bonds may be formed between the different components by welding, soldering, or use of adhesives to join the different pieces. In other embodiments, two or more components of the sensor device may be formed as one piece. For example, the tissue piercing element and the sensor body may be fabricated as a single unitary piece. The different components of the transcutaneous sensor device will now be described in greater detail.

Tissue Piercing Element

The tissue piercing element 110 of the sensor device 100 is configured to pierce the skin 180 of the host and to open and define a passage for insertion of the sensor body 120 into a tissue of the host. The skin generally comprises multiple layers, including the epidermis, dermis, and subcutaneous layers. The epidermis comprises a number of layers within its structure including the stratum corneum, which is the outermost layer and is generally from about 10 to 20 microns thick, and the stratum germinativum, which is the deepest layer of the epidermis. While the epidermis generally does not contain blood vessels, it exchanges metabolites by diffusion to and from the dermis. While not wishing to be bound by theory, it is believed that because the stratum germinativum is supported by vascularization for survival, the interstitial fluid at the stratum germinativum sufficiently represents a host's analyte (e.g., glucose) levels. Beneath the epidermis is the dermis, which is from about 1 mm to about 3 mm thick and contains blood vessels, lymphatics, and nerves. The subcutaneous layer lies underneath the dermis and is mostly comprised of fat. The subcutaneous layer serves to insulate the body from temperature extremes. It also contains connective tissue and a small amount of blood vessels.

In some embodiments, the in vivo portion 160 of the sensor device 100 may have a length long enough to allow for at least a portion of the sensor body 120 to reside within the stratum germinativum. This may be desirable in some instances because the epidermis does not contain a substantial number of blood vessels or nerve endings; thus, sensor insertion may be relatively painless, and the host may not experience much bleeding or discomfort from the insertion. In some of these embodiments, the in vivo portion 160 of the sensor device 100 can have a length of from about 0.1 mm to about 1.5 mm, or from about 0.2 mm to about 0.5 mm. In other embodiments, the in vivo portion 160 of the sensor device 100 may have a length that allows for at least a portion of the sensor body 120 to reside in the dermis layer. This may be desirable in some instances because the dermis is well vascularized, as compared to the subcutaneous layer, and thus can provide sufficient analytes (e.g., glucose) for measurement and reduce measurement lags associated with changes of analyte concentrations of a host, such as those that occur after meals. The metabolically active tissue near the outer dermis (and also the stratum germinativum) provides rapid equilibrium of the interstitial fluid with blood. In some of these embodiments, the in vivo portion 160 of the sensor device can have a length of from about 1 mm to about 7 mm, or from about 2 mm to about 6 mm. In still other embodiments, the in vivo portion 160 of the sensor device 100 may have a length that allows for at least a portion of the sensor body 120 to reside in the subcutaneous layer. While not wishing to be bound by theory, it is believed that because the subcutaneous layer serves to insulate the body from temperature extremes, the subcutaneous layer may reduce variations of analyte concentration readings associated with temperature fluctuations. In some of these embodiments, the in vivo portion 160 of the sensor device can have a length of from about 3 mm to about 10 mm, or from about 5 mm to about 7 mm.

Figure 2A:
FIGS. 2A, 2B, 2C, 2D, 2E, 2F, 2G, and 2H illustrate side views of different embodiments of distal tips of the tissue piercing element.
Figure 2B:
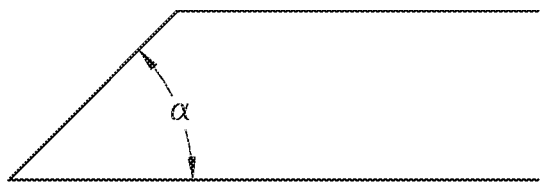
Figure 2C:
Figure 2D:
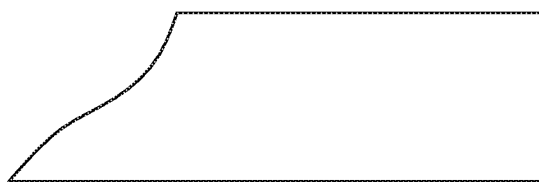
Figure 2E:
Figure 2F:
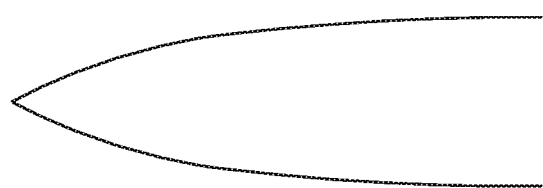
Figure 2G:
Figure 2H:

The tissue piercing element may have any of a variety of geometric shapes and dimensions, including ones that minimize tissue trauma and reduce the force required for skin penetration. For example, in some embodiments, the tissue piercing element may comprise a substantially conically-shaped distal tip, as illustrated in FIGS. 1 and 2A, such that the cross-sectional dimensions (e.g., diameter) of the tissue piercing element tapers to a point 118 at the distal end of the tip, thereby providing a sharpened leading edge configured to facilitate skin penetration. As illustrated in FIG. 2B, in other embodiments, the distal tip of the tissue piercing element may be beveled with a bevel angle α, such as, for example, an angle of from about 5° to about 66°, or from about 10° to about 55°, or from about 40° to about 50°. In further embodiments, one or more surfaces of the tip may be curved, such as illustrated in FIGS. 2C, 2D, 2E, 2F, 2G, 2H, and 3D, so as to facilitate skin penetration when the sensor device is pushed downwards. In some embodiments, a curved surface may be advantageous because it provides the tissue piercing element with a greater cutting surface area than a straight surface, and thus provide a smoother and more controlled insertion of the sensor unit through the skin. Also, a tissue piercing element with a curved surface can or cause less trauma to the pierced tissue than one with a straight surface.

The tissue piercing element of the sensor device is designed to have appropriate flexibility and hardness and sufficient column strength to allow it to remain intact and to prevent it from substantial buckling during insertion of the in vivo portion of the sensor device through the skin of the host. Any of a variety of biocompatible materials having these characteristics may be used to form the tissue piercing element, including, but not limited to, metals, ceramics, semiconductors, organics, polymers, composites, and combinations or mixtures thereof. Metals that may be used include stainless steel (e.g., 18-8 surgical steel), nitinol, gold, silver, nickel, titanium, tantalum, palladium, gold, and combinations or alloys thereof, for example. Polymers that may be used include polycarbonate, polymethacrylic acid, ethylenevinyl acetate, polytetrafluoroethylene (TEFLON®), and polyesters, for example. In some embodiments, the tissue piercing element may serve as a reference electrode and comprise a conductive material, such as a silver-containing material, for example. In certain embodiments, the tissue piercing element has sufficient column strength to allow the user to press the sensor unit through the skin using the force from a thumb or finger, without substantial buckling of the tissue piercing element. Accordingly, the structure of the tissue piercing unit does not fail when it is subjected to resistance (e.g., axial force) associated with the penetration of tissue and skin. In some embodiments, the tissue piercing element may have a column strength capable of withstanding an axial load greater than about 0.5 Newtons, or greater than about 1 Newton, or greater than about 2 Newtons, or greater than about 5 Newtons, or greater than about 10 Newtons, without substantial buckling. Often, an increase in the column thickness of an object will also increase its column strength. In some embodiments, the base 116 of the distal tip may have an outside diameter of from about 0.05 mm to about 1 mm, or from about 0.1 mm to about 0.5 mm, or from about 0.15 mm to about 0.3 mm, to provide the desired column strength for the tissue piercing element.

Some of the tissue piercing elements described herein are configured to protect the membrane of the sensor body. As described elsewhere herein, the membrane may be relatively delicate and thus may be damaged during insertion of the sensor unit into the host. Consequently, any damage sustained by the membrane can affect the sensor device's performance and its ability to function properly. As illustrated in FIG. 1, in some embodiments, one or more portions of the tissue piercing element 110 is formed with a cross-sectional area (along a plane transverse to the longitudinal axis of the tissue piercing element 110) larger than that of the sensor body 120. By having a cross-sectional area larger than that of the sensor body 120, the tissue piercing element 110 of the sensor device 100 is configured to pierce the skin 180 of the host and to open and define a passage for insertion of the sensor body 120 into the tissue. Thus, the risk of a penetration resistance force damaging and/or stripping the membrane 140 off from the rest of the sensor body 120 during the insertion process is minimized. In some embodiments, the largest dimension of the cross section transverse to a longitudinal axis of the tissue piercing element is less than about 0.1 mm, or less than about 0.05 mm, or less than about 0.03 mm.

In some embodiments, one or more layers of one or more polymers and/or bioactive agents, as described elsewhere herein, can be coated onto the tissue piercing element. The use of bioactive agents to coat the surface of the tissue piercing element can provide a release of bioactive agents in the subcutaneous tissue during and/or after insertion of the in vivo portion of the sensor device. In further embodiments, one or more polymer layers can be used to control the release rate of the one or more bioactive agents. Such polymers can include, but are not limited to, parylene, parylene C, parylene N, parylene F, poly(hydroxymethyl-p-xylylene-co-p-xylylene) (PHPX), poly(lactic-co-glycolic acid) (PLGA), polyethylene-co-vinyl acetate (PEVA), Poly-L-lactic acid (PLA), poly N-butyl methacrylate (PBMA), phosphorylcholine, poly(isobutylene-co-styrene), polyoxyethylene (POE), polyglycolide (PGA), (poly(L-lactic acid), poly(amic acid) (PAA, polyethylene glycol (PEG), derivatives of one or more of these polymers, and combinations or mixtures thereof.

In some embodiments, one or more regions of the surface of the tissue piercing element may comprise one or more recessed portions (e.g., cavities, indentations, openings, grooves, channels, etc.) configured to serve as reservoirs or depots for holding bioactive agents. The recessed portions may be formed at any preselected location and have any preselected depth, size, geometrical configuration, and dimensions, in accordance with the intended application. Use of reservoirs or depots can increase the amount of bioactive agents the tissue piercing element is capable of carrying and delivering. In further embodiments, the tissue piercing element may be hollow with a cavity and connected via various passages with one or more openings on its surface, so that bioactive agents can be released from the cavity via the openings. In some embodiments, for example as shown FIGS. 3A and 3B, the tissue piercing element 310 comprises a pocket 312 shaped and dimensioned to support a sensor 314 with a membrane disposed thereon.

In certain embodiments, the in vivo portion of the sensor device is configured to remain substantially stationary within the tissue of the host, so that migration or motion of the sensor body with respect to the surrounding tissue is minimized. Migration or motion can cause inflammation at the sensor implant site due to irritation, and can also cause noise on the sensor signal due to motion-related artifact. Therefore, it can be advantageous to provide an anchoring mechanism that provides support for the in vivo portion of the sensor device to avoid the aforementioned problems. In some embodiments, the tissue piercing element may comprise a surface with one or more regions that are textured. Texturing may roughen the surface of the tissue piercing element and thereby provide a surface contour with a greater surface area than that of a non-textured (e.g., smooth) surface. Accordingly, the amount of bioactive agents, polymers, and/or coatings that the tissue piercing element can carry and be released in situ is increased, as compared to that with a non-textured surface. Furthermore, it is believed that a textured surface may also be advantageous in some instances, because the increased surface area may enhance immobilization of the in vivo portion of the sensor device within the tissue of the host. In certain embodiments, the tissue piercing element may comprise a surface topography with a porous surface (e.g. porous parylene), ridged surface, or the like. In certain embodiments, the anchoring can be provided by prongs, spines, barbs, wings, hooks, a bulbous portion (for example, at the distal end), an S-bend along the tissue piercing element, a gradually changing diameter, combinations thereof, or the like, which can be used alone or in combination to stabilize the sensor within the subcutaneous tissue. For example, in certain embodiments, the tissue piercing element may comprise one or more anchoring members configured to splay outwardly (e.g., in a direction toward a plane perpendicular to the longitudinal axis of the sensor unit) during or after insertion of the sensor unit. Outward deployment of the anchoring member facilitates anchoring of the sensor unit, as it results in the tissue piercing element pressing against the surrounding tissue and thus reduces (or prevents) movement and/or rotation of the sensor unit. In some embodiments, the anchoring members are formed of a shape memory material, such as nitinol, which can be configured to transform from a martensitic state to an austenitic state at a specific temperature (e.g., room temperature or body temperature). In the martensitic state, the anchoring members are ductile and in a contracted configuration. In the austenitic state, the anchoring members deploy to form a larger predetermined shape while becoming more rigid. While nitinol is described herein as an example of a shape memory material that may be chosen to form the anchoring member, it should be understood that other like materials (e.g., shape memory material) may also be used.

The tissue piercing element of the sensor device may be introduced subcutaneously at any of a variety of angles with respect to the mounting surface, i.e., the bottom surface of the mounting unit, and thus the skin surface. For example, in some embodiments, the distal tip of the tissue piercing element may extend substantially perpendicular to the mounting surface, but in other embodiments, the distal tip may extend at an angle with respect to the mounting surface of about 15°, 20°, 30°, 40°, 45°, 60°, 75°, 80°, 90°, 105°, 100°, 120°, 135°, 140°, 150°, 160°, or 165° degrees, for example.

In alternative embodiments, to provide protection of the membrane during insertion of the sensor device, the sensor body may be embedded or encapsulated in a needle formed of a biodegradable material. Following insertion, the needle gradually biodegrades, leaving behind the sensor body which can then be activated. Any of a variety of biodegradable materials (e.g., a non-interfering carbohydrate) can be used. In some embodiments, the biodegradable material may include a certain concentration of an analyte to be measured, so that an initial calibration point of the sensor device can be provided.

Sensor Body

Referring back to the embodiment of FIG. 1, in one embodiment, the sensor device 100 comprises a sensor body 120 that includes one or more electrodes configured to continuously measure blood analyte concentrations in a host. The sensor body 120 may also include a reference electrode (and/or a counter electrode) against which the working electrode may be referenced. Alternatively or additionally, the tissue piercing element 110 may also be employed as a reference electrode. The working electrode may comprise a conductive material, such as, for example, platinum, platinum-iridium, gold, palladium, iridium, graphite, carbon, a conductive polymer, an alloy, and/or the like, suitable to provide electroactive surfaces. The reference electrode may comprise a conductive material, such as a silver-containing material, for example. A membrane, as described in greater detail elsewhere herein, is disposed over at least a portion of the electrodes.

Figure 4:
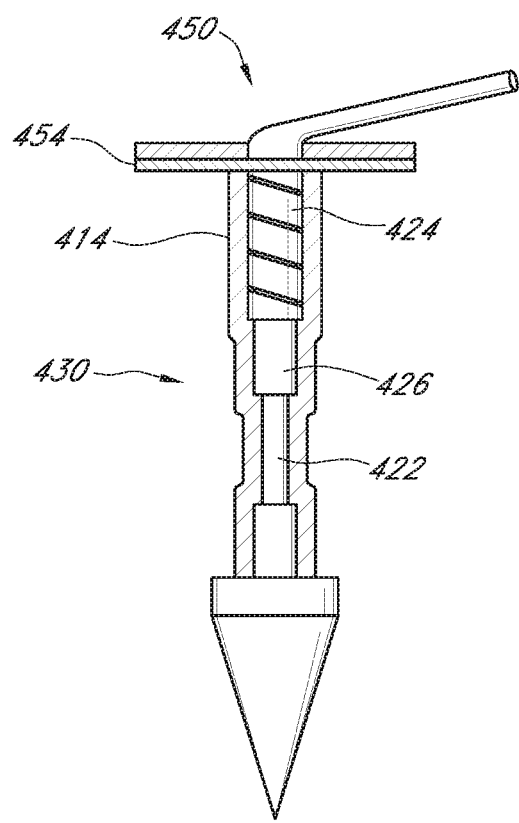
FIG. 4 illustrates an expanded cutaway view of a sensor comprising a working electrode with a reference electrode wound around thereon.

As described elsewhere herein, the membrane 140 of the sensor body 120, if not protected, can become damaged during insertion, which in turn can affect the sensor device's performance and its ability to function properly. FIG. 1 illustrates one embodiment that is configured to provide protection of the membrane 140. In this particular embodiment, the sensor body 120 includes a support member 130 that extends from the proximal end of the tissue engaging element 110 to the mounting unit 150. The support member 130 can be comprised of both a working electrode and a reference electrode. In an alternative embodiment, as illustrated in FIG. 4, the support member 430 comprises the working electrode 422, and a separate reference electrode 424 is helically wound around the working electrode 422. A mounting unit 450 is provided with an adhesive material or adhesive layer 454 (e.g., an adhesive pad) disposed on the mounting unit's 450 lower surface and may also include a releasable backing layer. A membrane 414 is disposed on the working electrode 422 and the reference electrode 424. In this alternative embodiment, the helical winding arrangement of the reference electrode 424 may provide additional column strength to at least a portion of the support member 430 and ensure that the support member 430 projects at a preselected angle with respect to the mounting surface. In still another alternative embodiment, the support member may not comprise any electrode. Instead, a working electrode (and optionally a reference electrode) may be configured to encircle, encompass, helically wind around, or otherwise lie substantially juxtapositioned to the support member. An insulator can be provided between the support member (if conductive), the working electrode, and the reference electrode, to provide electrical insulation.

In alternative embodiments, the sensor device may comprise two or more sensor bodies. For example, one sensor body may be associated with the working electrode and another sensor body may be associated with the reference electrode. The plurality of sensor bodies may be joined to a single tissue piercing element, or alternatively, formed as independent structures, i.e., with each sensor body being associated with a different tissue piercing element. In embodiments wherein the plurality of sensor bodies are formed as independent structures, the individual sensor bodies may be inserted in proximal, but separate, locations. With this arrangement, the separation of the working and reference electrodes may provide electrochemical stability.

The support member may be formed of any of a variety of biocompatible materials capable of providing appropriate flexibility and hardness and sufficient column strength, such that the support member can be pushed through the skin of the host without substantial buckling. In certain embodiments, the support member has sufficient column strength to allow the user to press the sensor unit through the skin using the force from a thumb or finger, without substantial buckling of the support member. Accordingly, the structure of the support member does not fail when it is subjected to resistance (e.g., axial force) associated with the penetration of tissue and skin. Materials that may be used to form the support member include, but are not limited to, stainless steel, titanium, tantalum, platinum, platinum-iridium, iridium, certain polymers, and/or the like. In certain embodiments, the support member may have a column strength capable of withstanding an axial load greater than about 0.5 Newtons, or greater than about 1 Newton, or greater than about 1.5 Newtons, or greater than about 2 Newtons, or greater than about 5 Newtons, or greater than about 10 Newtons, without substantial buckling.

While the support members 130, 430 illustrated in FIGS. 1 and 4 are formed with a circular cross section, in other embodiments the cross section of the support member may have any of a variety of cross-sectional shapes, such as oval, square, rectangular, triangular, polyhedral, star-shaped, C-shaped, T-shaped, X-shaped, Y-Shaped, irregular, or the like, for example. In certain embodiments, the support member may be formed of a conductive core (e.g., a conductive wire) covered by one or more conducting layers (and may include intervening insulating layers provided for electrical isolation). The conductive layers can be comprised of any suitable material; however, in certain embodiments and depending upon the fabrication methods, it can be desirable to employ a conductive layer comprising conductive particles (i.e., particles of a conductive material) in a polymer or other binder.

Similar to the tissue piercing element, some of the support members described herein may comprise one or more recessed portions (e.g., cavities, indentations, openings, grooves, channels, etc.) configured to serve as reservoirs or depots for holding bioactive agents. The recessed portions may be formed at any preselected location and have any preselected depth, size, geometrical configuration, and dimensions, in accordance with the intended application. Use of reservoirs or depots can increase the amount of bioactive agents the support member is capable of carrying and delivering. In further embodiments, the support member may be hollow with a cavity and formed with one or more openings on its surface, so that bioactive agents can be released from the cavity via the openings.

Similar to the tissue piercing element, some of the support members described herein may comprise a surface with one or more regions that are textured to provide a surface contour with a greater surface area than that of a non-textured (e.g., smooth) surface. In certain embodiments, the support member may comprise a surface topography with a porous surface (e.g. porous parylene), ridged surface, or the like. Additionally or alternatively, the support member can be provided with prongs, spines, barbs, wings, hooks, a bulbous portion (for example, at the distal end), an S-bend along the tissue piercing element, a gradually changing diameter, combinations thereof, or the like, which can be used alone or in combination to stabilize the sensor within the subcutaneous tissue.

In certain embodiments, a membrane is disposed over at least a portion of the support member and the sensor. As illustrated in the FIG. 1, in some embodiments, the sensor body 120 is configured to have a smaller cross-sectional area than that of the tissue piercing element 110, such that the membrane 140 of the sensor body 120 does not project radially beyond the largest perimeter (e.g., circumference) of the tissue piercing element 110. Thus, the membrane 140 is protected during insertion of the in vivo portion 160 of the sensor device 100. In some embodiments, the largest dimension of the cross section transverse to a longitudinal axis of the sensor body 120 is less than about 0.05 mm, or less than about 0.04 mm, or less than about 0.025 mm.

Figure 3A:
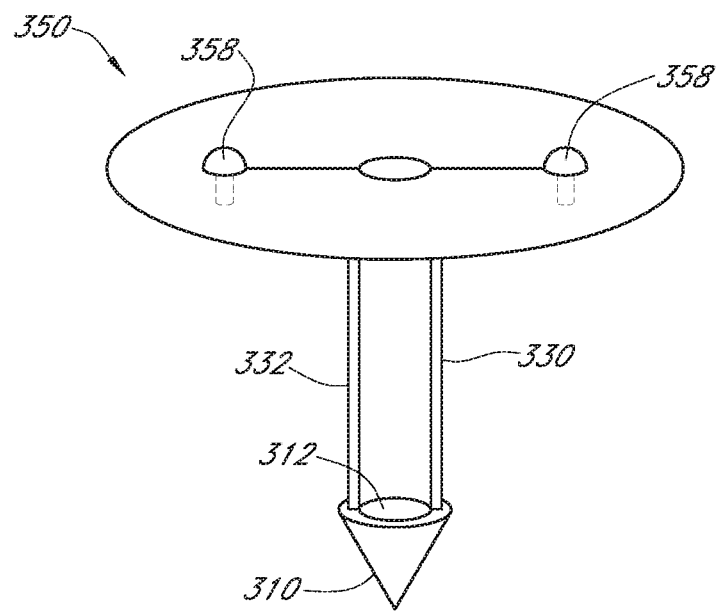
FIG. 3A illustrates a perspective view of another embodiment of the sensor device without a sensor embedded therein.
Figure 3B:
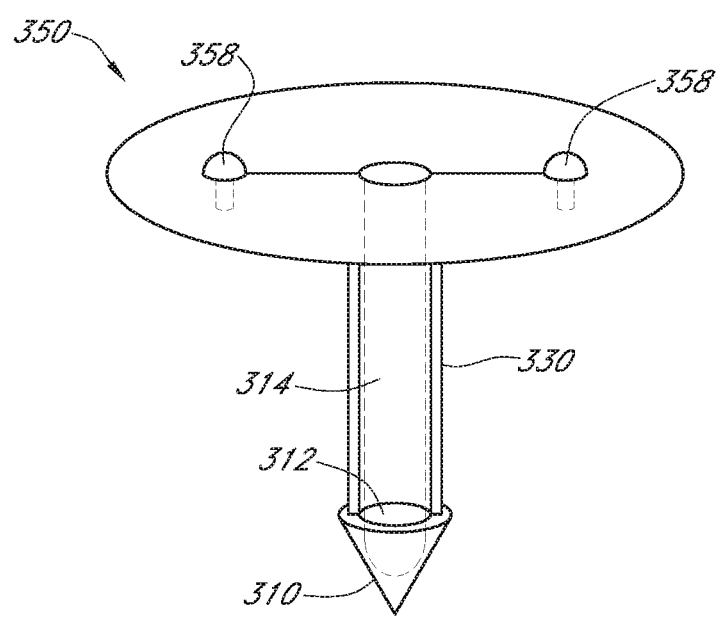
FIG. 3B illustrates a perspective view of the embodiment of FIG. 3A with a sensor embedded therein.
Figure 3C:
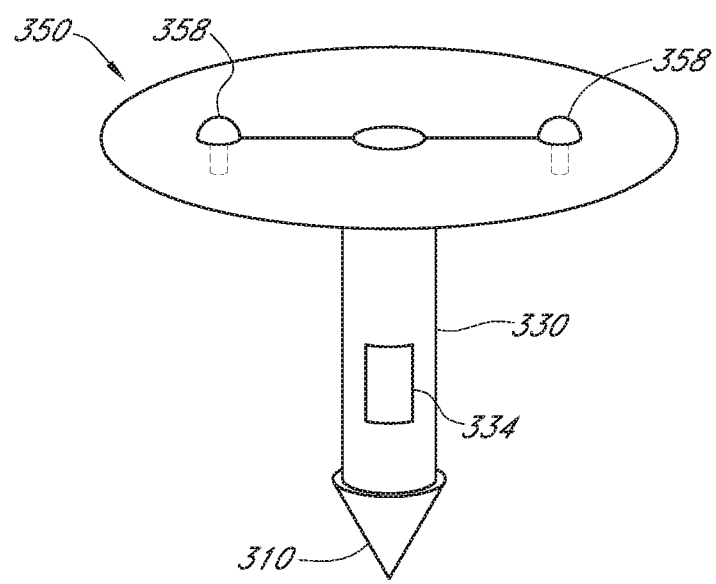
FIG. 3C illustrates a perspective view of another embodiment of the sensor device.
Figure 3D:
FIG. 3D illustrates a side view of another embodiment of the tissue piercing element.

While FIG. 1 illustrates one configuration for providing membrane protection, other sensor body configurations may also be used. For example, some of the sensor bodies described herein may include a support member 330 configured to partially surround a sensor, as illustrated in FIGS. 3A and 3B, or configured to substantially surround a sensor, as illustrated in FIG. 3C. Unlike other embodiments described elsewhere herein, in the embodiments illustrated in FIGS. 3A, 3B, and 3C, the support member 330 does not comprise a working electrode. Rather, one or more working electrodes are arranged as pieces distinct from the support member 330. In some embodiments, the support member 330 may also serve as a reference electrode.

In the embodiment illustrated in FIG. 3A, the support member 330 comprises a longitudinal recess 332 configured to at least partially accommodate a sensor (e.g., a working electrode with a membrane disposed thereon). In some embodiments, the longitudinal recess may have a length corresponding to less than about 90% of the length of the support member 330, or less than about 75%, or less than about 50%, or less than about 33%, or less than about 25%. In other embodiments, the longitudinal recess may extend substantially across the entire length of the support member 330, as illustrated in FIG. 3B. In certain embodiments, the support member 330 may surround more than about 10% of the outer perimeter (e.g., circumference) of the sensor, or more than about 25%, or more than about 33%, or more than about 50%, or more than about 75%.

As illustrated in FIG. 3C, in some embodiments wherein the sensor (e.g., the working electrode) is substantially surrounded by the support member 330, the support member 330 may be provided with one or more window portions 334 (i.e., openings or slots extending through the wall thickness of the support member 330) that exposes certain portions of the electrode to biological fluid (e.g., interstitial fluid) and thus allow biological fluid to diffuse toward and contact the working electrode's electroactive surface and the membrane disposed thereon. In this embodiment, the working electrode and the membrane disposed thereon are essentially housed within the support member 330 and are thus protected during packing, handling, and/or insertion of the device. The window portions 334 may have any of a variety of shapes and dimensions. For example, in some embodiments, the window portions may be formed to have a circular or substantially circular shape, but in other embodiments, the electrode may be formed with a shape resembling an ellipse, a polygon (e.g., triangle, square, rectangle, parallelogram, trapezoid, pentagon, hexagon, octagon), or the like. In certain embodiments, the windows portions may comprise sections that extend around the perimeter of the longitudinal cross section of the support member. For example, the support member may be made by using a hypo-tube with window portions cut out in a spiral configuration, by ablation, etching, or other like techniques.

Figure 5A:
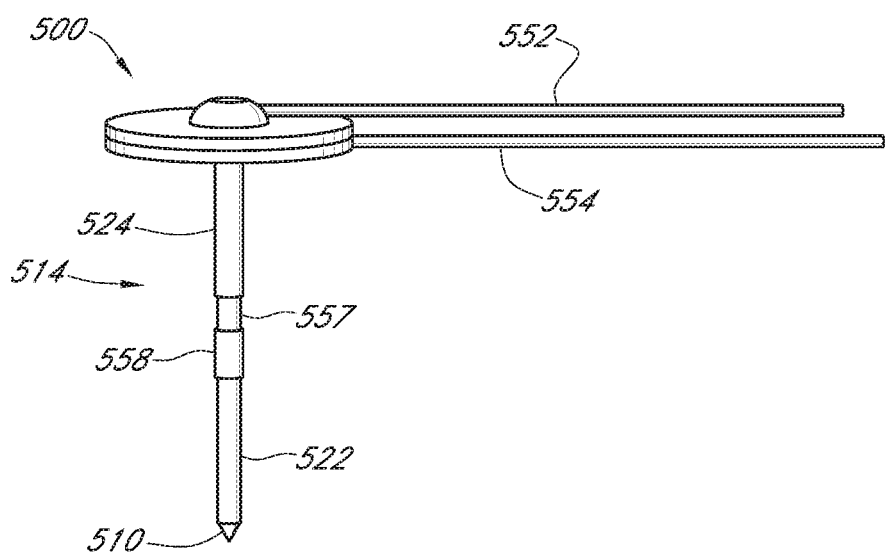
FIG. 5A illustrates a perspective view of another embodiment of the sensor device.
Figure 5B:
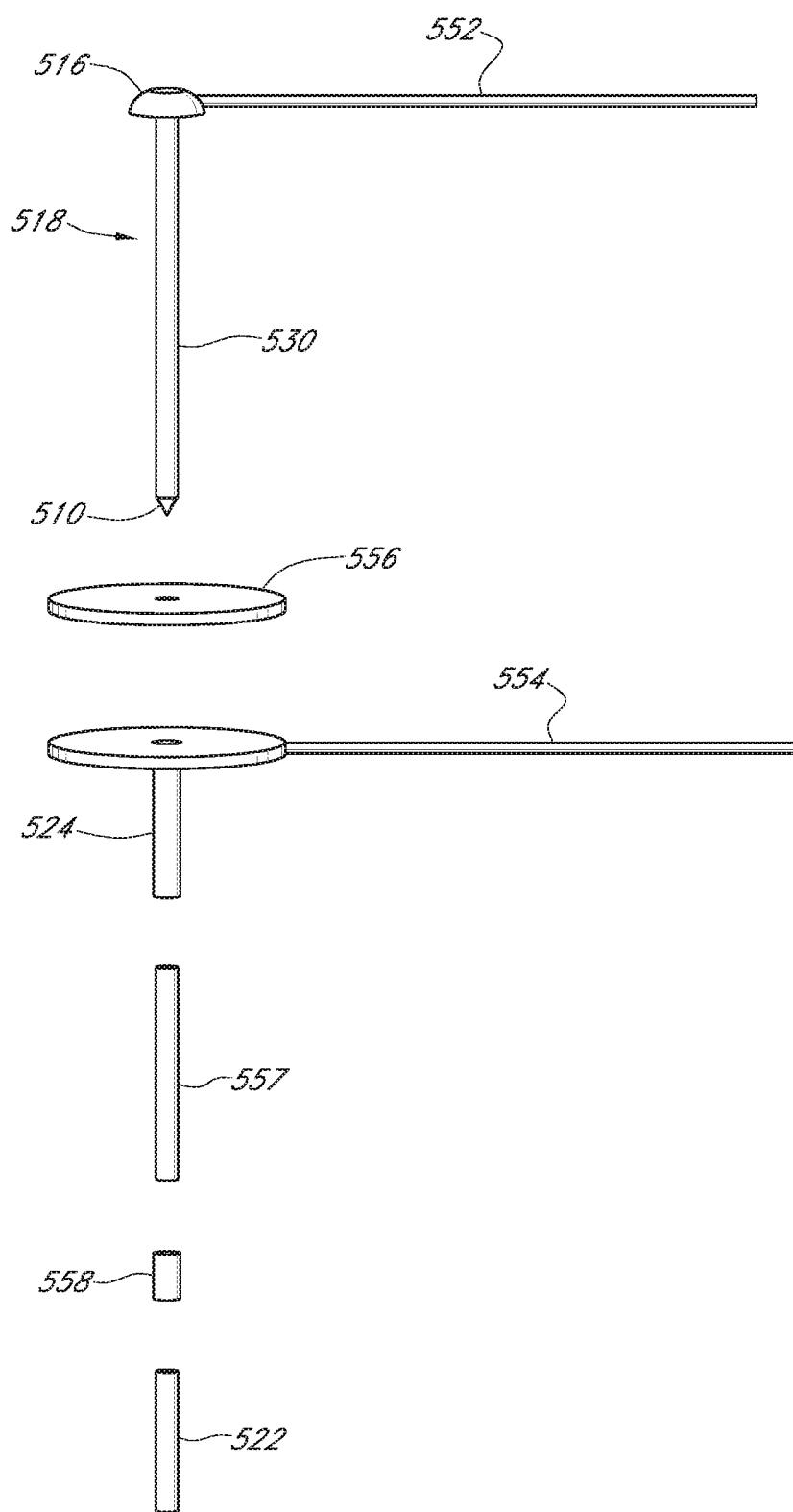
FIG. 5B illustrates an exploded perspective view of the embodiment of FIG. 5A.

FIG. 5A is a perspective view of one embodiment of a sensor device 500 with wires 552, 554 extending therefrom for connecting electrodes 522, 524 with the sensor electronics unit. FIG. 5B is an exploded perspective view of the embodiment illustrated in FIG. 5A, showing the tissue piercing element 510 and the support member 530 formed as a unitary piece as a sensor unit formed of a conductive material. The sensor body in this embodiment comprises the working electrode 522 and the reference electrode 524. A first insulator 556 is provided for electrically insulating the head 516 of the sensor unit 514 from the reference electrode 524. The reference electrode 524 is associated with a wire 554 for connecting the reference electrode 524 to the sensor electronics unit 590. A second insulator 557 is provided that is configured to be disposed between the support member 530 and the reference electrode 524 to provide electrical insulation therebetween. A third insulator 558 is provided for electrically insulating the reference electrode 524 from the working electrode 522, which is located most distal from the sensor unit head 516 in this particular embodiment. Because the support member 530 is formed of a conductive material, it provides an electrical connection between the working electrode 522 and the sensor unit head 516, which is connected to the sensor electronics unit 590 via a wire 552.

As shown in FIG. 5C, in some embodiments, the sensor device 500 may comprise a plurality of sensor units 522, 524 brought together by a mounting unit 550. In further embodiments, the plurality of sensor units may include a first sensor unit associated with a working electrode and a second sensor unit associated with a reference electrode. Alternatively, both the first and second sensor units may each comprise a working and reference electrode.

Any of a variety of electrodes can be employed for the sensor device. For example, referring back to FIG. 4, in one embodiment, the support member 430 may comprise a working electrode comprising an electroactive surface portion 422 and a separate reference electrode 424 helically wound around the working electrode. In this particular embodiment, an insulator 426 is disposed between the working electrode (i.e., the support member 430) and the reference electrode 424, to provide electrical insulation therebetween. In should be understood that in some embodiments, the electrodes may form the support member of the sensor body, in part or in whole, but in other embodiments, the electrodes may be elements that are distinct from the support member.

Figure 7A:
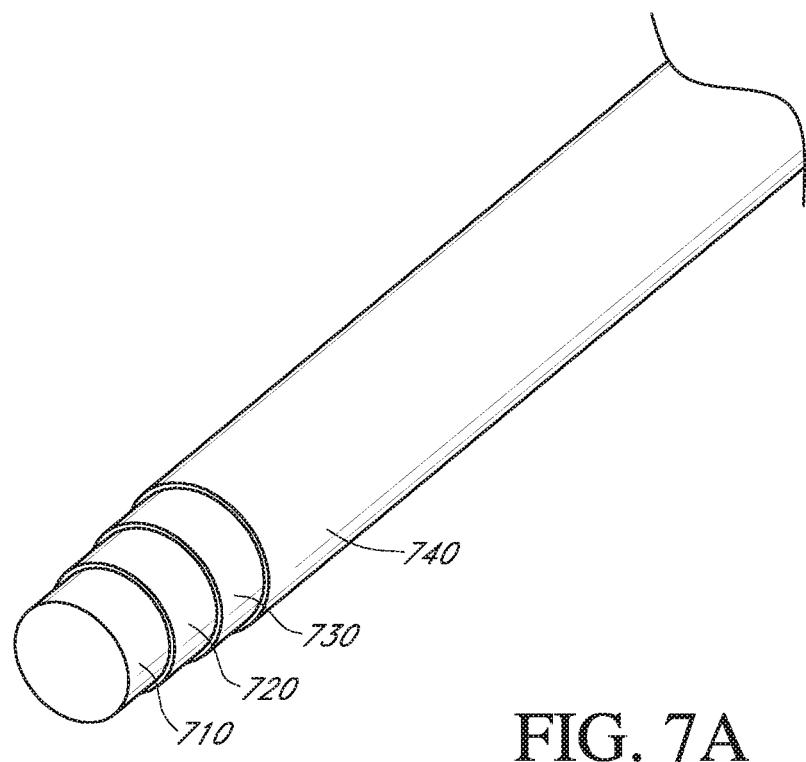
FIG. 7A illustrates one embodiment of the sensor.
Figure 7B:
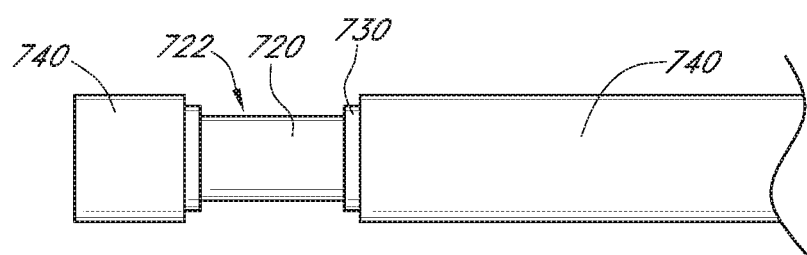
FIG. 7B illustrates the embodiment of FIG. 7A after it has undergone an ablation treatment.

FIG. 7A illustrates one embodiment of an electrode comprising a conductive core 710, a first layer 720 that at least partially surrounds the core 710, a second layer 730 that at least partially surrounds the first layer 720, and a third layer 740 that at least partially surrounds the second layer 730. These layers, which collectively form an elongated body, can be deposited onto the conductive core by any of a variety of techniques, such as, for example, by employing dip coating, plating, extrusion, or spray coating processes. In some embodiments, the first layer 720 can comprise a conductive material, such as, for example, platinum, platinum-iridium, gold, palladium, iridium, graphite, carbon, a conductive polymer, an alloy, and/or the like, configured to provide suitable electroactive surfaces for one or more working electrodes. In certain embodiments, the second layer 730 can correspond to an insulator and comprise an insulating material, such as a non-conductive (e.g., dielectric) polymer (e.g., polyurethane, polyimide, or parylene). In some embodiments, the third layer 740 can correspond to a reference electrode and comprise a conductive material, such as, a silver-containing material, including, but not limited to, a polymer-based conducting mixture. FIG. 7B illustrates one embodiment of the electrode of FIG. 7A, after it has undergone laser ablation treatment. As shown, a window region 722 is formed when the ablation removes the second and third layers 730, 740, to expose an electroactive surface of the first conductive layer 720, wherein the exposed electroactive surface of the first conductive layer 720 correspond to a working electrode.

Figure 7C:
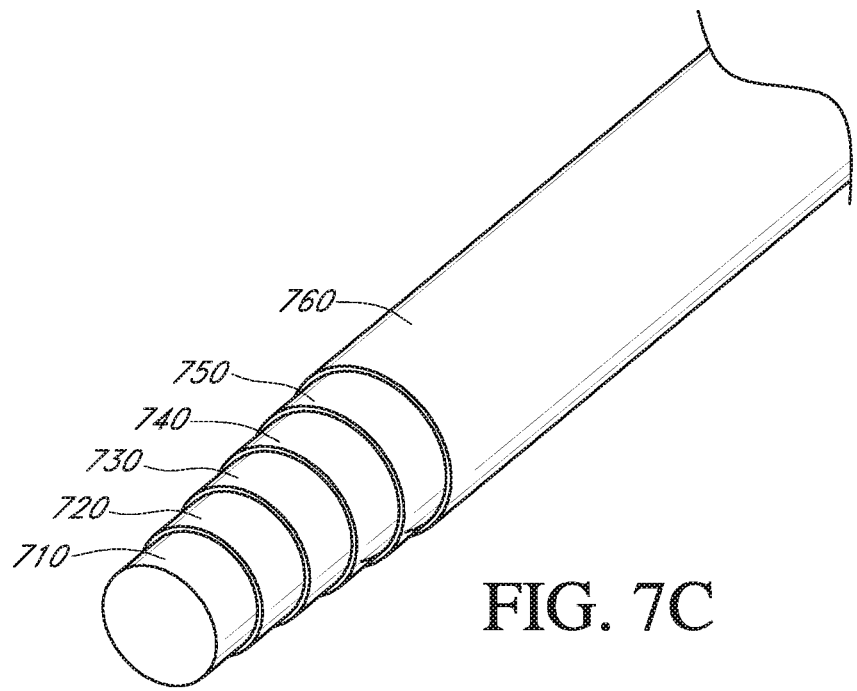
FIG. 7C illustrates another embodiment of the sensor.
Figure 7D:
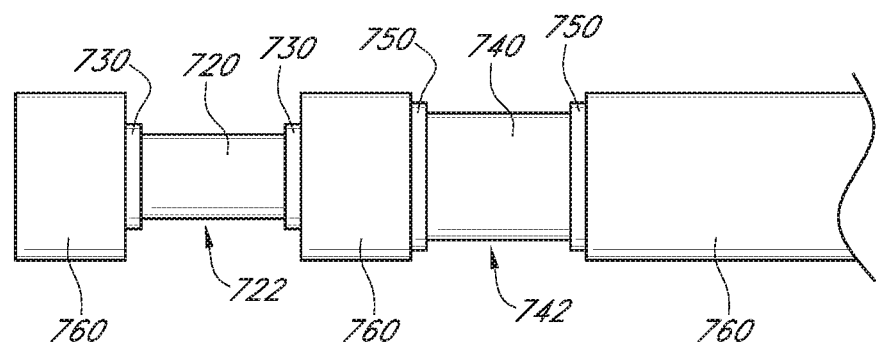
FIG. 7D illustrates the embodiment of FIG. 7C after it has undergone an ablation treatment.

FIG. 7C illustrates another embodiment of an electrode. In this embodiment, in addition to an conductive core 710, a first layer 720, a second layer 730, and a third layer 740, the electrode further comprises a fourth layer 750 and a fifth layer 770. In a further embodiment, the first layer 720 and the second layer 730 can be formed of a conductive material and an insulating material, respectively, similar to those described in the embodiment of FIG. 7A. However, in this particular embodiment, the third layer 740 can be configured to provide the sensor with a second working electrode, in addition to the first working electrode provided by the first layer 720. In this particular embodiment, the fourth layer 750 can comprise an insulating material and provide insulation between the third layer 740 and the fifth layer 760, which can correspond to a reference electrode and comprise the aforementioned silver-containing material. It is contemplated that other similar embodiments are possible. For example, in alternative embodiments, the electrode can have 6, 7, 8, 9, 10, or more layers, each of which can be formed of conductive or non-conductive material. FIG. 7D illustrates one embodiment of the electrode of FIG. 7C, after it has undergone laser ablation treatment. Here, two window regions, a first window region 722 and a second window region 742, are formed, with each window region having a different depth and corresponding to a working electrode distinct from the other.

Membrane System

The membrane systems described herein can be utilized with any of the sensors (e.g., electrodes) described elsewhere herein for measuring analyte levels in a biological fluid, such as sensors for monitoring glucose levels for individuals having diabetes. In some embodiments, the analyte-measuring sensor is a continuous sensor. Although some of the description that follows is directed at glucose-measuring devices, the membrane systems described herein are not limited to use in devices that measure or monitor glucose. Rather, these membrane systems are suitable for use in any of a variety of devices, including, for example, devices that detect and quantify other analytes present in biological fluids (e.g., cholesterol, amino acids, alcohol, galactose, and lactate).

It should be understood that any of the layers described herein, e.g., the electrode, interference, enzyme, or diffusion resistance layer, may be omitted. In addition, it should be understood the membrane system can have any of a variety of layer arrangements, with some arrangements having more or less layers than other arrangements. For example, in some embodiments, the membrane system can comprise one interference layer, one enzyme layer, and two diffusion resistance layers, but in other embodiments, the membrane system can comprise one electrode layer, one enzyme layer, and one diffusion resistance layer.

In some embodiments, one or more layers of the membrane system can be formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyamides, polyimides, polystyrenes, polyurethanes, cellulosic polymers, poly(ethylene oxide), poly(propylene oxide) and copolymers and blends thereof, polysulfones and block copolymers thereof including, for example, di-block, tri-block, alternating, random and graft copolymers.

In some embodiments, one or more layers of the membrane system are formed from a silicone polymer. In further embodiments, the silicone composition can have molecular weight of from about 50,000 to about 800,000 g/mol. It has been found that having the polymers formed with this molecular weight range facilitates the preparation of cross-linked membranes that provide the strength, tear resistance, stability, and toughness advantageous for use in vivo.

In some embodiments, the silicone polymer is a liquid silicone rubber that may be vulcanized using a metal—(e.g., platinum), peroxide-, heat-, ultraviolet-, or other radiation-catalyzed process. In some embodiments, the silicone polymer is a dimethyl- and methylhydrogen-siloxane copolymer. In some embodiments, the copolymer has vinyl substituents. In some embodiments, commercially available silicone polymers can be used. For example, commercially available silicone polymer precursor compositions can be used to prepare the blends, such as described below. In one embodiment, MED-4840 available from NUSIL® Technology LLC is used as a precursor to the silicone polymer used in the blend. MED-4840 consists of a 2-part silicone elastomer precursor including vinyl-functionalized dimethyl- and methylhydrogen-siloxane copolymers, amorphous silica, a platinum catalyst, a crosslinker, and an inhibitor. The two components can be mixed together and heated to initiate vulcanization, thereby forming an elastomeric solid material. Other suitable silicone polymer precursor systems include, but are not limited to, MED-2174 peroxide-cured liquid silicone rubber available from NUSIL® Technology LLC, SILASTIC® MDX4-4210 platinum-cured biomedical grade elastomer available from DOW CORNING®, and Implant Grade Liquid Silicone Polymer (durometers 10-50) available from Applied Silicone Corporation.

In some embodiments, one or more layer of the membrane system is formed from a blend of a silicone polymer and a hydrophilic polymer. By "hydrophilic polymer", it is meant that the polymer has a substantially hydrophilic domain in which aqueous substances can easily dissolve. It has been found that use of such a blend may provide high oxygen solubility and allow for the transport of glucose or other such water-soluble molecules (for example, drugs) through the membrane. In one embodiment, the hydrophilic polymer comprises both a hydrophilic domain and a partially hydrophobic domain (e.g., a copolymer), whereby the partially hydrophobic domain facilitates the blending of the hydrophilic polymer with the hydrophobic silicone polymer. In one embodiment, the hydrophobic domain is itself a polymer (i.e., a polymeric hydrophobic domain). For example, in one embodiment, the hydrophobic domain is not a simple molecular head group but is rather polymeric.

The silicone polymer for use in the silicone/hydrophilic polymer blend can be any suitable silicone polymer, include those described above. The hydrophilic polymer for use in the silicone/hydrophilic polymer blend can be any suitable hydrophilic polymer, including but not limited to components such as polyvinylpyrrolidone (PVP), polyhydroxyethyl methacrylate, polyvinylalcohol, polyacrylic acid, polyethers such as polyethylene glycol or polypropylene oxide, and copolymers thereof, including, for example, di-block, tri-block, alternating, random, comb, star, dendritic, and graft copolymers (block copolymers are discussed in U.S. Pat. Nos. 4,803,243 and 4,686,044). In one embodiment, the hydrophilic polymer is a copolymer of poly(ethylene oxide) (PEO) and poly(propylene oxide) (PPO), such as PEO-PPO diblock copolymers, PPO-PEO-PPO triblock copolymers, PEO-PPO-PEO triblock copolymers, alternating block copolymers of PEO-PPO, random copolymers of ethylene oxide and propylene oxide, and blends thereof, for example. In some embodiments, the copolymers can be optionally substituted with hydroxy substituents. Commercially available examples of PEO and PPO copolymers include the PLURONIC® brand of polymers available from BASF®. Some PLURONIC® polymers are triblock copolymers of poly(ethylene oxide)-poly(propylene oxide)-poly(ethylene oxide) having the general molecular structure:

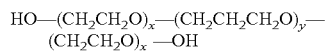

wherein the repeat units x and y vary among various PLURONIC® products. The poly(ethylene oxide) blocks act as a hydrophilic domain allowing the dissolution of aqueous agents in the polymer. The poly(propylene oxide) block acts as a hydrophobic domain facilitating the blending of the PLURONIC® polymer with a silicone polymer. In one embodiment, PLURONIC® F-127 is used having x of approximately 100 and y of approximately 65. The molecular weight of PLURONIC® F-127 is approximately 12,600 g/mol as reported by the manufacture. Other PLURONIC® polymers include PPO-PEO-PPO triblock copolymers (e.g., PLURONIC® R products). Other suitable commercial polymers include, but are not limited to, SYNPERONICS® products available from UNIQEMA®.

The membrane system of some embodiments can comprise at least one polymer containing a surface-active group. The term "surface-active group" and "surface-active end group" as used herein are broad terms and are used in their ordinary sense, including, without limitation, surface-active oligomers or other surface-active moieties having surface-active properties, such as alkyl groups, which are inclined to migrate towards a surface of a membrane formed thereof. In some embodiments, the surface-active group-containing polymer is a surface-active end group-containing polymer. In some of these embodiments, the surface-active end group-containing polymer is a polymer having covalently bonded surface-active end groups. However, it is contemplated that other surface-active group-containing polymers may also be used and can be formed by modification of fully-reacted base polymers via the grafting of side chain structures, surface treatments or coatings applied after membrane fabrication (e.g., via surface-modifying additives), blending of a surface-modifying additive to a base polymer before membrane fabrication, immobilization of the surface-active-group-containing soft segments by physical entrainment during synthesis, or the like.

Base polymers useful for certain embodiments can include any linear or branched polymer on the backbone structure of the polymer. Suitable base polymers can include, but are not limited to, epoxies, polyolefins, polysiloxanes, polyethers, acrylics, polyesters, carbonates, and polyurethanes, wherein polyurethanes can include polyurethane copolymers such as polyether-urethane-urea, polycarbonate-urethane, polyether-urethane, silicone-polyether-urethane, silicone-polycarbonate-urethane, polyester-urethane, and the like. In some embodiments, base polymers can be selected for their bulk properties, such as, but not limited to, tensile strength, flex life, modulus, and the like. For example, polyurethanes are known to be relatively strong and to provide numerous reactive pathways, which properties may be advantageous as bulk properties for a membrane layer of the continuous sensor.

In some embodiments, a base polymer synthesized to have hydrophilic segments can be used to form at least a portion of the membrane system. For example, a linear base polymer including biocompatible segmented block polyurethane copolymers comprising hard and soft segments can be used. It is contemplated that polyisocyanates can be used for the preparation of the hard segments of the copolymer and may be aromatic or aliphatic diisocyanates. The soft segments used in the preparation of the polyurethane can be derived from a polyfunctional aliphatic polyol, a polyfunctional aliphatic or aromatic amine, or the like that can be useful for creating permeability of the analyte (e.g., glucose) therethrough, and can include, for example, polyvinyl acetate (PVA), poly(ethylene glycol) (PEG), polyacrylamide, acetates, polyethylene oxide (PEO), polyethylacrylate (PEA), polyvinylpyrrolidone (PVP), and variations thereof (e.g., PVP vinyl acetate).

Alternatively, in some embodiments, the membrane system can comprise a combination of a base polymer (e.g., polyurethane) and one or more hydrophilic polymers, such as, PVA, PEG, polyacrylamide, acetates, PEO, PEA, PVP, and variations thereof (e.g., PVP vinyl acetate), as a physical blend or admixture, wherein each polymer maintains its unique chemical nature. It is contemplated that any of a variety of combination of polymers can be used to yield a blend with desired glucose, oxygen, and interference permeability properties. For example, in some embodiments, the membrane can comprise a mixture or blend of a polycarbonate-urethane base polymer and PVP, but in other embodiments, a blend of a polyurethane, or another base polymer, and one or more hydrophilic polymers can be used instead. In some of the embodiments involving use of PVP, the PVP portion of the polymer blend can comprise from about 5% to about 50% by weight of the polymer blend, or from about 15% to 20%, or from about 25% to 40%. It is contemplated that PVP of various molecular weights may be used. For example, in some embodiments, the molecular weight of the PVP used can be from about 25,000 daltons to about 5,000,000 daltons, or from about 50,000 daltons to about 2,000,000 daltons, or from 6,000,000 daltons to about 10,000,000 daltons.

Coating solutions that include at least two surface-active group-containing polymers can be made using any of the methods of forming polymer blends known in the art. In one exemplary embodiment, a solution of a polyurethane containing silicone end groups is mixed with a solution of a polyurethane containing fluorine end groups (e.g., wherein the solutions include the polymer dissolved in a suitable solvent such as acetone, ethyl alcohol, DMAC, THF, 2-butanone, and the like). The mixture can then be coated onto the surface of the elongated conductive body using the coating process described elsewhere herein. The coating can then be cured under high temperature (e.g., about 50-150° C.), as the elongated conductive body is advanced through the curing station.

Some amount of cross-linking agent can also be included in the mixture to induce cross-linking between polymer molecules. Non-limiting examples of suitable cross-linking agents include isocyanate, carbodiimide, gluteraldehyde or other aldehydes, epoxy, acrylates, free-radical based agents, ethylene glycol diglycidyl ether (EGDE), poly(ethylene glycol) diglycidyl ether (PEGDE), or dicumyl peroxide (DCP). In one embodiment, from about 0.1% to about 15% w/w of cross-linking agent is added relative to the total dry weights of cross-linking agent and polymers added when blending the ingredients (in one example, about 1% to about 10%). During the curing process, substantially all of the cross-linking agent is believed to react, leaving substantially no detectable unreacted cross-linking agent in the final film.

Figure 6:
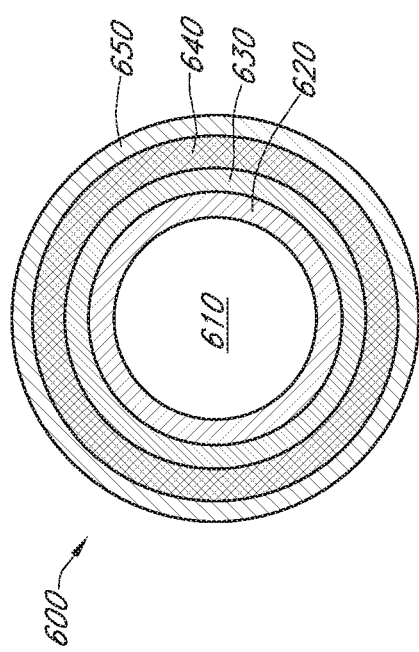
FIG. 6 illustrates a cross-sectional view through one embodiment of the sensor depicting one embodiment of the membrane system.

FIG. 6 is a cross-sectional view through one embodiment of an electrode illustrating one embodiment of the membrane system 600. In this particular embodiment, the membrane system 600 comprises an electrode layer 620, interference layer 630, enzyme layer 640, and a diffusion resistance layer 650, located around the core 610 of the electrode.

Described below are examples of layers that can be coated onto the elongated conductive body to form the membrane system.

Diffusion Resistance Layer

In some embodiments, the membrane system comprises a diffusion resistance layer, which may be disposed more distal to the elongated conductive core than the other layers. A molar excess of glucose relative to the amount of oxygen exists in blood, i.e., for every free oxygen molecule in extracellular fluid, there are typically more than 100 glucose molecules present (see, e.g., Updike et al., *Diabetes Care* 5:207-21 (1982)). Accordingly, without a semipermeable membrane situated over the enzyme layer to control the flux of glucose and oxygen, a linear response to glucose levels can or be obtained only up to about 40 mg/dL. However, in a clinical setting, a linear response to glucose levels is desirable up to at least about 500 mg/dL. The diffusion resistance layer serves to address these issues by controlling the flux of oxygen and other analytes (for example, glucose) to the underlying enzyme layer.

The diffusion resistance layer can include a semipermeable membrane that controls the flux of oxygen and glucose to the underlying enzyme layer, thereby rendering oxygen in non-rate-limiting excess. As a result, the upper limit of linearity of glucose measurement is extended to a much higher value than that which is achieved without the diffusion resistance layer. In some embodiments, the diffusion resistance layer exhibits an oxygen-to-glucose permeability ratio of approximately 200:1, but in other embodiments the oxygen-to-glucose permeability ratio can be approximately 100:1, 125:1, 130:1, 135:1, 150:1, 175:1, 225:1, 250:1, 275:1, 300:1, or 500:1. As a result of the high oxygen-to-glucose permeability ratio, one-dimensional reactant diffusion may provide sufficient excess oxygen at all reasonable glucose and oxygen concentrations found in the subcutaneous matrix (See Rhodes et al., *Anal. Chem.*, 66:1520-1529 (1994)).

In some embodiments, the diffusion resistance layer is formed of a base polymer synthesized to include a polyurethane membrane with both hydrophilic and hydrophobic regions to control the diffusion of glucose and oxygen to an analyte sensor. A suitable hydrophobic polymer component can be a polyurethane or polyether urethane urea. Polyurethane is a polymer produced by the condensation reaction of a diisocyanate and a difunctional hydroxyl-containing material. A polyurea is a polymer produced by the condensation reaction of a diisocyanate and a difunctional amine-containing material. Diisocyanates that can be used include aliphatic diisocyanates containing from about 4 to about 8 methylene units. Diisocyanates containing cycloaliphatic moieties can also be useful in the preparation of the polymer and copolymer components of the membranes of some embodiments. The material that forms the basis of the hydrophobic matrix of the diffusion resistance layer can be any of those known in the art that is suitable for use as membranes in sensor devices and as having sufficient permeability to allow relevant compounds to pass through it, for example, to allow an oxygen molecule to pass through the membrane from the sample under examination in order to reach the active enzyme or electrochemical electrodes. Examples of materials which can be used to make non-polyurethane type membranes include vinyl polymers, polyethers, polyesters, polyamides, inorganic polymers such as polysiloxanes and polycarbosiloxanes, natural polymers such as cellulosic and protein based materials, and mixtures or combinations thereof.

In some embodiments, the diffusion resistance layer can comprise a blend of a base polymer (e.g., polyurethane) and one or more hydrophilic polymers (e.g., PVA, PEG, polyacrylamide, acetates, PEO, PEA, PVP, and variations thereof). It is contemplated that any of a variety of combination of polymers may be used to yield a blend with desired glucose, oxygen, and interference permeability properties. For example, in some embodiments, the diffusion resistance layer can be formed from a blend of a silicone polycarbonate-urethane base polymer and a PVP hydrophilic polymer, but in other embodiments, a blend of a polyurethane, or another base polymer, and one or more hydrophilic polymers can be used instead. In some of the embodiments involving the use of PVP, the PVP portion of the polymer blend can comprise from about 5% to about 50% by weight of the polymer blend, or from about 15% to 20%, or from about 25% to 40%. It is contemplated that PVP of various molecular weights may be used. For example, in some embodiments, the molecular weight of the PVP used can be from about 25,000 daltons to about 5,000,000 daltons, or from about 50,000 daltons to about 2,000,000 daltons, or from 6,000,000 daltons to about 10,000,000 daltons.

In certain embodiments, the thickness of the diffusion resistance layer can be from about 0.05 microns or less to about 200 microns or more. In some of these embodiments, the thickness of the diffusion resistance layer can be from about 0.05, 0.1, 0.15, 0.2, 0.25, 0.3, 0.35, 0.4, 0.45, 0.5, 1, 1.5, 2, 2.5, 3, 3.5, 4, 6, 8 microns to about 9, 10, 11, 12, 13, 14, 15, 16, 17, 18, 19, 19.5, 20, 30, 40, 50, 60, 70, 75, 80, 85, 90, 95, or 100 microns. In some embodiments, the thickness of the diffusion resistance layer is from about 2, 2.5 or 3 microns to about 3.5, 4, 4.5, or 5 microns in the case of a transcutaneously implanted sensor or from about 20 or 25 microns to about 40 or 50 microns in the case of a wholly implanted sensor.

The description herein of the diffusion resistance layer is not intended to be applicable only to the diffusion resistance layer; rather the description can also be applicable to any other layer of the membrane system, such as the enzyme layer, electrode layer, or interference layer, for example.

Enzyme Layer

In some embodiments, the membrane system comprises an enzyme layer, which may be disposed more proximal to the elongated conductive core than the diffusion resistance layer. The enzyme layer comprises a catalyst configured to react with an analyte. In one embodiment, the enzyme layer is an immobilized enzyme layer including glucose oxidase. In other embodiments, the enzyme layer can be impregnated with other oxidases, for example, alcohol dehydrogenase, galactose oxidase, cholesterol oxidase, amino acid oxidase, alcohol oxidase, lactate oxidase, or uricase. For example, for an enzyme-based electrochemical glucose sensor to perform well, the sensor's response should neither be limited by enzyme activity nor cofactor concentration.

In some embodiments, the catalyst (enzyme) can be impregnated or otherwise immobilized into the diffusion resistance layer such that a separate enzyme layer is not required (e.g., wherein a unitary layer is provided including the functionality of the diffusion resistance layer and enzyme layer). In some embodiments, the enzyme layer is formed from a polyurethane, for example, aqueous dispersions of colloidal polyurethane polymers including the enzyme.

In some embodiments, the thickness of the enzyme layer can be from about 0.01, 0.05, 0.6, 0.7, or 0.8 microns to about 1, 1.2, 1.4, 1.5, 1.6, 1.8, 2, 2.1, 2.2, 2.5, 3, 4, 5, 10, 20, 30 40, 50, 60, 70, 80, 90, or 100 microns. In some embodiments, the thickness of the enzyme layer is from about 0.05, 0.1, 0.15, 0.2, 0.25, 0.3, 0.35, 0.4, 0.45, 0.5, 1, 1.5, 2, 2.5, 3, 4, or 5 microns to about 6, 7, 8, 9, 10, 11, 12, 13, 14, 15, 16, 17, 18, 19, 19.5, 20, 25, or 30 microns, or from about 2, 2.5, or 3 microns to about 3.5, 4, 4.5, or 5 microns in the case of a transcutaneously implanted sensor or from about 6, 7, or 8 microns to about 9, 10, 11, or 12 microns in the case of a wholly implanted sensor.

The description herein of the enzyme layer is not intended to be applicable only to the enzyme layer; rather the description can also be applicable to any other layer of the membrane system, such as the diffusion resistance layer, electrode layer, or interference layer, for example.

Electrode Layer

In some embodiments, the membrane system comprises an electrode layer, which may be disposed more proximal to the elongated conductive core than any other layer. The electrode layer is configured to facilitate electrochemical reaction on the electroactive surface and can include a semipermeable coating for maintaining hydrophilicity at the electrochemically reactive surfaces of the sensor interface. In other embodiments, the functionality of the electrode layer can be incorporated into the diffusion resistance layer, so as to provide a unitary layer that includes the functionality of the diffusion resistance layer, enzyme layer, and/or electrode layer.

The electrode layer can enhance the stability of an adjacent layer by protecting and supporting the material that makes up the adjacent layer. The electrode layer may also assist in stabilizing the operation of the device by overcoming electrode start-up problems and drifting problems caused by inadequate electrolyte. The buffered electrolyte solution contained in the electrode layer may also protect against pH-mediated damage that can result from the formation of a large pH gradient between the substantially hydrophobic interference layer and the electrodes due to the electrochemical activity of the electrodes.

In one embodiment, the electrode domain includes hydrophilic polymer film (e.g., a flexible, water-swellable, hydrogel) having a "dry film" thickness of from about 0.05 microns or less to about 20 microns or more, or from about 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns, or from about 3, 2.5, 2, or 1 microns, or less, to about 3.5, 4, 4.5, or 5 microns or more. "Dry film" thickness refers to the thickness of a cured film cast from a coating formulation by standard coating techniques.

In certain embodiments, the electrode layer can be formed of a curable mixture of a urethane polymer and a hydrophilic polymer. In some of these embodiments, coatings are formed of a polyurethane polymer having anionic carboxylate functional groups and non-ionic hydrophilic polyether segments, wherein the polyurethane polymer undergoes aggregation with a water-soluble carbodiimide (e.g., 1-ethyl-3-(3-dimethylaminopropyl)carbodiimide (EDC)) in the presence of polyvinylpyrrolidone and cured at a moderate temperature of about 50° C.

Particularly suitable for this purpose are aqueous dispersions of fully-reacted colloidal polyurethane polymers having cross-linkable carboxyl functionality (e.g., BAYBOND®; Mobay Corporation). These polymers are supplied in dispersion grades having a polycarbonate-polyurethane backbone containing carboxylate groups identified as W-121 and XW-123; and a polyester-polyurethane backbone containing carboxylate groups, identified as W-110-2. In some embodiments, BAYBOND® 123, an aqueous anionic dispersion of an aliphatic polycarbonate urethane polymer sold as a 35 weight percent solution in water and co-solvent N-methyl-2-pyrrolidone, can be used.

In some embodiments, the electrode layer is formed from a hydrophilic polymer that renders the electrode layer substantially more hydrophilic than an overlying layer (e.g., interference layer, enzyme layer). Such hydrophilic polymers can include, a polyamide, a polylactone, a polyimide, a polylactam, a functionalized polyamide, a functionalized polylactone, a functionalized polyimide, a functionalized polylactam or combinations thereof, for example.

In some embodiments, the electrode layer is formed primarily from a hydrophilic polymer, and in some of these embodiments, the electrode layer is formed substantially from PVP. PVP is a hydrophilic water-soluble polymer and is available commercially in a range of viscosity grades and average molecular weights ranging from about 18,000 to about 500,000, under the PVP K® homopolymer series by BASF Wyandotte and by GAF Corporation. In certain embodiments, a PVP homopolymer having an average molecular weight of about 360,000 identified as PVP-K90 (BASF Wyandotte) can be used to form the electrode layer. Also suitable are hydrophilic, film-forming copolymers of N-vinylpyrrolidone, such as a copolymer of N-vinylpyrrolidone and vinyl acetate, a copolymer of N-vinylpyrrolidone, ethylmethacrylate and methacrylic acid monomers, and the like.

In certain embodiments, the electrode layer is formed entirely from a hydrophilic polymer. Useful hydrophilic polymers contemplated include, but are not limited to, poly-N-vinylpyrrolidone, poly-N-vinyl-2-piperidone, poly-N-vinyl-2-caprolactam, poly-N-vinyl-3-methyl-2-caprolactam, poly-N-vinyl-3-methyl-2-piperidone, poly-N-vinyl-4-methyl-2-piperidone, poly-N-vinyl-4-methyl-2-caprolactam, poly-N-vinyl-3-ethyl-2-pyrrolidone, poly-N-vinyl-4,5-dimethyl-2-pyrrolidone, polyvinylimidazole, poly-N,N-dimethylacrylamide, polyvinyl alcohol, polyacrylic acid, polyethylene oxide, poly-2-ethyl-oxazoline, copolymers thereof and mixtures thereof. A blend of two or more hydrophilic polymers can be preferred in some embodiments.

It is contemplated that in certain embodiments, the hydrophilic polymer used may not be crosslinked, but in other embodiments, crosslinking may be used and achieved by any of a variety of methods, for example, by adding a crosslinking agent. In some embodiments, a polyurethane polymer can be crosslinked in the presence of PVP by preparing a premix of the polymers and adding a cross-linking agent just prior to the production of the membrane. Suitable cross-linking agents contemplated include, but are not limited to, carbodiimides (e.g., 1-ethyl-3-(3-dimethylaminopropyl) carbodiimide hydrochloride, UCARLNK®. XL-25 (Union Carbide)), epoxides and melamine/formaldehyde resins. Alternatively, it is also contemplated that crosslinking can be achieved by irradiation at a wavelength sufficient to promote crosslinking between the hydrophilic polymer molecules, which is believed to create a more tortuous diffusion path through the layer.

The flexibility and hardness of the coating can be varied as desired by varying the dry weight solids of the components in the coating formulation. The term "dry weight solids" as used herein is a broad term, and is to be given its ordinary and customary meaning to a person of ordinary skill in the art (and is not to be limited to a special or customized meaning), and refers without limitation to the dry weight percent based on the total coating composition after the time the crosslinker is included. In one embodiment, a coating formulation can contain about 6 to about 20 dry weight percent, or about 8 dry weight percent, PVP; about 3 to about 10 dry weight percent, or about 5 dry weight percent cross-linking agent; and about 70 to about 91 weight percent, or about 87 weight percent of a polyurethane polymer, such as a polycarbonate-polyurethane polymer, for example. The reaction product of such a coating formulation is referred to herein as a water-swellable cross-linked matrix of polyurethane and PVP.

In some embodiments, underlying the electrode layer is an electrolyte phase that when hydrated is a free-fluid phase including a solution containing at least one compound, typically a soluble chloride salt, which conducts electric current. In one embodiment wherein the membrane system is used with a glucose sensor such as is described herein, the electrolyte phase flows over the electrodes and is in contact with the electrode layer. It is contemplated that certain embodiments can use any suitable electrolyte solution, including standard, commercially available solutions. Generally, the electrolyte phase can have the same osmotic pressure or a lower osmotic pressure than the sample being analyzed. In some embodiments, the electrolyte phase comprises normal saline.

The description herein of the electrode layer is not intended to be applicable only to the electrode layer; rather the description can also be applicable to any other layer of the membrane system, such as the diffusion resistance layer, enzyme layer, or interference layer, for example.

Interference Layer

In some embodiments, the membrane system may comprise an interference layer configured to substantially reduce the permeation of one or more interferents into the electrochemically reactive surfaces. The interference layer may be configured to be substantially less permeable to one or more of the interferents than to the measured species. It is also contemplated that in some embodiments, where interferent blocking may be provided by the diffusion resistance layer (e.g., via a surface-active group-containing polymer of the diffusion resistance layer), a separate interference layer may not be used.

In some embodiments, the interference layer is formed from a silicone-containing polymer, such as a polyurethane containing silicone, or a silicone polymer. While not wishing to be bound by theory, it is believed that, in order for an enzyme-based glucose sensor to function properly, glucose would not have to permeate the interference layer, where the interference layer is located more proximal to the electroactive surfaces than the enzyme layer. Accordingly, in some embodiments, a silicone-containing interference layer, comprising a greater percentage of silicone by weight than the diffusion resistance layer, can be used without substantially affecting glucose concentration measurements. For example, in some embodiments, the silicone-containing interference layer can comprise a polymer with a high percentage of silicone (e.g., from about 25%, 30%, 35%, 40%, 45%, or 50% to about 60%, 70%, 80%, 90% or 95%).

In one embodiment, the interference layer can include ionic components incorporated into a polymeric matrix to reduce the permeability of the interference layer to ionic interferents having the same charge as the ionic components. In another embodiment, the interference layer can include a catalyst (for example, peroxidase) for catalyzing a reaction that removes interferents.

In certain embodiments, the interference layer can include a thin membrane that is designed to limit diffusion of certain species, for example, those greater than 34 kD in molecular weight. In these embodiments, the interference layer permits certain substances (for example, hydrogen peroxide) that are to be measured by the electrodes to pass through, and prevents passage of other substances, such as potentially interfering substances. In one embodiment, the interference layer is constructed of polyurethane. In an alternative embodiment, the interference layer comprises a high oxygen soluble polymer, such as silicone.

In some embodiments, the interference layer is formed from one or more cellulosic derivatives. In general, cellulosic derivatives can include polymers such as cellulose acetate, cellulose acetate butyrate, 2-hydroxyethyl cellulose, cellulose acetate phthalate, cellulose acetate propionate, cellulose acetate trimellitate, or blends and combinations thereof.

In some alternative embodiments, other polymer types that can be utilized as a base material for the interference layer include polyurethanes, polymers having pendant ionic groups, and polymers having controlled pore size, for example. In one such alternative embodiment, the interference layer includes a thin, hydrophobic membrane that is non-swellable and restricts diffusion of low molecular weight species. The interference layer is permeable to relatively low molecular weight substances, such as hydrogen peroxide, but restricts the passage of higher molecular weight substances, including glucose and ascorbic acid.

It is contemplated that in some embodiments, the thickness of the interference layer can be from about 0.01 microns or less to about 20 microns or more. In some of these embodiments, the thickness of the interference layer can be from about 0.01, 0.05, 0.1, 0.15, 0.2, 0.25, 0.3, 0.35, 0.4, 0.45, 0.5, 1, 1.5, 2, 2.5, 3, or 3.5 microns to about 4, 5, 6, 7, 8, 9, 10, 11, 12, 13, 14, 15, 16, 17, 18, 19, or 19.5 microns. In some of these embodiments, the thickness of the interference layer can be from about 0.2, 0.4, 0.5, or 0.6, microns to about 0.8, 0.9, 1, 1.5, 2, 3, or 4 microns.

The description herein of the interference layer is not intended to be applicable only to the interference layer; rather the description can also be applicable to any other layer of the membrane system, such as the diffusion resistance layer, enzyme layer, or electrode layer, for example.

Therapeutic Agents

A variety of therapeutic (bioactive) agents can be used with the analyte sensor system. In some embodiments, the therapeutic agent is an anticoagulant for preventing coagulation within or on the sensor. In some embodiments, the therapeutic agent is an antimicrobial, such as but not limited to an antibiotic or antifungal compound. In some embodiments, the therapeutic agent is an antiseptic and/or disinfectant. Therapeutic agents can be used alone or in combination of two or more agents. The therapeutic agents can be dispersed throughout the material of the sensor. In some embodiments, the membrane system can include a therapeutic agent that is incorporated into a portion of the membrane system, or which is incorporated into the device and adapted to diffuse through the membrane.

There are a variety of systems and methods by which the therapeutic agent can be incorporated into the membrane system. In some embodiments, the therapeutic agent is incorporated at the time of manufacture of the membrane system. For example, the therapeutic agent can be blended prior to curing the membrane system. In other embodiments, the therapeutic agent is incorporated subsequent to membrane system manufacture, for example, by coating, imbibing, solvent-casting, or sorption of the bioactive agent into the membrane system. Although the therapeutic agent can be incorporated into the membrane system, in some embodiments the therapeutic agent can be administered concurrently with, prior to, or after insertion of the device intravascularly, for example, by oral administration, or locally, for example, by subcutaneous injection near the implantation site. In some embodiments, a combination of therapeutic agent incorporated in the membrane system and therapeutic agent administration locally and/or systemically can be used.

Mounting Unit

As illustrated in FIG. 1, the sensor device 100 may include a skin-contacting mounting unit 150 configured to be secured to a host. In some embodiments, the mounting unit 150 comprises a base 152 adapted for fastening to a host's skin. The base 152 can be formed from a variety of hard or soft materials and may comprise a low profile for minimizing protrusion of the sensor device from the host during use. In some embodiments, the base 152 is formed at least partially from a flexible material configured to conform to skin contour, so as to reduce or eliminate motion-related artifacts associated with movement by the host. To achieve this flexibility, the material chosen may have a flexural modulus of less than about 5,000 MPa, or less than about 1,000 MPa, or less than about 500 MPa, or less than about 100 MPa, or less than about 50 MPa, as determined by ASTM D790. The base 152 may have a preselected thickness that allows the material to flex with movements of the skin. When a transcutaneous sensor device is inserted into the host, various movements of the sensor (for example, relative movement between the in vivo portion and the ex vivo portion, movement of the skin, and/or movement within the host (dermis or subcutaneous)) can create stresses on the device and produce noise in the sensor signal. It is believed that even small movements of the skin can translate to discomfort and/or motion-related artifacts, which can be reduced or obviated by a flexible or articulated base. Thus, by providing flexibility and/or articulation of the sensor device against the host's skin, better conformity of the sensor device to the regular use and movements of the host can be achieved. Flexibility or articulation is believed to increase adhesion (with the use of an adhesive layer) of the mounting unit 150 onto the skin 180, thereby decreasing motion-related artifacts that can otherwise translate from the host's movements and reduce sensor performance.

In certain embodiments, the base 152 of the mounting unit 150 is provided with an adhesive material or adhesive layer 154, also referred to as an adhesive pad, preferably disposed on the mounting unit's bottom surface and may including a releasable backing layer. Thus, removing the backing layer and pressing the base 152 of the mounting unit 150 onto the host's skin 180 adheres the mounting unit 150 to the host's skin 180. Appropriate adhesive layers can be chosen and designed to stretch, elongate, conform to, and/or aerate the region (e.g. host's skin).

Any of a variety of adhesive layers appropriate for adhesion to the host's skin can be used. For example, in certain embodiments, the adhesive layer is formed from spun-laced, open- or closed-cell foam, and/or non-woven fibers, and includes an adhesive disposed thereon. In some embodiments, a double-sided adhesive layer is used to adhere the mounting unit to the host's skin. In other embodiments, the adhesive layer includes a foam layer, for example, a layer wherein the foam is disposed between the adhesive layer's side edges and acts as a shock absorber. In certain embodiments, the adhesive layer is formed of a waterproof material.

In some embodiments, the surface area of the adhesive layer is greater than the surface area of the bottom surface of the mounting unit's base. Alternatively, the adhesive layer can be sized with substantially the same surface area as the bottom surface of the base. The adhesive layer may have a surface area on the side to be mounted on the host's skin that is greater than about 1, 1.25, 1.5, 1.75, 2, 2.25, or 2.5 times the surface area of the bottom surface of the mounting unit base. Such a greater surface area can increase adhesion between the mounting unit and the host's skin, minimize movement between the mounting unit and the host's skin, and/or protect the wound exit-site (sensor insertion site) from environmental and/or biological contamination. In some alternative embodiments, however, the adhesive layer can be smaller in surface area than the back surface assuming a sufficient adhesion can be accomplished.

As illustrated in FIGS. 3A-3C, in certain embodiments, the mounting unit 350 may comprise contacts 358 for providing a stable mechanical and electrical connection between the electrodes and the sensor electronics unit, which is described in greater detail elsewhere herein. A stable connection can be provided using a variety of known methods, for example, raised (e.g., domed) metallic contacts, cantilevered fingers, pogo pins, or the like. In certain embodiments, the contacts are formed from a conductive elastomeric material, such as a carbon black elastomer, through which the electrodes extend. Conductive elastomers may be preferred in some instances because their resilient properties create a natural compression against mutually engaging contacts, thereby providing a secure press fit therewith. In other embodiments, the contacts are formed from a stiff plastic material, which is shaped to comply upon application of pressure. Non-metallic contacts can be preferred in some instances because of their seamless manufacturability, robustness to thermal compression, non-corrosive surfaces, and native resistance to electrostatic discharge (ESD) damage due to their higher-than-metal resistance. In still other embodiments, the mounting unit does not comprise contacts. Instead, the electrodes may be directly hardwired to the sensor electronics unit, to provide electrical connection prior to, during, and/or after sensor insertion.

Figure 8A:
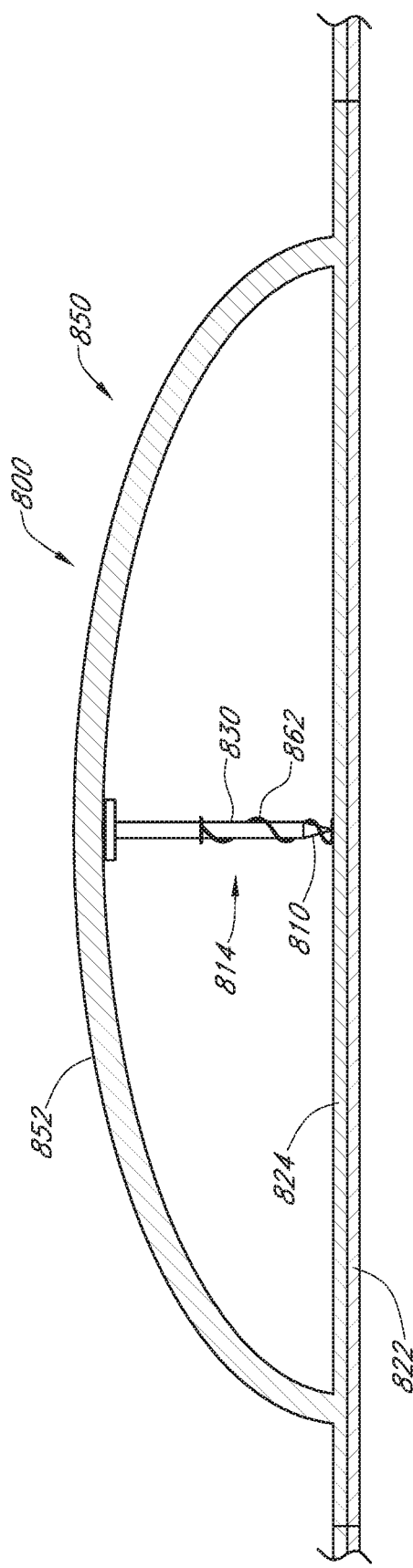
FIG. 8A illustrates one embodiment of the sensor device with a mounting unit comprising a raised upper surface.

FIG. 8A illustrates one embodiment of a mounting unit 850 with a raised upper surface 852, formed of an elastomeric material and adapted to receive a pressure from a user for insertion of the in vivo portion of the sensor device. In some embodiments, the raised upper surface 852 may be detachably attached to a sensor unit 814 comprising a tissue piercing element 810 and a sensor body 830, which is comprised of one or more electrodes with a membrane disposed thereon. While the upper surface 852 is shown here with a domed shape, any of a variety of other shapes may be used, such as a frusto-conical shape, for example. As shown in FIG. 8A, the sensor device 800 may be a self-containing sterile field and be supplied to the user with the sensor unit 814 in a retracted state, i.e., with the in vivo portion hidden inside the sensor device 800. This configuration allows the user to place the sensor device 800 on the skin without the possibility of observing the sensor unit 814. With the sensor unit 814 hidden, some of the fear to the user of using the sensor device may be abated, thereby making the insertion of the sensor unit 814 less problematic. To use the sensor device 800, the user first peels the sensor device 800 away from a backing layer 822. With the backing layer 822 peeled away, a sterile bottom surface 824 of the sensor device 800 is exposed, such that further sterilization of the sensor device's contact surface 824 with the host's skin may not be required. The bottom surface 824 of the sensor device comprises an adhesive that readily allows the mounting unit to be adhered to the skin. After the sensor device 800 has been adhered to the host's skin, the sensor unit 814 is introduced into the host's tissue, as the user presses the upper surface (e.g., the dome) of the mounting unit 850 downwards to cause the in vivo portion of the sensor device to penetrate the host's skin. In certain embodiments, after pressure is released from the upper surface 852, the upper surface 852 becomes detached from the sensor unit 814, as it resumes its normal convex shape, and as the sensor body 830 remains embedded in the host's tissue. In alternative embodiments, instead of (or in addition to) using a downward pressure from the top of the upper surface 852 to cause collapse of the upper surface 852, the sensor device 800 may be configured such that pressure from other directions can be used. For example, the sensor device 800 may be equipped with two diametrically opposed tabs, placed at the edges of the upper surface 852, that are to be pulled in opposite directions to cause collapse of the upper surface 852, thereby resulting in the deployment of the sensor body 830. In still other embodiments, other mechanisms not relying entirely on pressure applied by the user can also be employed. For instance, in one embodiment, the upper surface 852 may be formed of a material (e.g., a shape memory material) that is conducive to inducing the sensor device 800 a collapsed state. In this embodiment, removal of the backing layer 822 and a mere slight touch by the user may be sufficient to cause collapse of the upper surface 852 and deployment of the sensor body 830.

Figure 8B:
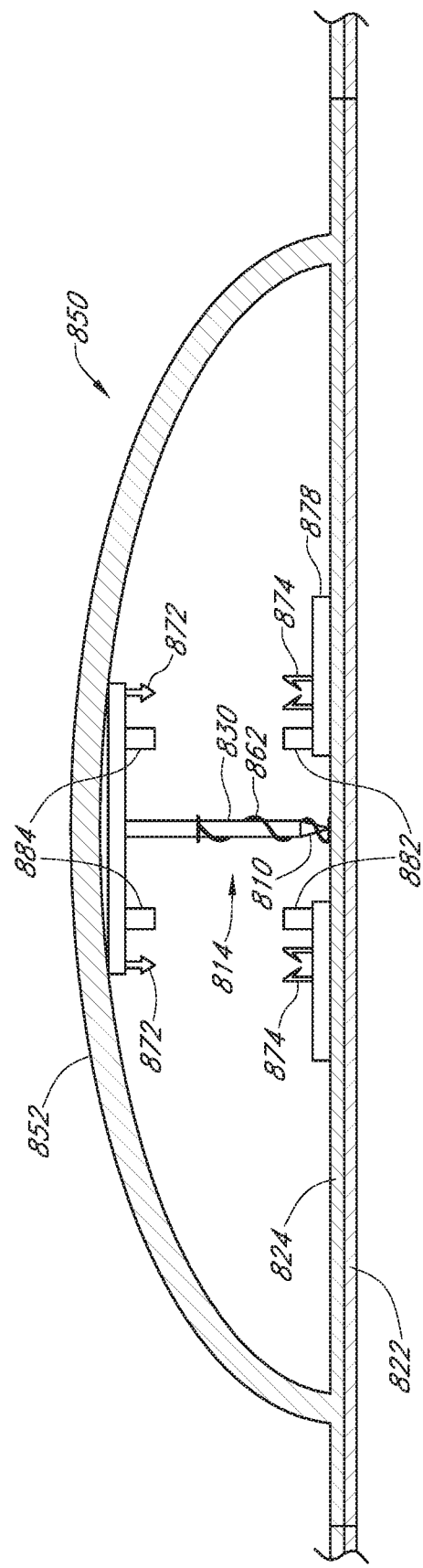
FIG. 8B illustrates another embodiment of the sensor device with a mounting unit comprising a raised upper surface.

In some embodiments, the raised upper surface 852 and the bottom surface 824 are configured to be readily peeled away by the user after insertion of the sensor unit 814. In other embodiments, the raised upper surface 852 and/or the bottom surface 824 are configured to remain with the sensor unit 814 after insertion. In further embodiments, the raised upper surface 852 may be configured to remain in a collapsed state after the insertion process. This configuration may be preferable in some instances, because the resulting lower profile of the sensor device 800 may reduce the risk of movement of the upper surface 852 (e.g., from an accidental bump by the host), which could translate to movement of the sensor unit 814 and thus create motion-related artifacts. Any of a variety of mechanism may be used to achieve the collapsed state configuration. For example, as illustrated in FIG. 8B, in one embodiment, the sensor device 800 may comprise a locking mechanism in the form of a latch member 872 attached to the bottom side of the upper surface 852 and a locking receptacle 874 that is part of a base 878. The latch member 872 and the locking receptacle 874 are configured to mate with each other during the sensor insertion process, thereby bringing contacts 882, 884 together, so that an electrical connection between the sensor unit and the sensor electronics is made. In some embodiments, the base 878 forms at least a portion of the sensor electronics unit and/or comprises a transmitter that is configured to transmit sensor data to a remote computer system.

Figure 8C:
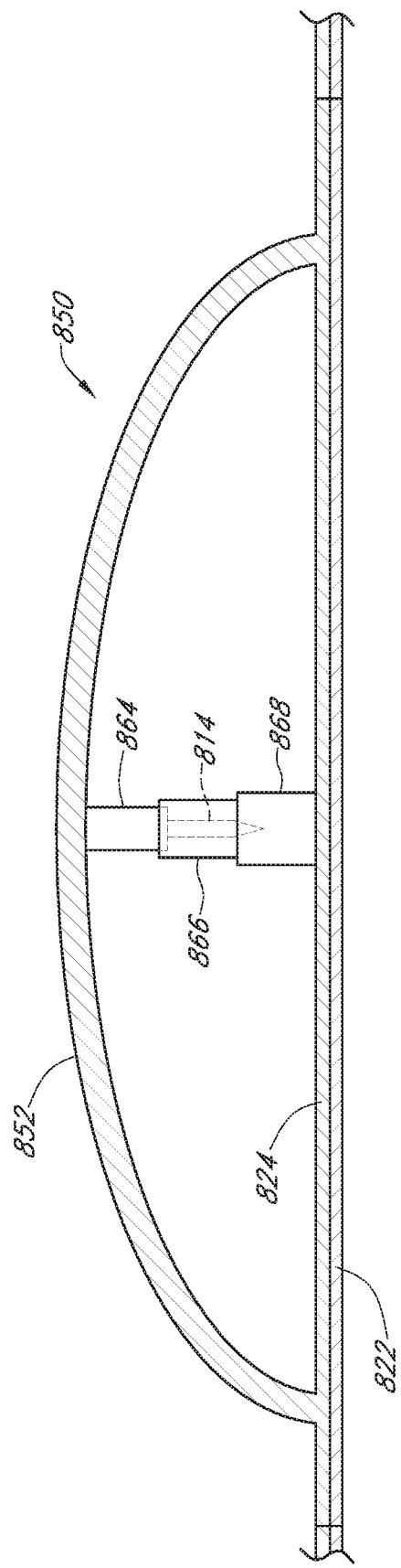
FIG. 8C illustrates still another embodiment of the sensor device with a mounting unit comprising a raised upper surface.

To enhance column strength and stability of the in vivo portion of the sensor device, some of the mounting units described herein, such as those illustrated in FIGS. 8A and 8B, may comprise a guiding portion 862 configured to provide guidance and support to the in vivo portion of the sensor device 800 as it is inserted through the skin of the host. It has been found that the largest force needed for the insertion process involves the force required to push the tip of the sensor device 800 through the skin. Once a portion of the sensor device 800 has penetrated through the skin, an opening is created by the tissue piercing element 810 that permits the rest of the sensor device 800 to pass through the skin with minimal resistance. Additionally, as this occurs, the tissue surrounding the sensor device 800 presses against that portion of the sensor device 800 and thus provides it with additional column strength. The guiding portion 862 may have any of a variety of configurations. For example, as illustrated in FIG. 8A, in some embodiments, the guiding portion 862 may have a configuration of a spiraling spring, through which the tissue piercing element and/or sensor body may pass. Alternatively, the guiding portion 862 may have a tube configuration, as illustrated in FIG. 8C. In this particular embodiment, a nested tube mechanism is used which may include an inner tubular member 864, and optionally one or more intermediate tubular members 866, nested within the lumen of an outer tubular member 868. The sensor unit 814 is attached to the inner tubular member and configured to be moved longitudinally through the skin, as the inner tubular member 864 is advanced into the intermediate tubular member 866, and into the outer tubular member 868, as illustrated in FIG. 8D. In further embodiments, the tubular members may comprise latches configured to lock the tubular members in place, after the inner tubular member 864 has been advanced into the intermediate tubular member 866 and the outer tubular member 868, to prevent the sensor unit 814 from withdrawing back into its original retracted position.

Figure 3E:
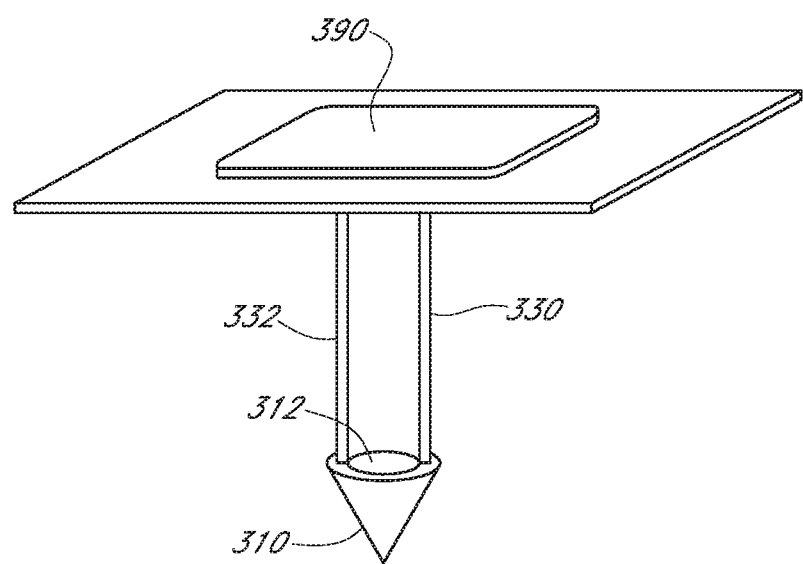
FIG. 3E illustrates one embodiment, in which a sensor electronics unit is adapted to be united with a mounting unit.

As illustrated in FIG. 3E, in some embodiments, the mounting unit 350 is adapted to be united with a sensor electronics unit 390, which is described in greater detail elsewhere herein, to collectively form an on-skin unit. In certain embodiments, the sensor electronics unit can be detachable from (e.g., releasably attached to) the mounting unit, but in other embodiments, the sensor electronics unit is integral with and not detachable from the mounting unit. The on-skin unit may further include a user interface which displays sensor information to the host via any of a variety of methods for displaying sensor information, such as an LED, an LCD screen, computer-generated audible information, tactile signals, or other user interface types, for example. The term "user interface" as used herein is a broad term, and is to be given its ordinary and customary meaning to a person of ordinary skill in the art (and is not to be limited to a special or customized meaning), and refers without limitation to any method of communication to the user.

Figure 9A:
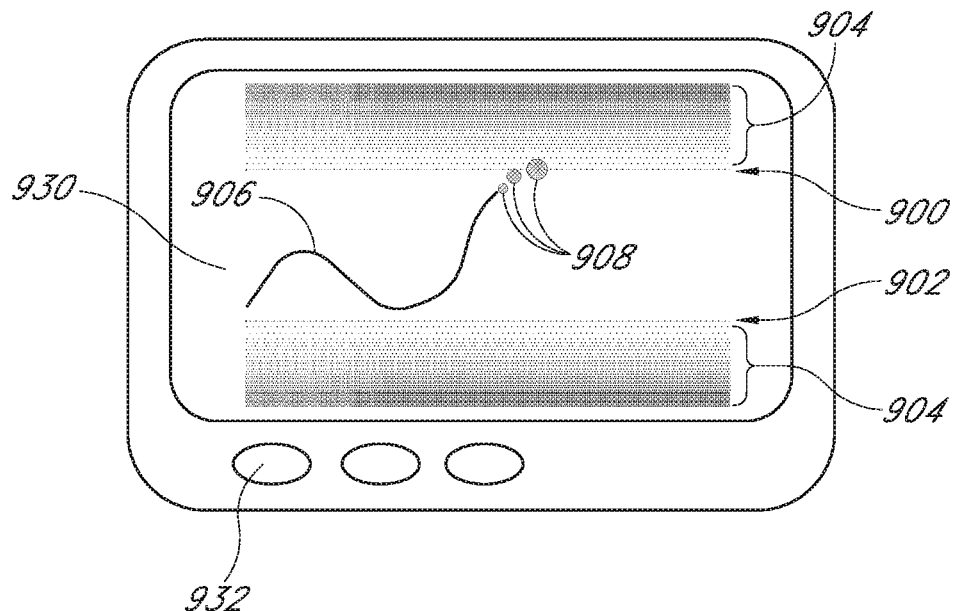
FIG. 9A illustrates one embodiment of a user interface displaying an analyte trend graph, including measured analyte values, estimated analyte values, and a zone of clinical risk.

In some embodiments such as shown in FIG. 9A, the user interface includes a screen 930 that shows thresholds, including a high threshold 900 and a low threshold 902, which represent boundaries between clinically safe and clinically risky conditions for the patients. In one exemplary embodiment, a normal glucose threshold for a glucose sensor is set from about 100 to 160 mg/dL, and the clinical risk zones 904 are illustrated outside of these thresholds. In alternative embodiments, the normal glucose threshold is from about 80 to about 200 mg/dL, from about 55 to about 220 mg/dL, or other threshold that can be set by the manufacturer, physician, patient, computer program, or the like. Although a few examples of glucose thresholds are given for a glucose sensor, the setting of any analyte threshold is not limited by the preferred embodiments.

In some embodiments, the screen 930 that shows clinical risk zones 904 (also referred to as danger zones, through shading, gradients) or other graphical illustrations that indicate areas of increasing clinical risk. Clinical risk zones 904 can be set by a manufacturer, customized by a doctor, and/or set by a user via buttons 932, for example. In some embodiments, the danger zone 904 can be continuously shown on the screen 930, or the danger zone can appear when the measured and/or estimated analyte values fall into the danger zone 904. Additional information can be displayed on the screen, such as an estimated time to clinical risk. In some embodiments, the danger zone can be divided into levels of danger (for example, low, medium, and high) and/or can be color-coded (for example, yellow, orange, and red) or otherwise illustrated to indicate the level of danger to the patient. Additionally, the screen or portion of the screen can dynamically change colors or illustrations that represent a nearness to the clinical risk and/or a severity of clinical risk.

In some embodiments, such as that shown in FIG. 9A, the screen 930 displays a trend graph of measured analyte data 906. Measured analyte data can be smoothed and calibrated such as described in more detail elsewhere herein. Measured analyte data can be displayed for a certain time period (for example, previous 1 hour, 3 hours, 9 hours, etc.) In some embodiments, the user can toggle through screens using buttons 932 to view the measured analyte data for different time periods, using different formats, or to view certain analyte values (for example, highs and lows).

In some embodiments such as shown in FIG. 9A, the screen 930 displays estimated analyte data 908 using dots. In this illustration, the size of the dots can represent the confidence of the estimation, a variation of estimated values, or the like. For example, as the time gets farther away from the present (t=0) the confidence level in the accuracy of the estimation can decline. In some alternative embodiments, dashed lines, symbols, icons, or the like can be used to represent the estimated analyte values. In some alternative embodiments, shaded regions, colors, patterns, or the like can also be used to represent the estimated analyte values, a confidence in those values, and/or a variation of those values.

Figure 9B:
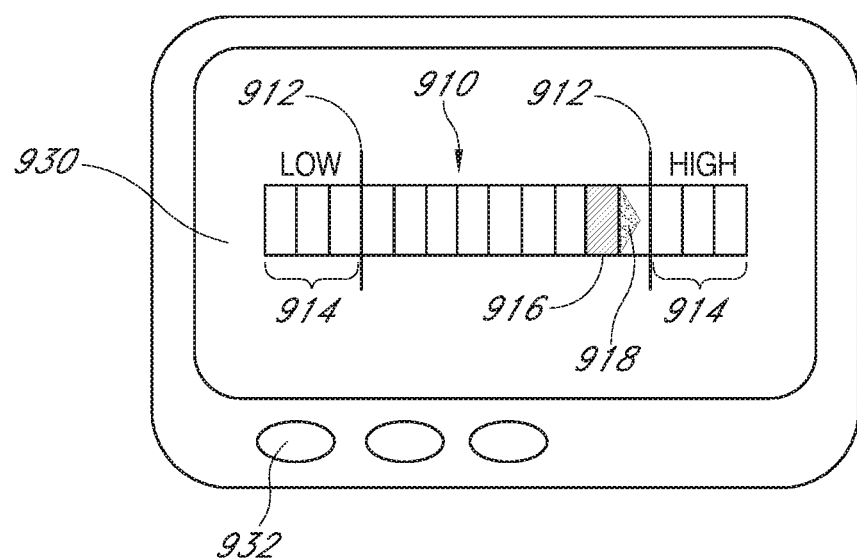
FIG. 9B illustrates one embodiment of a user interface displaying a gradient bar, including measured analyte values, estimated analyte values, and a zone of clinical risk.

FIG. 9B is an illustration of a user interface in another embodiment showing a representation of analyte concentration and directional trend using a gradient bar. In this embodiment, the screen 930 illustrates the measured analyte values and estimated analyte values in a simple but effective manner that communicates valuable analyte information to the user. In this embodiment, a gradient bar 910 is provided that includes thresholds 912 set at highs and lows such as described in more detail with reference to FIG. 9A, above. Additionally, colors, shading, or other graphical illustration can be present to represent danger zones 914 on the gradient bar 910 such as described in more detail with reference to FIG. 9A, above.

The measured analyte value is represented on the gradient bar 910 by a marker 916, such as a darkened or colored bar. By representing the measured analyte value with a bar 916, a low-resolution analyte value is presented to the user (for example, within a range of values). For example, each segment on the gradient bar 916 can represent about 10 mg/dL of glucose concentration. As another example, each segment can dynamically represent the range of values that fall within the "A" and "B" regions of the Clarke Error Grid. While not wishing to be bound by theory, it is believe that inaccuracies known both in reference analyte monitors and/or continuous analyte sensors are likely due to known variables such as described in more detail elsewhere herein, and can be de-emphasized such that a user focuses on proactive care of the condition, rather than inconsequential discrepancies within and between reference analyte monitors and continuous analyte sensors.

Additionally, the representative gradient bar communicates the directional trend of the analyte concentration to the user in a simple and effective manner, namely by a directional arrow 918. For example, in conventional diabetic blood glucose monitoring, a person with diabetes obtains a blood sample and measures the glucose concentration using a test strip, or the like. Unfortunately, this information does not tell the person with diabetes whether the blood glucose concentration is rising or falling. Rising or falling directional trend information can be particularly important in a situation such as illustrated in FIG. 9B, wherein if the user does not know that the glucose concentration is rising, he/she may assume that the glucose concentration is falling and not attend to his/her condition. However, because rising directional trend information 918 is provided, the person with diabetes can preempt the clinical risk by attending to his/her condition (for example, administer insulin). Estimated analyte data can be incorporated into the directional trend information by characteristics of the arrow, for example, size, color, flash speed, or the like.

In some embodiments, the gradient bar can be a vertical instead of horizontal bar. In some embodiments, a gradient fill can be used to represent analyte concentration, variation, or clinical risk, for example. In some embodiments, the bar graph includes color, for example the center can be green in the safe zone that graduates to red in the danger zones; this can be in addition to or in place of the divided segments. In some embodiments, the segments of the bar graph are clearly divided by lines; however color, gradation, or the like can be used to represent areas of the bar graph. In some embodiments, the directional arrow can be represented by a cascading level of arrows to a represent slow or rapid rate of change. In some embodiments, the directional arrow can be flashing to represent movement or pending danger.

The screen 930 of FIG. 9B can further comprise a numerical representation of analyte concentration, date, time, or other information to be communicated to the patient. However, a user can advantageously extrapolate information helpful for his/her condition using the simple and effective representation of this embodiment shown in FIG. 9B, without reading a numeric representation of his/her analyte concentration.

In some alternative embodiments, a trend graph or gradient bar, a dial, pie chart, or other visual representation can provide analyte data using shading, colors, patterns, icons, animation, or the like.

In some embodiments, the user interface includes a color display element that is capable of reversibly changing colors in accordance with changes in analyte concentration (e.g., glucose concentration). For example, the color display element may be configured to exhibit a green color when a glucose concentration is within a predetermined target range. Furthermore, if the sensor device detects hyperglycemia (i.e., a glucose concentration greater than those within the target range), it may change to another color (e.g., a dark blue color). Conversely, if the sensor device detects a hypoglycemic event (i.e., a glucose concentration less those within the target range), it may change to yet another color (e.g., a red color). The color display element may be also be configured to provide a color gradation scheme that represents a degree of change in glucose concentration. By way of example, a color gradation scheme from red (for severe hypoglycemia) to yellow (for mild hypoglycemia) may be used for low glucose concentration levels. Correspondingly, a color gradation scheme from dark blue (for severe hyperglycemia) to light blue (for mild hyperglycemia) may be used for high glucose concentration levels. Any of a variety of color display elements may be used, such as an LED, an LCD, or a color changing material, for example. In some instances, an LED may be desirable, because of its low energy consumption, small size, and robustness. However, in other instances, a low-powered or non-powered mechanism may be desirable. Materials that include a chemical composition having a color indicator (e.g., 4-Aminoantipyrine, N-ethyl-N-(2-hydroxy-3-sulfopropyl)-3,5 dimethoxyaniline) may be used to trigger the color change.

Although in some embodiments, the sensor device may be capable of displaying three or more colors (e.g., a first color for hyperglycemia, a second color for eugylcemia, and a third color for hypoglycemia) for different analyte concentrations, in other embodiments, for simplicity, the sensor device may be designed to display one of two colors and to provide warning to the user about a specific condition (e.g., hypoglycemia). For example, the sensor device may be designed to display a first color for all glucose levels other than hypoglycemia and to display a second color for hypoglycemia. In some embodiments, color change transformation may take place in response to an event involving both analyte concentration and rate of change of analyte concentration. For example, for a sensor device designed to provide warning to the user of a hypoglycemia event, the color display element may designed to trigger color change when both the rate of change of glucose concentration is less than or equal to about $-4$ mg $dL^{-1}$ $min^{-1}$ (e.g., $-4.5$ mg $dL^{-1}$ $min^{-1}$) and the glucose concentration is less than or equal to about 100 mg $dL^{-1}$. It is contemplated that the sensor device may be designed to respond via color change to other events, such as a condition in which the rate of change of glucose concentration is less than or equal to about $-3$ mg $dL^{-1}$ $min^{-1}$ and the glucose concentration is less than or equal to about 90 mg $dL^{-1}$, a condition in which the rate of change of glucose concentration is less than or equal to about $-2$ mg $dL^{-1}$ $min^{-1}$ and the glucose concentration is less than or equal to about 75 mg $dL^{-1}$, a condition in which the rate of change of glucose concentration is less than or equal to about $-1$ mg $dL^{-1}$ $min^{-1}$ and the glucose concentration is less than or equal to about 70 mg $dL^{-1}$, and a condition in which the glucose concentration is less than or equal to about 50 mg $dL^{-1}$ regardless of the rate of change of glucose concentration. It should be understood that the conditions provide herein are merely exemplary, and that other conditions may be used in addition to (or in place of) the above-listed conditions As previously described, in some embodiments, the on-skin unit may include the sensor electronics unit, which provides systems and methods for processing sensor data. The sensor electronics unit generally includes hardware, firmware, and/or software that enable measurement of levels of the analyte via the sensor and that enable audible, tactile, or visible communication or display of the sensor data. Accordingly, the sensor electronics unit enables processing of and displaying of sensor data. For example, the sensor electronics unit may include programming for retrospectively and/or prospectively initiating a calibration, converting sensor data, updating the calibration, and/or evaluating the calibration for the analyte sensor.

The sensor electronics unit can be affixed to a printed circuit board (PCB), or the like, and can take a variety of forms. For example, the sensor electronics unit can take the form of an integrated circuit (IC), such as an Application-Specific Integrated Circuit (ASIC), a microcontroller, or a processor, such as described in more detail herein with reference to sensor electronics unit and/or remote computer system. In some embodiments, the sensor electronics unit comprises a digital filter, for example, an IIR or FIR filter, configured to smooth the raw data stream from the A/D converter.

In an embodiment wherein the sensor electronics unit is at least partially removably attached to the on-skin unit, a system can be provided to enable docking of the sensor electronics unit, and thereby downloading and viewing of the sensor data on a remote device, e.g., a sensor receiver, PDA, computer system, docking station, insulin pump, a hearing aid, or the like. In one such embodiment, the on-skin unit provides numerical sensor information; additionally, a user can dock the removable sensor electronics unit of the on-skin unit onto the remote device to view additional information (e.g., graphical sensor information). Alternatively, the on-skin unit can be used instead of the remote computer system to store and process all of the necessary data until a remote computer system is available for the transfer of data (or enable a system that does not require a remote computer system). In some alternative embodiments, the on-skin unit communicates with the remote computer system via a cable, radio frequency, optical, inductive coupling, infrared, microwave or other known methods of data transmission. In one such exemplary embodiment, the on-skin unit is configured to communicate with the remote computer system when "requested" or interrogated by the remote computer system. For example, when the remote computer system is held in close proximity (e.g., within 3 meters) of the on-skin unit, transmission of sensor data can be requested (e.g., using data transmission methods such as inductive coupling, optical, infrared, or the like.)

An on-skin unit with data communication directly therefrom can provide improved convenience to the patient (e.g., there is no need for the patient to keep track of the remote computer system and maintain it within a predetermined range of the sensor at all times) and increased ease of use (e.g., fewer parts for the patient to understand, program, and/or carry). Additionally, circumstances exist (e.g., on airplanes, while swimming, etc.) where a patient may not be able to carry a remote computer system or during which time certain wireless transmissions may not be permitted; however, with an on-skin user-communicating unit, the patient will not be without critical sensor data.

FIG. 10A is a perspective view of one embodiment of a sensor system which includes a mounting unit in the form of a disposable thin laminate sensor housing. The laminate sensor housing 1000 includes an adhesive layer 1008 and a plurality of layers (see FIG. 10B) beneath housing cover 1054. The sensor housing 1000 is adhered to the skin by the adhesive layer 1008, which is described in more detail elsewhere herein. The laminate housing may be formed from a plurality of thin layers secured together to form an overall thin housing.

In some embodiments, the overall height of the laminate housing is no more than about 0.5 inches in its smallest dimension, or no more than about 0.25 inches in its smallest dimension, or no more than about 0.125 inches in its smallest dimension. In some embodiments, the overall height of the laminate housing is from about 0.075 inches or less, 0.08 inches or less, 0.09 inches or less, 0.1 inches or less, or 0.125 inches or less to about 0.15 inches or more, 0.2 inches or more, 0.225 inches or more, or 0.25 inches or more; while the length and/or width of the laminate housing can be substantially greater, for example, at least about 0.25 inches or more, 0.5 inches or more, 1 inch or more or 1.5 inches or more. In some embodiments, the aspect ratio of the laminate housing is at least about 10:1, 15:1, 20:1, 30:1, 40:1, or 50:1.

FIG. 10B is cut-away side cross-sectional view of the thin, laminate, flexible sensor system in one embodiment. As shown, the layers are secured together, and the sensor body and sensor electronics unit are electrically connected. Although a particular order of layers is illustrated in FIG. 10B, in other embodiments, the layers can be repositioned relative to one another, integrated with one another, and/or otherwise modified while still enabling sensor function and performance.

In some embodiments, the sensor device includes a sensor body 1020 configured to continuously measure an analyte concentration in a host and a sensor housing 1000 configured to receive the sensor body. The sensor body 1020 is inserted into the host's subcutaneous tissue by press insertion as described in more detail elsewhere herein. The sensor housing 1000 may be adapted for placement adjacent to the host's skin and includes multiple layers (e.g., a laminate housing) including one or more of the following functional components: electronics operatively connected to the sensor body 1020 and including a processor module configured to provide a signal associated with the analyte concentration in the host, a power source configured to power at least one of the sensor body and the electronics, an antenna configured for radiating or receiving an RF transmission, and an adhesive layer configured to adhere the housing to the host's skin. In some embodiments, the sensor housing 1000 is a substantially planar, flexible, laminate housing.

In some embodiments, the sensor housing includes a power source associated with (e.g., located in or on) a substantially planar, flexible substrate. In some embodiments, the laminate sensor housing 1000 includes a flexible battery 1044, which provides a source of power for the sensor body and/or electronics, as described in more detail elsewhere herein. Although the battery 1044 is shown as a layer adjacent to the adhesive layer in the illustrated exemplary embodiment, the flexible battery can be disposed in the adhesive layer and/or laminated to the adhesive layer, including a configuration wherein other layers are located between the flexible battery and the adhesive layer. In some embodiments, the flexible battery is no more than about 0.2, 0.1, 0.05, 0.03, 0.02, or 0.01 inches in its smallest dimension. In some embodiments, the flexible battery is a thin, flexible battery and has an aspect ratio of at least about 10:1. In some alternative embodiments, the flexible battery is shaped to conform to at least a part of the housing cover. In some embodiments, the battery is formed in a spiral configuration. In some embodiments, the battery is combined into another functional layer of the laminate housing; for example, it may not be a distinct layer, per se.

In some embodiments, the laminate sensor housing 1000 includes a conductive contact layer 1028, which provides an electrical connection between the sensor body 1020 and sensor electronics (e.g., electrical contacts on the flexible circuit board 1050). In some embodiments, the conductive contact layer 1028 forms at least a portion of the electronics or electronics component. In some embodiments, the conductive contact layer includes one or more discrete electrical contacts configured to electrically connect one or more electrodes of the sensor body to the sensor electronics (e.g., deposited thereon, provided individually as described elsewhere herein, or the like).

Although the illustrated embodiments show the conductive contact layer located between the battery and the flexible circuit board, the conductive contact layer can be located in any location that allows the layer to function as an electrical connector, including as an integral part of the flexible circuit board (e.g., wherein the conductive contact layer is a not distinct layer, per se).

In some embodiments, the conductive contact layer 1028 includes a conductive material that only conducts in the z-axis. In one exemplary embodiment, the conductive material is a z-axis conductive film used to electrically connect the sensor body to the sensor electronics and includes an anisotropic conductor material, for example, a film including anisotropic electrical conductivity, i.e., z-axis conductivity, with little or no conductivity in the other directions. In this exemplary embodiment, discrete electrical contacts are not required, and instead, a piece of this anisotropic conductor material to conduct multiple isolated signals (e.g., for each electrode) is provided.

One example of a suitable Z-axis conductive film useful in accordance with the some embodiments is a synthetic resin membrane having nanometer-sized pores extending through the film from one membrane surface to the other surface and having at least some of its pores filled with a conductive material or composition, such as gold or other metals, or with one or more nonmetallic conductive materials. The Z-axis conductive film may have a thickness of from about 0.0002 or less, 0.0003 inches, 0.0004 inches, or 0.0005 inches to about 0.001 inches, 0.0025 inches, 0.005 inches, or 0.01 inches or more. The dimensions of the film and the metal fibrils provide good performance at 50 GHz and higher frequencies. U.S. Pat. No. 5,805,426 describes some z-axis conductive films suitable for use in certain embodiments.

Another example of suitable z-axis electrical conductor films that can be formed as adhesive and/or in standalone forms and can be made from nickel particles (e.g., one per conduction path) and a polymer matrix (e.g., polyvinylidene fluoride for the standalone film and epoxy for the adhesive film), such as described in (see, e.g., Yunsheng Xu and D. D. L. Chung, *Journal of Electronic Materials*, Volume 28, Number 11, pp. 1307-1313 (1999)).

In some embodiments, the sensor electronics are located on a substantially planar, flexible substrate. In some embodiments, the laminate sensor housing includes a flexible circuit board, such as described in more detail elsewhere herein, on which at least a portion of the sensor electronics are located. The flexible circuit board is at least one of disposed in the adhesive layer, disposed on the adhesive layer, and laminated to the adhesive layer, however other configurations are possible. In some embodiments, the flexible circuit board may be no more than about 0.2, 0.1, 0.05, 0.04, 0.03, 0.02 or 0.01 inches in its smallest dimension. In some embodiments, the flexible circuit board is combined into another functional layer of the laminate housing; for example, it may not be a distinct layer, per se.

In some embodiments, the laminate sensor housing includes a housing cover 1054 configured to assist in and/or provide at least one of water resistant, waterproof, and/or hermetically sealed properties to the sensor housing; however, other portions (e.g., layers) of the laminate housing can additionally include configurations and arrangements that provide water resistant, waterproof, and/or hermetically sealed properties. Additionally or alternatively, the housing cover is configured to provide mechanical and/or adhesive force for layers of the laminate housing. Additionally or alternatively, the housing cover includes an overcover-type bandage configured to cover some or all portions of the sensor housing and/or adhesive of the device.

In some embodiments, the sensor housing includes an antenna configured for radiating or receiving an RF transmission, wherein the antenna is located on a substantially planar, flexible substrate. In some embodiments, an antenna is at least one of disposed in the adhesive layer, disposed on the adhesive layer, and laminated to the adhesive layer, however other configurations are possible. For example, the antenna can be located within any layer of the laminate sensor housing. Alternatively, the sensor body can be configured to communicate with another device (e.g., a receiver) using other communications systems and methods, including but not limited to wired connectivity, IR, and the like. While not wishing to be bound by theory, it is believed that a disposable thin laminate sensor housing as described herein can reduce or eliminate motion artifact caused by external influences (e.g., bumping or other movement of the sensor housing), which in conventional sensor systems (e.g., having sensor housing with lower aspect ratios and/or greater thicknesses) is translated to the sensor body in vivo, causing motion artifact on the sensor signal. Accordingly, a more stable signal with overall improved patient comfort can be achieved with a thin laminate sensor housing as described herein.

Sensor Electronics Unit

Figure 11:
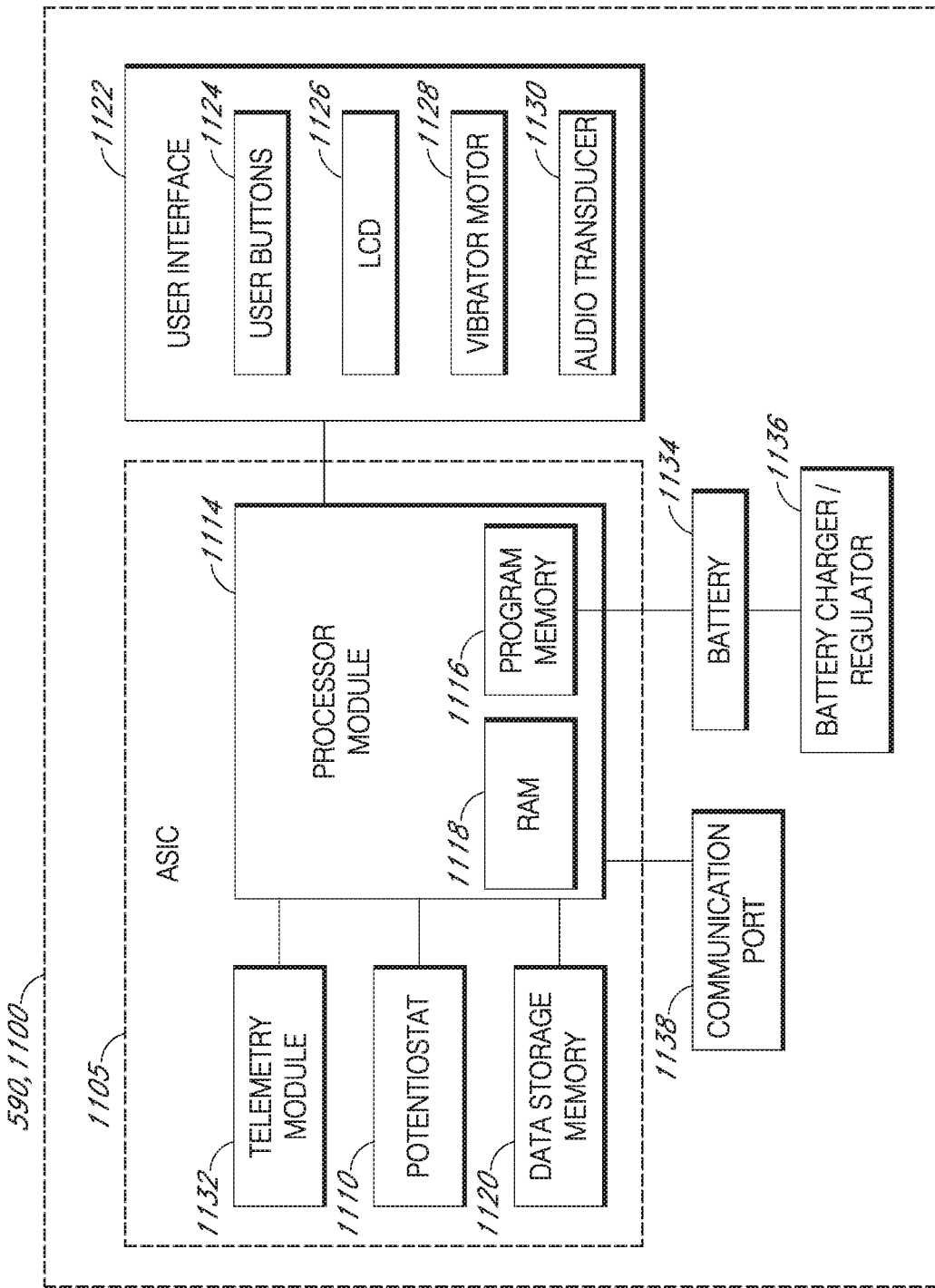
FIG. 11 illustrates a block diagram associated with one embodiment of the sensor electronics unit.

FIG. 11 is a block diagram illustrating one embodiment of the sensor electronics unit 590, 1100. In this embodiment, the ASIC 1005 is coupled to a communication port 1138 and a battery 1134. Although the illustrated embodiment includes an Application Specific Integrated Circuit (ASIC) 1105 that includes much of the electronic circuitry, in other embodiments, the ASIC 1105 is replaced with one or more of any suitable logic device, such as, for example, field programmable gate arrays (FPGA), microprocessors, analog circuitry, or other digital or analog circuitry.

In the embodiment shown in FIG. 11, a potentiostat 1110 is coupled to an analyte sensor in order to receive sensor data from the analyte sensor. Any of a variety of mechanisms can be used to couple the potentiostat 1110 to the analyte sensor. For example, in one embodiment, the one or more ends of the working electrode(s) is exposed to provide electrical connection between the potentiostat and the first and second sensor elements. In one embodiment, the potentiostat 1110 provides a voltage to the analyte sensor in order to bias the sensor to enable measurement of a current value indicative of the analyte concentration in the host (also referred to as the analog portion). The potentiostat can have one channel or multiple channels, depending on the number of working electrodes, for example. In some embodiments, the potentiostat 1110 includes a resistor (not shown) that translates the current into voltage. In some embodiments, a current to frequency converter is provided that is configured to continuously integrate the measured current, for example, using a charge counting device. In some embodiments, an A/D converter digitizes the analog signal into "counts" for processing. Accordingly, the resulting raw data stream in counts is directly related to the current measured by the potentiostat 1110.

A processor module 1114 is the central control unit that controls the processing of the sensor electronics unit. In some embodiments, the processor module 1114 is formed as part of a custom chip, such as an ASIC, however a computer system other than an ASIC can be used to process data as described herein, for example a microprocessor can be used for some or all of the sensor electronics module processing. The processor module 1114 typically provides a program memory 1116, which provides semi-permanent storage of data, for example, storing data such as sensor identifier (ID) and programming to process data streams (for example, filtering, calibration, fail-safe checking, and the like). The processor additionally can be used for the system's cache memory, for example for temporarily storing recent sensor data. In some embodiments, the processor module comprises memory storage components such as ROM, RAM, dynamic-RAM, static-RAM, non-static RAM, EEPROM, rewritable ROMs, flash memory, and the like. In one exemplary embodiment, RAM 1118 can be used for the system's cache memory, for example for temporarily storing recent sensor data.

In some embodiments, the processor module 1114 comprises a digital filter, for example, an IIR or FIR filter, configured to smooth the raw data stream from the A/D converter. Generally, digital filters are programmed to filter data sampled at a predetermined time interval (also referred to as a sample rate). In some embodiments, such as when the potentiostat 1110 is configured to measure the analyte at discrete time intervals, these time intervals determine the sample rate of the digital filter. In some alternative embodiments, wherein the potentiostat 1110 is configured to continuously measure the analyte, for example, using a current-to-frequency converter, the processor module 1114 can be programmed to request a digital value from the integrator at a predetermined time interval, also referred to as the acquisition time. In these alternative embodiments, the values obtained by the processor module 1114 are advantageously averaged over the acquisition time due the continuity of the current measurement. Accordingly, the acquisition time determines the sample rate of the digital filter.

In one embodiment, the processor module 1114 is further configured to generate data packages for transmission to one or more display devices. Furthermore, the processor module 1114 generates data packets for transmission to these outside sources, e.g., via telemetry. As discussed above, the data packages can be customizable for each display device, for example, and may include any available data, such as displayable sensor information having customized sensor data or transformed sensor data, sensor/sensor electronics module ID code, raw data, filtered data, calibrated data, rate of change information, trend information, error detection or correction, or the like.

A data storage memory 1120 is operably connected to the processor module 1114 and is configured to store a variety of sensor information. In some embodiments, the data storage memory stores 1, 3, 4, 5, 6, 7, 8, 9, 11, 11, 12, 13, 14, 15, 20, 30 or more days of continuous analyte sensor data. In some embodiments, the data storage memory 1120 stores sensor information such as raw sensor data (one or more raw analyte concentration values), transformed sensor data, or any other displayable sensor information.

In some embodiments, the sensor electronics unit is configured to receive and store contact information in the data storage memory (or program memory), including a phone number or email address for the sensor's host or health care providers for the host (e.g., family member(s), nurse(s), doctor(s), or other health care provider(s)), which enables communication with a contact person (e.g., via phone, pager or text messaging in response to an alarm (e.g., a hypoglycemic alarm that has not been responded to by the host)). In some embodiments, user parameters can be programmed into (or modified in) the data storage memory (or program memory) of the sensor electronics module, via a display device such as a personal computer, personal digital assistant, or the like. User parameters may include contact information, alert/alarms settings (e.g., thresholds, sounds, volume, or the like), calibration information, font size, display preferences, defaults (e.g., screens), or the like. Alternatively, the sensor electronics module can be configured for direct programming of certain user parameters.

In one embodiment, clinical data of a medical practitioner is uploaded to the sensor electronics unit and stored on the data storage memory 1120, for example. Thus, information regarding the host's condition, treatments, medications, etc., can be stored on the sensor electronics unit and can be viewable by the host or other authorized user. In one embodiment, certain of the clinical data are included in a data package that is transmitted to a display device in response to triggering of an alert. The clinical data can be uploaded to the sensor electronics unit via any available communication protocol, such as direct transmission via a wireless Bluetooth, infrared, or RF connection, or via a wired USB connection, for example. Additionally, the clinical data can be uploaded to the sensor electronics unit via indirect transmission, such as via one or more networks (e.g., local area, personal area, or wide area networks, or the Internet) or via a repeater device that receives the clinical data from a device of the medical practitioner and retransmits the clinical data to the sensor electronics module.

Any of a variety of configurations of separate data storage and program memories can be used, including one or multiple memories that provide the necessary storage space to support the sensor electronic data processing and storage requirements. Accordingly, the described location of storage of any particular information or programming is not meant to be limiting, but rather exemplary.

In some embodiments, the sensor electronics unit is configured to perform smoothing or filtering algorithms on the sensor data (e.g., raw data stream or other sensor information), wherein the smoothed or filtered data is stored in the data storage memory as transformed data. Co-pending U.S. Patent Application Publication No. US-2005-0043598-A1, U.S. Patent Application Publication No. US-2007-0032706-A1, U.S. Patent Application Publication No. US-2007-0016381-A1 and U.S. Patent Application Publication No. US-2008-0033254-A1, each of which is incorporated herein by reference in its entirety, describe some algorithms useful in performing data smoothing or filtering herein (including signal artifacts replacement).

In some embodiments, the sensor electronics unit is configured to calibrate the sensor data, and the data storage memory 1120 stores the calibrated sensor data points as transformed sensor data. In some further embodiments, the sensor electronics unit is configured to wirelessly receive calibration information from a display device, from which the sensor electronics module is configured to calibrate the sensor data. U.S. Pat. Nos. 7,310,544 and 6,931,327, each of which is incorporated herein by reference in its entirety, describe some algorithms useful in sensor calibration herein.

In some embodiments, the sensor electronics unit is configured to perform additional algorithmic processing on the sensor data (e.g., raw data stream or other sensor information) and the data storage memory 1120 is configured to store the transformed sensor data or sensor diagnostic information associated with the algorithms. U.S. Pat. Nos. 7,310,544 and 6,931,327, each of which is incorporated herein by reference in it entirety, describe some algorithms that can be processed by the sensor electronics module.

A user interface 1122 can include any of a variety of interfaces, such as one or more buttons 1124, a liquid crystal display (LCD) 1126, a vibrator 1128, an audio transducer (e.g., speaker) 1130, backlight, or the like. A backlight can be provided, for example, to aid the user in reading the LCD in low light conditions. The components that comprise the user interface 1122 provide controls to interact with the user (e.g., the host). One or more buttons 1124 can allow, for example, toggle, menu selection, option selection, status selection, yes/no response to on-screen questions, a "turn off" function (e.g., for an alarm), a "snooze" function (e.g., for an alarm), a reset, or the like. The LCD 1126 can be provided, for example, to provide the user with visual data output. The audio transducer 1130 (e.g., speaker) provides audible signals in response to triggering of certain alerts, such as present or predicted hyper- and hypoglycemic conditions. In some embodiments, audible signals are differentiated by tone, volume, duty cycle, pattern, duration, or the like. In some embodiments, the audible signal is configured to be silenced (e.g., snoozed or turned off) by pressing one or more buttons 1124 on the sensor electronics module or by signaling the sensor electronics module using a button or selection on a display device (e.g., key fob, cell phone, or the like).

In some embodiments, the audio transducer 1130 is mounted to the circuit board or the sensor electronics module housing. In some embodiments, the sound produced by the audio transducer 1130 exits the device from a sound port in the sensor electronics unit, such as a hole on the sensor electronics unit. The hole may be waterproofed or otherwise protected from moisture by a waterproof material that easily allows sound waves there through. In one embodiment, the hole is protected from moisture by an acoustically transparent venting material (wherein the material allows at least about 60%, 70%, 80%, 90%, 95%, or more of the transmitted sound waves therethrough), such as a screw-in vent, a press-fit vent, a snap-in vent, an o-ring vent, and adhesive vent, or the like. One manufacturer that provides acoustically transparent venting material is W. L. Gore & Associates (Elkton, Md.) under the trade name Protective Vents (Acoustic Vents).

The vibrator 1128 can include a motor that provides, for example, tactile signals or alerts for reasons such as described with reference to the audio transducer, above. In one embodiment, the vibrator motor 1128 provides a signal in response to triggering of one or more alerts, which can be triggered by the processor module 1114 that processes algorithms useful in determining whether alert conditions associated with one or more alerts have been met, for example, present or predicted hyper- and hypoglycemic conditions. In some embodiments, one or more different alerts are differentiated by intensity, quantity, pattern, duration, or the like. In some embodiments, the alarm is configured to be silenced (e.g., snoozed or turned off) by pressing one or more buttons 1124 on the sensor electronics unit or by signaling the sensor electronics unit using a button or selection on a display device (e.g., key fob, cell phone, or the like).

In some embodiments, the vibrator motor 1128 is mounted to the circuit board or the sensor electronics housing. The diameter of the motor may be less than or equal to about 6 mm, 5 mm, 4 mm, 3.5 mm, 3 mm, 2.5 mm, or 2 mm. The overall length of the vibrator motor may be less than or equal to about 18 mm, 16 mm, 14 mm, 12 mm, or 10 mm. By providing a low power vibrator motor, the motor can be placed in the sensor electronics unit without significantly affecting the low profile nature of the on-skin sensor electronics unit. In some embodiments, the vibrator motor 1128 is used to provide a vibratory alarm that creates vibration or movement of the sensor within the host.

In another alternative embodiment, the sensor electronics unit is configured to transmit sound waves into the host's body (e.g., abdomen or other body part) that are felt by the host, thereby alerting the host without calling attention to the host, or allowing a hearing-impaired visually-impaired, or tactilely-impaired host to be alerted. In some embodiments, the sound waves are transmitted into the host's body using the electrodes of the sensor itself. In some embodiments, one or more transcutaneous electrodes (other than the electrodes related to analyte measurement) are provided for transmitting sound waves. In some embodiments, electrodes are provided in the adhesive patch that holds the sensor/sensor electronics module onto the host's body, which can be used to transmit the sound waves. In some embodiments, different sound waves are used to transmit different alarm conditions to the host. The sound waves can be differentiated by any sound characteristic, such as but not limited to amplitude, frequency and pattern.

In another alternative embodiment, mild electric shock can be used to transmit one or more alarms to the host. The level of shock delivered may correspond to a level that is not overly uncomfortable to the host; however, the intensity of the level of shock can be configured to increase when a host does not respond to (e.g., snooze or turn off) an alert within an amount of time. In some embodiments, the shock is delivered to the host's body using the electrodes of the sensor itself. In some embodiments, the sensor device includes one or more additional electrodes configured for delivering the shock to the host (alone or in combination with the electrodes related to analyte measurement). In still another example, the one or more electrodes are disposed on the host's skin, such as in the adhesive patch, for delivering the shock. Alternatively, one or more additional patches, each including an electrode, are provided, for delivering the shock. The additional patches can be in wired or wireless communication with the sensor electronics module.

A telemetry module 1132 is operably connected to the processor module 1114 and provides the hardware, firmware, and/or software that enable wireless communication between the sensor electronics unit and one or more display devices. A variety of wireless communication technologies that can be implemented in the telemetry module 1132 include radio frequency (RF), infrared (IR), Bluetooth, spread spectrum communication, frequency hopping communication, ZigBee, IEEE 802.11/802.16, wireless (e.g., cellular) telecommunication, paging network communication, magnetic induction, satellite data communication, GPRS, ANT, or the like. In one embodiment, the telemetry module comprises a Bluetooth chip. In some embodiments, Bluetooth technology is implemented in a combination of the telemetry module 1132 and the processor module 1114.

A battery 1134 is operatively connected to the processor module 1114 (and possibly other components of the sensor electronics unit) and provides the necessary power for the sensor electronics unit. In one embodiment, the battery is a Lithium Manganese Dioxide battery, however any appropriately sized and powered battery can be used (e.g., AAA, Nickel-cadmium, Zinc-carbon, Alkaline, Lithium, Nickel-metal hydride, Lithium-ion, Zinc-air, Zinc-mercury oxide, Silver-zinc, or hermetically-sealed). In some embodiments the battery is rechargeable. In some embodiments, a plurality of batteries is used to power the system.

A battery charger or regulator 1136 can be configured to receive energy from an internal or external charger. In one embodiment, a battery regulator (or balancer) 1136 regulates the recharging process by bleeding off excess charge current to allow all cells or batteries in the sensor electronics module to be fully charged without overcharging other cells or batteries. In some embodiments, the battery 1134 (or batteries) is configured to be charged via an inductive or wireless charging pad. Any of a variety of known methods of charging batteries can be employed, which can be implemented with the system described herein, including wired (cable/plug) and wireless methods.

One or more communication ports 1138, also referred to as external connector(s), can be provided to allow communication with other devices, for example a PC communication (com) port can be provided to enable communication with systems that are separate from, or integral with, the sensor electronics module. The communication port, for example, can comprise a serial (e.g., universal serial bus or "USB") communication port, allows for communicating with another computer system (e.g., PC, personal digital assistant or "PDA", server, or the like). In one exemplary embodiment, the sensor electronics unit is able to transmit historical data to a PC or other computing device for retrospective analysis by a patient or physician.

In some continuous analyte sensor systems, the processor module of the sensor electronics unit and/or another computer system is configured to execute prospective algorithms used to generate transformed sensor data or displayable sensor information, including, for example, algorithms that: evaluate a clinical acceptability of reference or sensor data, evaluate calibration data for best calibration based on inclusion criteria, evaluate a quality of the calibration, compare estimated analyte values with time corresponding measured analyte values, analyze a variation of estimated analyte values, evaluate a stability of the sensor or sensor data, detect signal artifacts (noise), replace signal artifacts, determine a rate of change or trend of the sensor data, perform dynamic and intelligent analyte value estimation, perform diagnostics on the sensor or sensor data, set modes of operation, evaluate the data for aberrancies, or the like, which are described in more detail in U.S. Pat. Nos. 7,310,544, 6,931,327, U.S. Patent Application Publication No. US-2005-0043598-A1, U.S. Patent Application Publication No. US-2007-0032706-A1, U.S. Patent Application Publication No. US-2007-0016381-A1, U.S. Patent Application Publication No. US-2008-0033254-A1, U.S. Patent Application Publication No. US-2005-0203360-A1, U.S. Patent Application Publication No. US-2005-0154271-A1, U.S. Patent Application Publication No. US-2005-0192557-A1, U.S. Patent Application Publication No. US-2006-0222566-A1, U.S. Patent Application Publication No. US-2007-0203966-A1 and U.S. Patent Application Publication No. US-2007-0208245-A1, each of which is incorporated by reference herein in its entirety. Furthermore, the sensor electronics unit can be configured to store the transformed sensor data (e.g., values, trend information) and to communicate the displayable sensor information to a plurality of different display devices. In some embodiments, the display devices are "dummy" devices, namely, they are configured to display the displayable sensor information as received from the sensor electronics unit, without any additional sensor data processing.

Figure 5D:
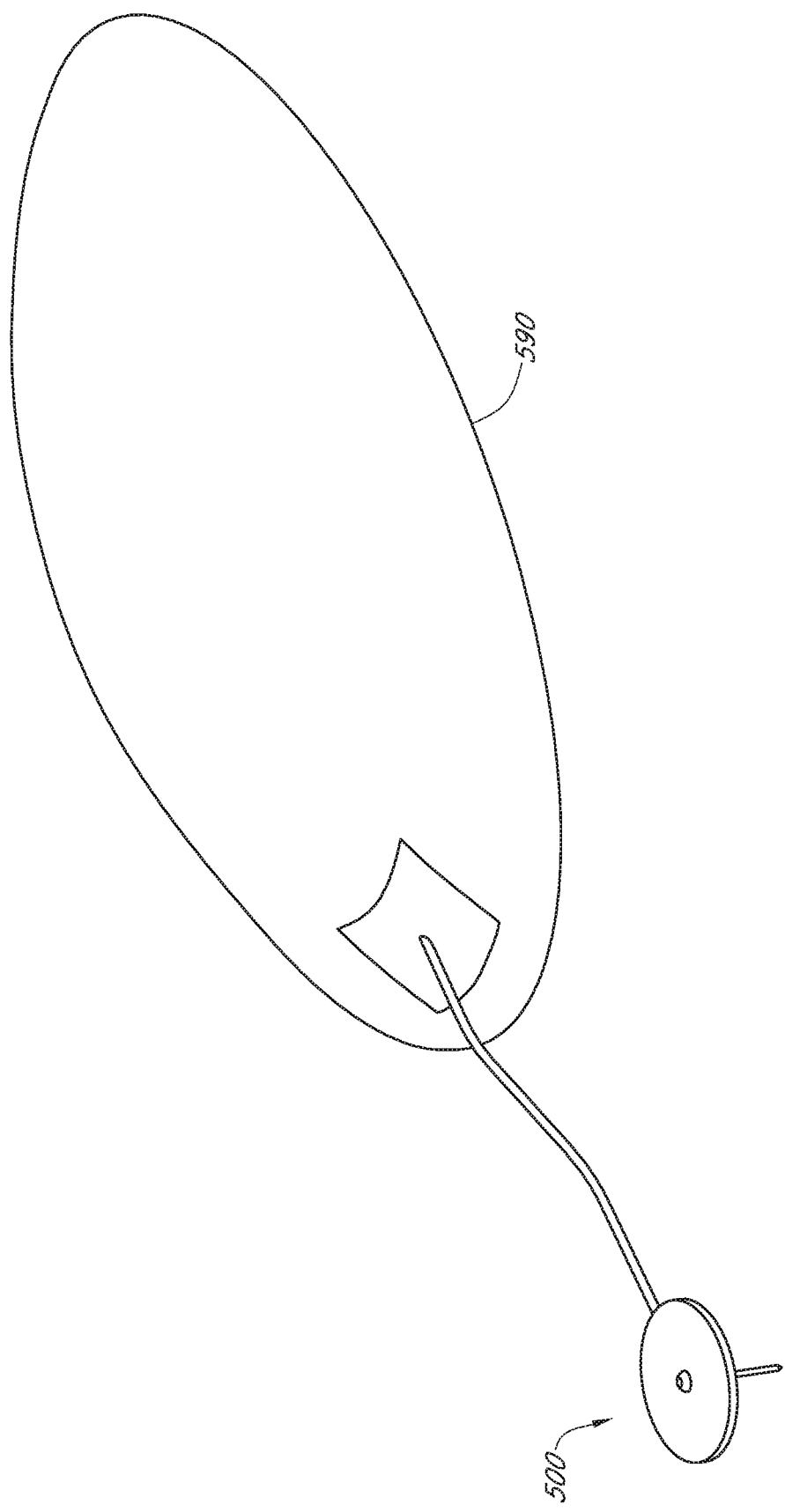
FIG. 5D illustrates a perspective view of still another embodiment of the sensor device that is connected to the sensor electronics unit via a tether.
Figure 5E:
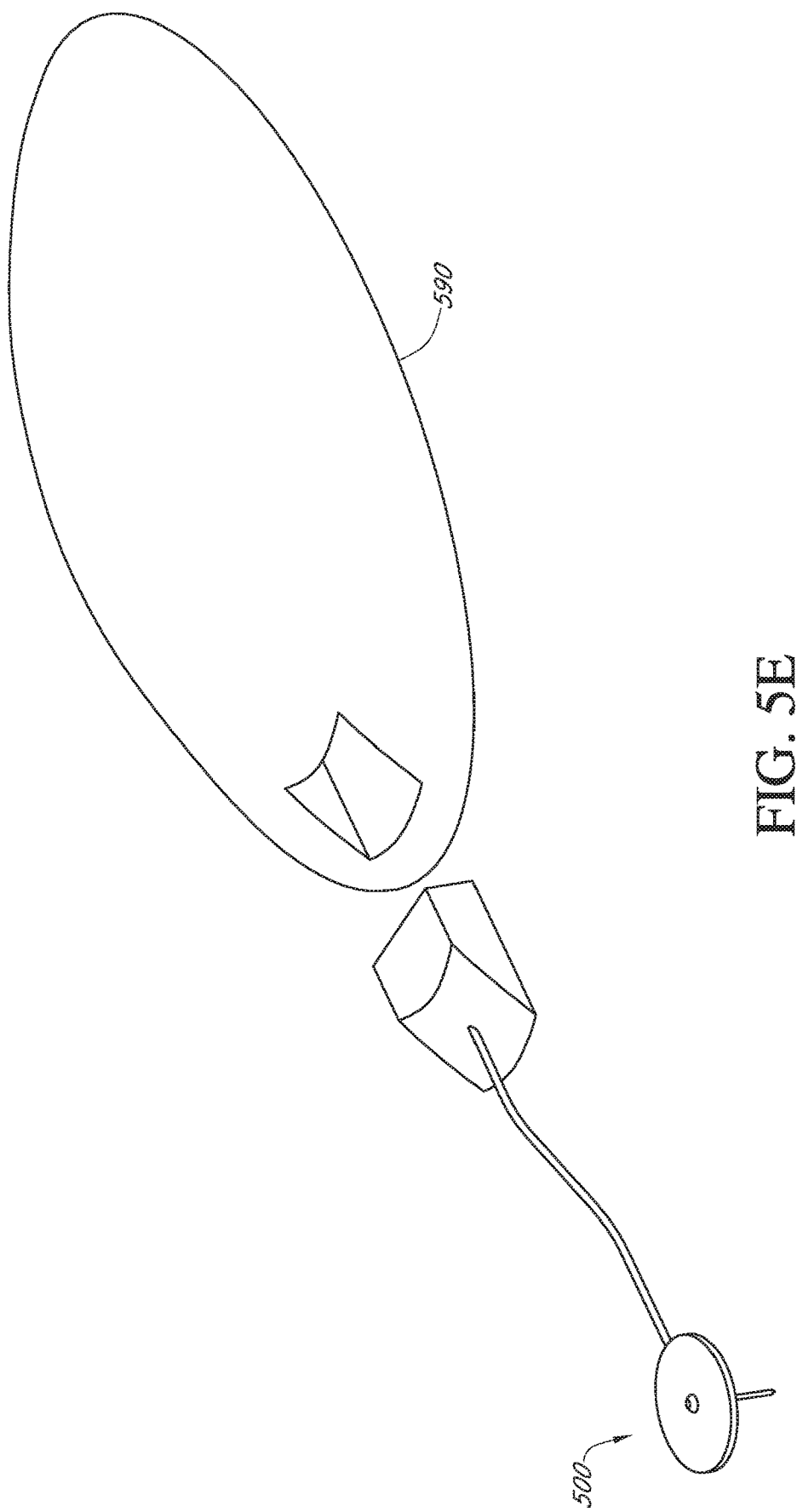
FIG. 5E illustrates a perspective view of the embodiment of FIG. 5D disconnected from the sensor electronics unit.

As described elsewhere herein, in some embodiments, the sensor device may comprise a sensor electronics unit that is united with the mounting unit. Alternatively, as illustrated in FIGS. 5D and 5E, the sensor electronics unit 590 may be detachably connected to the mounting unit of the sensor device 500 via a tethered connection to enable the host to remove the sensor electronics unit 590 during activities such as showering, swimming, or exercising. The tethered configuration may be desirable in some instances because it isolates any movement, pressure, and other artifacts associated with the sensor electronics unit 590 from the sensor device 500. Accordingly, with a tethered configuration, the risk any of the aforementioned artifacts being translated to the electrode is reduced (or eliminated), as compared to what may occur if the sensor electronics unit was directly connected to the electrodes. As illustrated in FIG. 5F, in some embodiments, a plurality of sensor devices 502, 504 may be connected to the sensor electronics unit 590. In further embodiments, one or more of the sensor device may each be associated with a working electrode, and another sensor device may be associated with a reference electrode. Alternatively, each of the plurality of sensor devices may each comprise a working and reference electrode.

Figure 12:
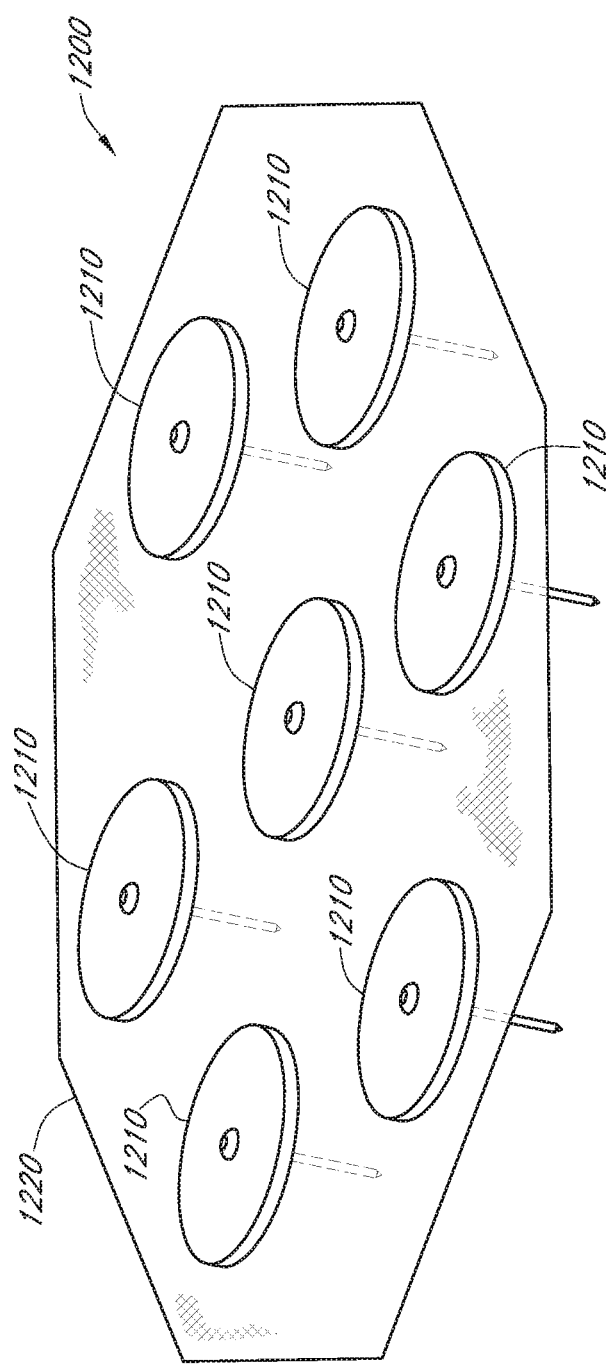
FIG. 12 illustrates one embodiment of a sensor system in which a plurality of sensor devices are grouped together to form a sensor array.

FIG. 12 illustrates another embodiment of a sensor system comprising a plurality of sensor devices. Unlike the embodiment illustrated in FIG. 5F, in this particular embodiment, the individual sensor devices 1210 are each attached to a laminate 1220 that may comprise sensor electronics, and are thereby grouped together to form a sensor array 1200. Alternatively or additionally, the laminate 1220 may comprise a transmitter configured to transmit sensor data to a remote computer system. Transmission of sensor data to a remote computer system can be performed wirelessly or alternatively via a tether that provides electrical connection between the sensor and the sensor electronics unit. The laminate 1220 may comprise a plurality of layers, including an adhesive layer for adhering the laminate to the skin. In certain embodiments, the laminate 1220 and the sensor array 1200 may be disposable and configured for single use. The top surface of the laminate 1220 may be provided with markings located on top of the plurality of sensor devices 1210, so that a user can see where pressure should be applied to insert the sensor devices 1210 through the skin. Additional details of the laminate are described elsewhere herein and include description corresponding to the laminate shown in FIGS. 10A and 10B.

In some embodiments, the plurality of sensor devices 1210 are configured to be substantially equivalent and can collectively provide an ability to carry out parallel measurements in a certain region of the host's tissue. Parallel measurements provide redundancy and can increase the accuracy and reliability of the overall measurement, as the plurality of measurements can be processed (e.g., by averaging the plurality of measurements and/or by eliminating outlier measurements that deviate from the average by a predetermined value).

In other embodiments, the sensor devices of the sensor array may differ in a variety of characteristics, other than a difference in the insertion site. For example, some of the sensor devices of the array may be tuned to detect analyte at low analyte concentrations, while other sensor devices of the same array may be tuned to detect analyte at high analyte concentrations. As another example, different sensor devices of the sensor array may be configured to penetrate the skin at different preselected depths and reside in different layers (e.g., the stratum germinativum, dermis, subcutaneous layers) of the skin. In some embodiments, certain sensor devices 1210 may be used to detect different analytes. For example, one or more of the sensor devices 1210 of the array 1200 may be configured to detect glucose, while other sensor devices 1210 may be used to detect lactic acid, uric acid, or other analytes. In some embodiments, the sensor array 1200 is configured to provide physiological information from different localities of the body, for example, information relating to wound healing, lactic acid in muscles, presence of interferents, cardiac monitoring, etc. The information collected from the different sensor devices 1210, in turn, may be processed (e.g., as input in an algorithm to trigger calibration, to update calibration, and/or to validate or reject inaccurate reference analyte values from a reference analyte monitor) to generate an analyte concentration value that can be displayed to the user. Other information that may be collected include those corresponding to parameters that can affect sensor characteristics (e.g., sensor sensitivity or baseline).

In some embodiments, the information collected from the plurality of sensor devices 1210 can be used to provide a basis for determining which of the sensor devices 1210, in the array 1200, is likely to provide a more representative or accurate analyte measurement. For instance, if a certain number of sensor devices 1210 within a locality of the array 1200 provide measurements that are more consistent (e.g., with less standard deviation) with each other than sensor devices 1210 of other localities, this information may be processed such that a higher confidence level is attributed to that particular locality. In turn, averaging of sensor device measurements may take into account this information by according more weight to measurement values from sensor devices 1210 associated with that particular locality than measurements from other sensor devices 1210 associated with other localities.

Alternatively, the plurality of sensor devices 1210 may be used to provide information regarding differences of a certain parameter along a plane of an area covered by the sensor array 1200. The parameter may be related to physiological information, such as analyte concentration, so that an analyte concentration gradient can be measured. In one example, the sensor array 1200 may be configured to detect a build up of lactic acid in a certain locality (e.g. in certain muscles) as a result of exercise. Knowledge of lactic acid levels can allow a person (e.g., an athlete competing in a long distance running event) to determine and set a target pace (e.g., a certain running pace to achieve a goal time). As another example, the parameter may be related to the concentration of a drug, so that the body absorption rate of a drug can be determined.

In certain embodiments, one or more of the sensor devices 1210 may function as a reference electrode and/or one or more of other sensor devices 1210 may function as a counter electrode. In still other embodiments, a portion of the laminate (e.g., a portion contacting the skin) may be used as the reference electrode or counter electrode.

Figure 13A:
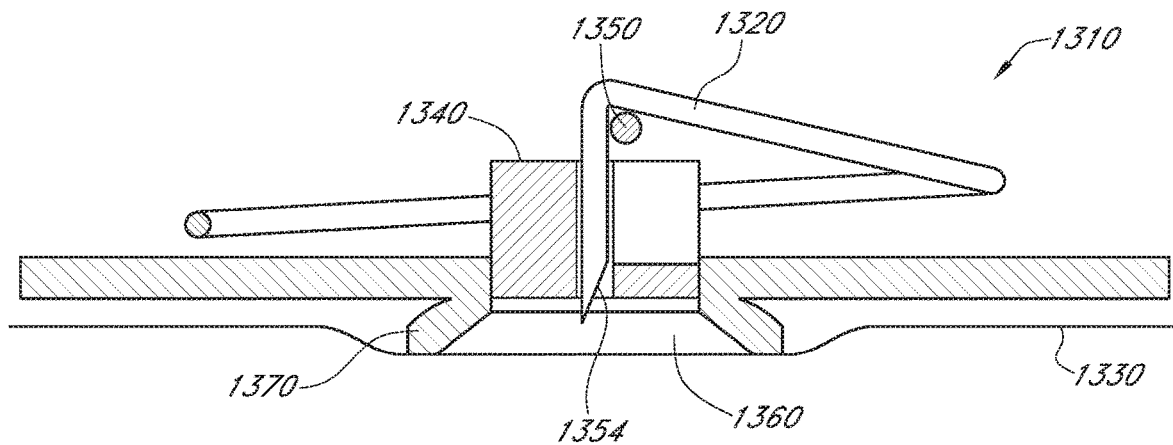
FIGS. 13A and 13B illustrate one embodiment of the sensor device with a skin tensioner.
Figure 13B:
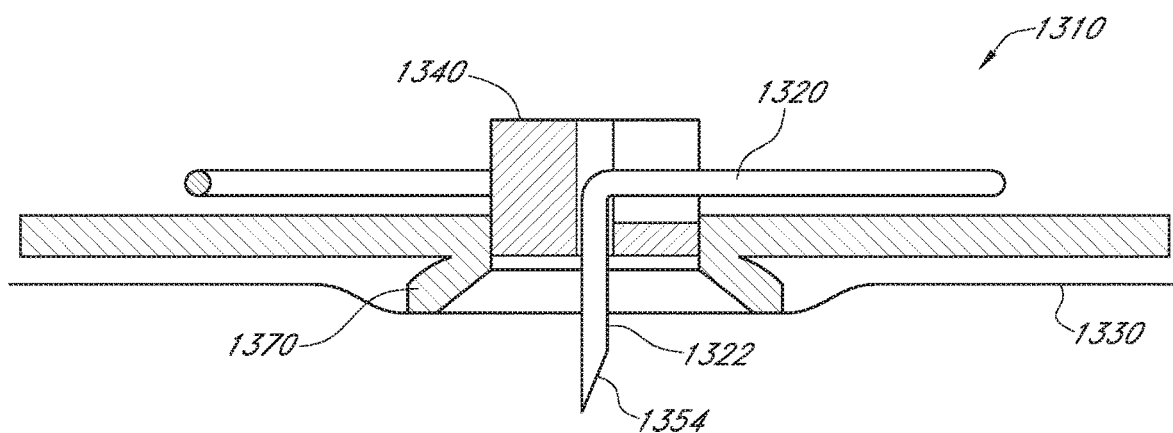

In some embodiments, the sensor device may include a skin tensioner that presses against a skin surface to create tension in the skin surface. FIGS. 13A and 13B illustrate cross-sectional side views one such embodiment, with FIG. 13A representing a tensioned configuration of the sensor device 1310 prior to deployment and FIG. 13B representing a relaxed configuration after deployment. As shown, the sensor device 1310 is equipped with a skin tensioner 1370 that allows the skin surface 1330 to be placed under substantially uniform or even tension across a certain skin area covered by the skin tensioner 1370. Skin tensioning prior to sensor device insertion may result in a more stable insertion with minimal lateral movement of a portion of the senor device that is to be inserted under the skin. In turn, this may further reduce discomfort to the user. In some embodiment, the skin tensioner 1370 may be formed of any of variety of flexible material (e.g., silicone, polyurethane, neoprene) that possesses flexibility and allows it to conform to the contour of the skin surface 1330. In other embodiments, however, the skin tensioner may be formed of a rigid material.

As illustrated in FIGS. 13A and 13B, the skin tensioner 1370 may be formed of a protruding element that is configured to flex outwardly when pressed against the skin surface 1330. Although shown to protrude outwardly at an angle α of about 135 degrees with respect to the lower surface of the sensor device 1310 prior to contact with the skin surface 1330, it is contemplated that the skin tensioner 1370 may protrude at any angle that is greater than 90 degrees and less than 180 degrees with respect to the lower surface of the sensor device 1310. In some embodiments, the angle α may be from 100 degrees to 170 degrees, or from 115 degrees to 155 degrees, or from 125 to 145 degrees. The skin tensioner 1370 may be configured to define an area resembling any of a variety of shapes. In one embodiment, the skin tensioner defines a shape substantially resembling a circle. However, it is contemplated that in other embodiments, the skin tensioner may define a shape that resembles an ellipse, a square, a rectangle, or any other shape that forms an enclosure.

During use, when the sensor device 1310 is placed on the skin surface 1330, a pocket 1360 containing air is formed. As pressure (e.g., by a user) is applied to the sensor device 1310 in a direction toward the skin surface 1330, some of the air in the pocket 1360 escapes, thereby creating a relative negative pressure in the pocket. As a result, the skin tensioner 1370 allows the sensor device 1310 to be more securely held against the skin surface 1330. In further embodiments, the skin tensioner may be equipped with a vacuum mechanism that allows air to be suctioned from the air pocket formed when the skin tensioner 1370 is applied to the skin surface 1330. In one embodiment, the vacuum mechanism may comprise a unidirectional air valve that releases air from the pocket when downward pressure is applied to the sensor device. As air is suctioned out of the pocket 1360, the skin surface 1330 is stretched and may also be pulled upwards toward a piercing needle 1354 of the sensor device 1310.

As illustrated in FIGS. 13A and 13B, the sensor device 1310 comprises a spiral spring 1320, a sensor insertion guide 1340, a retainer 1350, and the above-described skin tensioner 1370. One end of the spiral spring 1320 forms an in vivo portion 1322 configured for insertion under the skin surface 1330. The rest of the sensor device 1310 is configured to remain above the skin surface 1330. The spiral spring 1320 may be formed of a material having a high spring constant. During manufacturing, the spiral spring 1320 is tensioned and the in vivo portion is placed into the sensor insertion guide 1340 to prevent buckling during insertion. The retainer 1350 keeps the sensor 1310 device in the tensioned state, i.e., in a loaded state. During use, after the sensor device 1310 has been affixed to the skin, such that the sensor device 1310 is ready for insertion, the retainer 1350 is removed (e.g., by pulling out a tab). As a result of the tension/spring force, the in vivo portion 1322 of the sensor device 1310 is inserted through the skin surface 1330 via the sensor insertion guide 1340.

Figure 14A:
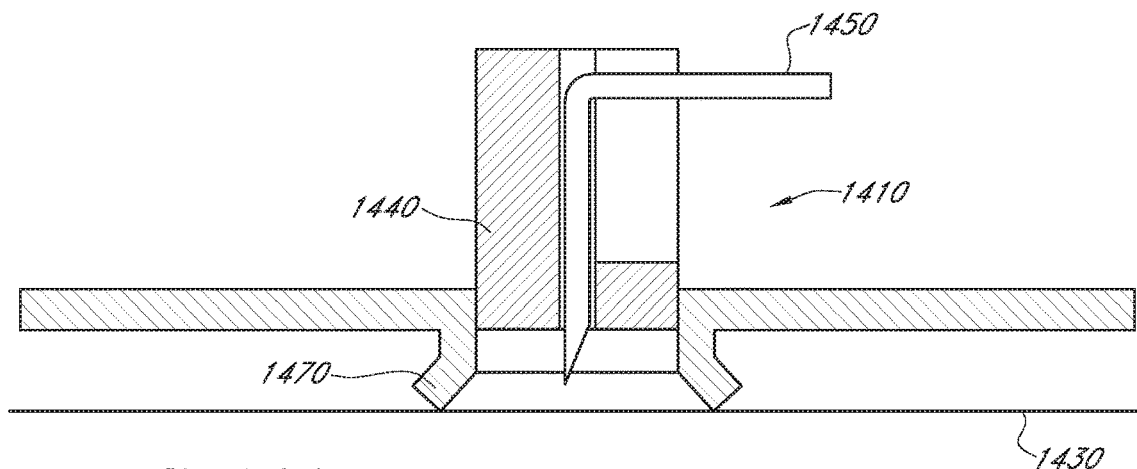
FIGS. 14A, 14B, and 14C illustrate another embodiment of the sensor device with a skin tensioner.
Figure 14B:
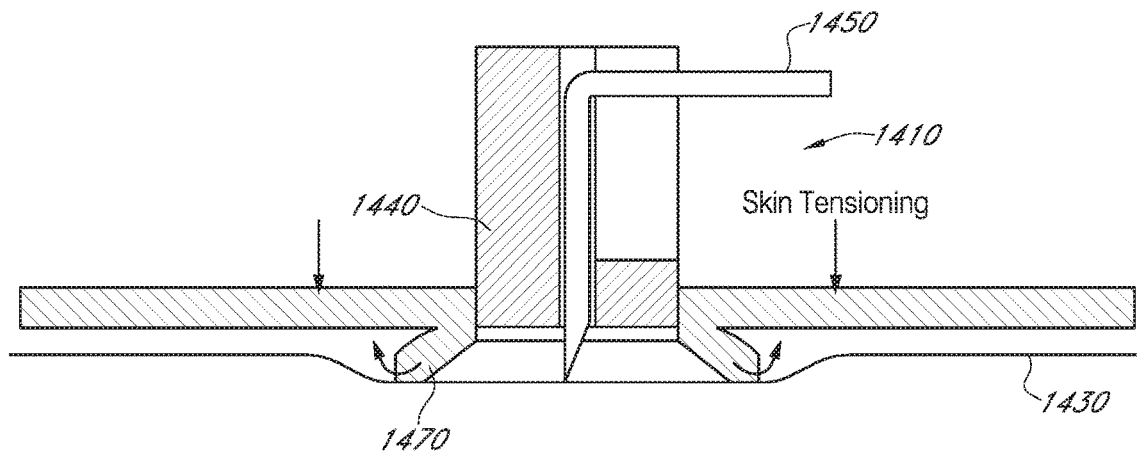
Figure 14C:
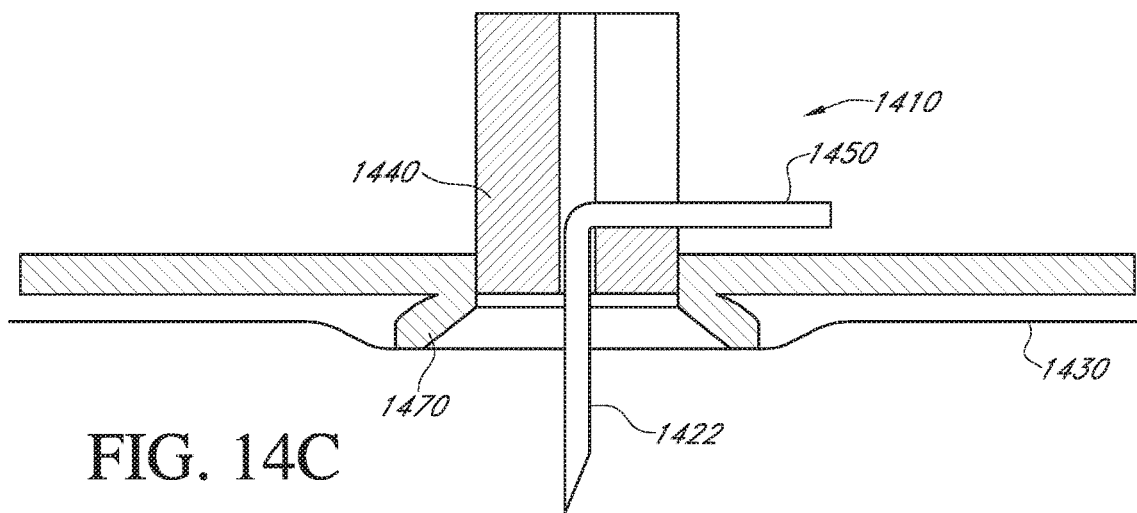

FIGS. 14A, 14B, and 14C illustrate another embodiment of a sensor device 1410 that comprises a skin tensioner 1470. As illustrated in FIG. 14A, the sensor device 1410 also comprises a sensor insertion guide 1440 that accommodates a sensor unit 1450, which comprises an in vivo portion 1422 designed for placement beneath the skin surface 1430. During use, the sensor device 1410 is first affixed to the skin surface 1430, as illustrated in FIG. 14B. Next, the sensor unit 1450 is pushed downwards to cause deployment, as illustrated in FIG. 14C. This can be achieved in any of a variety of ways. For example, in some embodiments, the downward push may originate from action by a user applying pressure directly (e.g., by pushing a button) on the sensor unit 1450. In other embodiments, the downward push may originate from user action in attaching a certain component (e.g., a transmitter, a sensor electronics unit) onto the sensor device 1410.

In some embodiments, the sensor device may incorporate Micro Electro Mechanical Systems (MEMS)-based technology, which allow for miniaturization of devices that are minimally invasive. Using semiconductor manufacturing techniques, MEMS technology permits a high level of functionality to be packaged into a microneedle. Another advantage of employing MEMS technology is that it permits building of the sensor device on a wafer scale, which can reduce the number of steps required during manufacturing.

FIG. 15A depicts one embodiment of a sensor device 1510 built based on MEMS technology. The sensor device 1510 includes a sensor body 1590 that can be formed of a semiconductor material (e.g. silicon). The sensor device 1510 also includes an in vivo portion 1560 that comprises a working electrode 1522, a support member 1530, and a reference electrode 1524. Insulation to prevent an electrical connection between the working electrode 1522 and the reference electrode 1524 can be achieved by thermal oxidation of the silicon to produce a thin layer of oxide on the surface of the sensor body 1590. Additionally or alternatively, an insulating material (e.g., silicon carbide, polyimide) may be deposited onto the sensor body 1590 to provide insulation. The ex vivo portion 1570 of the sensor device 1510 comprises a needle base 1516 that comprises a contact 1558 for providing an electrical connection between the working electrode 1522 and a sensor electronics unit.

The working electrode 1522 comprises a tissue piercing element 1512 which includes a sharp distal tip. The working electrode 1522 may be formed by patterning a thin film layer of conductive material (e.g., platinum) using known microelectronic manufacturing methods (e.g., photolithography, sputtering, and epitaxy). As shown in FIG. 15B, which provides a close-up view of the working electrode 1522, the working electrode 1522 is formed in a recessed portion of the sensor device 1510. The recess permits a membrane (not shown) to be deposited onto working electrode 1522 and also provides membrane protection so that the membrane is not delaminated or damaged during sensor device insertion. The different layers of the membrane may be deposited using any know deposition techniques, such as dipping, spraying, or ink-jet material deposition. In some embodiments, instead of (or in addition to) to employing a recess to provide membrane protection, the membrane may be protected by encapsulating or embedding the working electrode (and the membrane associated therewith) in an organic, biodegradable material, such as carbohydrate, which are will chemically breakdown in a physiological environment. However, it is contemplated that in other embodiments, inorganic materials (e.g., a gold foil) that can be dissolved by application of a small amount of current can be used to seal off and to protect the membrane during sensor device insertion. The reference electrode 1524 can be formed by applying a layer of conductive material, such as a silver-containing material, for example, onto a portion of the sensor device 1510 not electrically connected to the working electrode 1522. Alternatively, the reference electrode can be provided by the application of a conductive material on the back of the sensor device. Although shown in FIG. 15A as being located in the in vivo portion 1560 of the sensor device 1510, in certain embodiments, the reference electrode may exist in an ex vivo portion 1570 of the sensor device 1510, for example, at a location that contacts the skin surface. Although not shown, it is contemplated that in some embodiments, a counter electrode formed of a conductive material (e.g., platinum) may be employed in addition to or in place of the reference electrode 1524.

Figure 16:
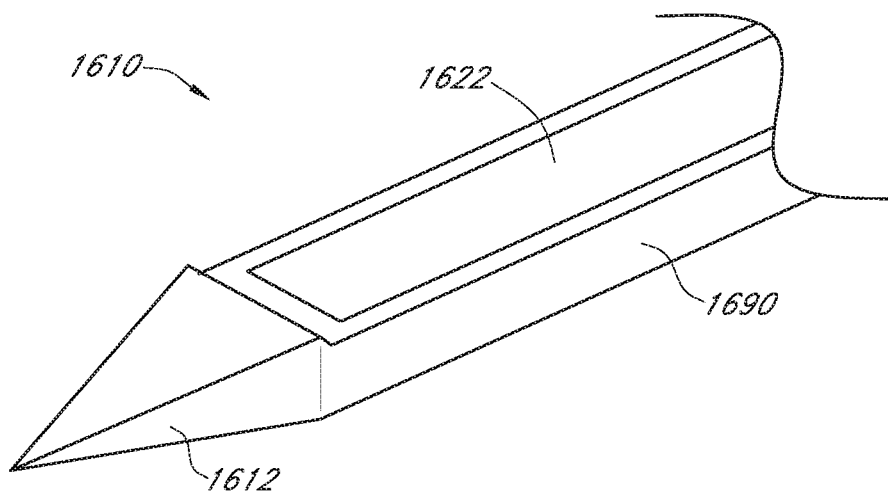
FIG. 16 illustrates still another embodiment of a sensor device built based on MEMS technology.

FIG. 16 illustrates still another embodiment of a sensor device 1610 built based on MEMS technology. In this particular embodiment, the working electrode 1622 is disposed on the sensor body 1690, instead of on a tissue piercing element. As shown, portion of the sensor body 1690 onto which the working electrode 1622 is disposed is recessed with respect to the tissue piercing element 1612 of the sensor device 1610. Thus, a membrane (not shown) that is deposited/formed over the working electrode 1622 can be protected from delamination during the sensor insertion process.

Figure 17A:
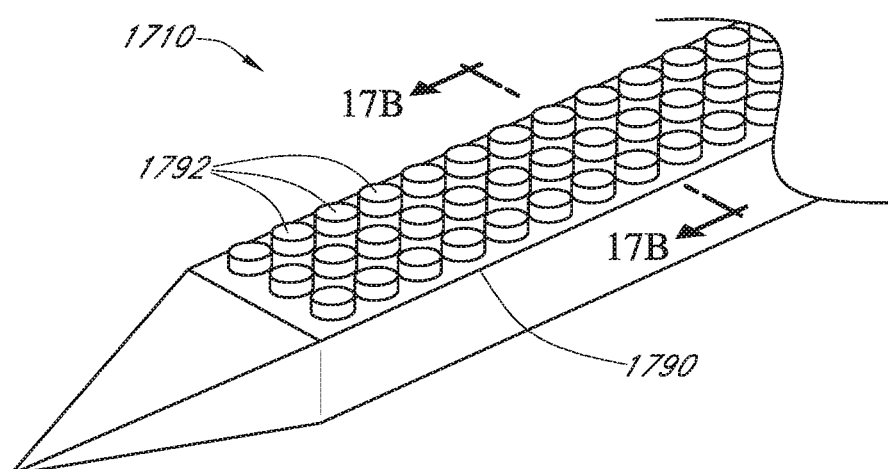
FIGS. 17A and 17B illustrate still another embodiment of a sensor device built based on MEMS technology.
Figure 17B:
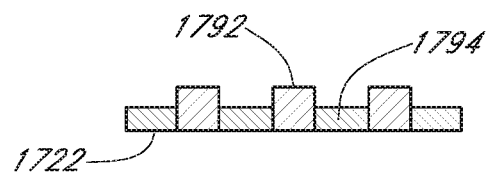

FIG. 17A illustrates still another embodiment of the sensor device 1710 built based on MEMS technology. The embodiment illustrated in FIG. 17A is distinguished from the embodiment illustrated in FIG. 16 in that the sensor body 1790 comprises posts 1792 that project outwardly from the sensor body's 1790 surface, which can form the working electrode 1722 or support a conductive material deposited thereon that forms the working electrode. FIG. 17B is a cross-sectional side view along lines 17B-17B of FIG. 17A. As illustrated in FIG. 17B, the membrane 1794 may be disposed onto the working electrode 1722 and protected by posts 1792 from delamination during the sensor insertion process.

Remote Computer System

In some embodiments, the sensor data can be transmitted wirelessly to a remote computer system. The wireless transmission may be a RF link (e.g. Bluetooth, Wi-Fi, cellular, etc.) between the remote computer system and the sensor electronics and may be one- or two-way. The remote computer system can include any of a variety of devices that facilitates or allows for further processing and/or display of the sensor data, such as for example, a reader that interrogates the sensor electronics to download sensor data, a recorder, a database, a sensor receiver, a personal digital assistant (PDA), an MP3 player, a docking station, a personal computer (PC) or laptop, a work station, an insulin pump, and/or the like. Additionally or alternatively, sensor data can be transmitted to a remote computer system via a wired link such as by a cable (e.g. LAN or USB cable, etc.).

In some embodiments, the remote computer system provides much of the processing and display of the sensor data, and can be selectively worn and/or removed at the host's convenience. Thus, the sensor system can be discreetly worn, and the receiver, which may provide much of the processing and display of the sensor data, can be selectively worn and/or removed at the host's convenience. The remote computer system may include programming for retrospectively and/or prospectively initiating a calibration, converting sensor data, updating the calibration, evaluating received reference and sensor data, and evaluating the calibration for the analyte sensor, such as described in greater detail with reference to U.S. Patent Publication No. US-2005-0027463-A1, which is incorporated herein by reference in its entirety.

Methods of Manufacture

The embodiments of the sensor device described herein may be manufactured using any of a variety of processes. In some embodiments, the sensor unit, which may comprise the sensor, the tissue piercing element, and/or the support member, may be formed of a unitary piece, e.g., formed from a wire, a planar substrate, or any other types of elongated bodies. An etching process can be used to remove certain portions of the elongated body to create electroactive surfaces thereon, thereby forming recessed regions or window regions/surfaces corresponding to working electrodes. The etching process may comprise any of a variety of techniques, such as chemical etching, laser ablation, grit blasting, or other similar techniques. In some embodiments, portions of the elongated body can be masked prior to the etching process to define the boundaries of the electroactive surfaces. After the etching process, a membrane comprising an enzyme can be deposited onto the elongated body using any of a variety of other types of coating processes, such as a dip coating, spray coating, or vapor deposition, for example. Thereafter, the elongated body may be cleaned and cut for singulation into individual sensor units. Any of a variety of known cutting mechanisms, such as a hydraulic cutting device, for example, can be used for the singulation process. In certain embodiments, the elongated body can undergo a surface treatment process (e.g., plasma treatment). After the singulation process, the sensor units may undergo further processing to sharpen the distal end of the tip of the tissue piercing element and to join other components of the sensor device (e.g., mounting unit, the sensor electronics unit, electrical contacts). It should be understood that the process described above is merely exemplary, and some steps may be omitted or replaced by other steps. For example, although the process described above can be carried out by employing a reel-to-reel continuous process, other continuous processes or a batch process may also be used. As another example, although in the process described above, the tissue piercing element, the support member, and/or the sensor are formed of a unitary piece and collectively form the sensor unit, in other embodiments, these components may be formed as separate pieces and processed separately. The pieces may then be assembled together to form the sensor unit. It should also be understood that although the steps of the method are described in a particular order, the various steps need not be performed sequentially or in the order described.

Kits

The sensor devices according to the embodiments described herein may optionally be provided to the user as a kit. The kit can comprise one or more sensor devices and sensor electronics units packaged in a suitable container. In some embodiments, the sensor device may be substantially modular and formed of multiple components (e.g., the tissue piercing element, the sensor body, the mounting unit, the sensor electronics unit) that are to be assembled. The kit can also contain an instruction set or user manual with detailed methods of assembling and/or using the kit components.

To the extent publications and patents or patent applications incorporated by reference herein contradict the disclosure contained in the specification, the specification is intended to supersede and/or take precedence over any such contradictory material.

Terms and phrases used in this document, and variations thereof, unless otherwise expressly stated, should be construed as open ended as opposed to limiting. As examples of the foregoing, the term "including" should be read to mean "including, without limitation" or the like; the term "comprising" as used herein is synonymous with "including", "containing", or "characterized by", and is inclusive or open-ended and does not exclude additional, unrecited elements or method steps; the term "example" is used to provide exemplary instances of the item in discussion, not an exhaustive or limiting list thereof; adjectives such as "known", "conventional", "normal", "standard", and terms of similar meaning should not be construed as limiting the item described to a given time period or to an item available as of a given time, but instead should be read to encompass known, normal, or standard technologies that may be available or known now or at any time in the future; and use of terms like "preferred", "desired", or "desirable", and terms of similar meaning should not be understood as implying that certain features are critical, essential, or even important to the structure or function of the invention, but instead as merely intended to highlight alternative or additional features that may or may not be utilized in a particular embodiment of the invention. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should be read as "and/or" unless expressly stated otherwise. In addition, as used in this application, the articles "a" and "an" should be construed as referring to one or more than one (i.e., to at least one) of the grammatical objects of the article. By way of example, "an element" means one element or more than one element.

The presence in some instances of broadening words and phrases such as "one or more", "at least", "but not limited to", or other like phrases should not be read to mean that the narrower case is intended or required in instances where such broadening phrases may be absent.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it should be understood that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A direct-press insertion sensor device for measuring an analyte concentration, the device comprising:
    a sensor comprising
        an in vivo portion of the sensor configured to be inserted through a skin of a host, the in vivo portion comprising
            at least one electrode and a membrane covering at least a portion of the at least one electrode, and
        a tissue piercing element integrally formed at a distal end of the sensor, wherein the tissue piercing element is configured to pierce the skin of a host, wherein the tissue piercing element has a column strength configured to allow insertion of the in vivo portion through the skin without substantial buckling;
    a mounting unit configured to support the sensor device on a surface of the skin of the host, the mounting unit comprising
        an upper portion comprising a flexible material configured to receive direct pressure from a user for insertion of the tissue piercing element of the sensor,
        a lower portion coupled to an adhesive, the adhesive configured to adhere the mounting unit to the host's skin, and
        a guiding portion disposed between the upper portion and the lower portion, the guiding portion configured to guide the in vivo portion of the sensor through the skin of the host,
        a latch member configured to mate with a receiving member,
        wherein the upper portion is configured to remain in a collapsed state after the insertion of the in vivo portion by the latch member mating with the receiving member; and
    a sensor electronics unit operatively and detachably connected to the mounting unit.

2. The sensor device of claim 1, wherein the tissue piercing element is configured to withstand an axial load greater than about 1 Newton without substantial buckling.

3. The sensor device of claim 1, wherein the at least one electrode comprises a working electrode and a reference electrode.

4. The sensor device of claim 1, wherein the sensor electronics unit is configured to be located over a sensor insertion site.

5. The sensor device of claim 1, wherein the upper portion comprises an elastomeric material.

6. The sensor device of claim 1, wherein the in vivo portion has a substantially circular or oval shape.

7. The sensor device of claim 1, wherein the upper portion has a domed shape prior to sensor insertion.

8. The sensor device of claim 1, wherein the direct pressure is from a thumb or finger of a user.

9. The sensor device of claim 1, wherein the mounting unit comprises a self-containing sterile field, wherein prior to sensor insertion the in vivo portion is hidden inside the self-containing sterile field.

* * * * *

UNITED STATES PATENT AND TRADEMARK OFFICE
CERTIFICATE OF CORRECTION

Page 1 of 3

PATENT NO. : 10,667,733 B2
APPLICATION NO. : 14/968643
DATED : June 2, 2020
INVENTOR(S) : Peter C. Simpson It is certified that error appears in the above-identified patent and that said Letters Patent is hereby corrected as shown below:

On the Title Page

On Page 2, Column 2, Item (56), Line 34, under U.S. Patent Documents, delete "2002/1285465" and insert --2002/0128546--.

On Page 2, Column 2, Item (56), Line 35, under U.S. Patent Documents, delete "Bonnecase" and insert --Bonnecaze--.

On Page 2, Column 2, Item (56), Line 37, under U.S. Patent Documents, delete "Hyuzhakov" and insert --Yuzhakov--.

On Page 2, Column 2, Item (56), Line 64, under U.S. Patent Documents, delete "2006/0133934" and insert --2006/0183984--.

On Page 3, Column 2, Item (56), Line 2, under Other Publications, delete "Biosensenors" and insert --Biosensors--.

On Page 3, Column 2, Item (56), Line 6, under Other Publications, delete "A n" and insert --An--.

On Page 3, Column 2, Item (56), Lines 7-8, under Other Publications, delete "Engindeering" and insert --Engineering--.

On Page 3, Column 2, Item (56), Lines 16-17, under Other Publications, delete "Transactions Biomedical" and insert --Transactions on Biomedical--.

On Page 3, Column 2, Item (56), Line 28, under Other Publications, delete "1(2)" and insert --1(2):--.

On Page 4, Column 1, Item (56), Line 25, under Other Publications, delete "eiectroenzymatic" and insert --electroenzymatic--.

Signed and Sealed this
Twenty-ninth Day of September, 2020

Andrei Iancu
*Director of the United States Patent and Trademark Office*

CERTIFICATE OF CORRECTION (continued)
U.S. Pat. No. 10,667,733 B2

On Page 4, Column 1, Item (56), Line 26, under Other Publications, delete "implanted subcutaneous" and insert --implanted in subcutaneous--.

On Page 4, Column 2, Item (56), Line 7, under Other Publications, delete "32)" and insert --32):--.

On Page 4, Column 2, Item (56), Line 11, under Other Publications, delete "electrochemical:" and insert --electrochemical sensors:--.

On Page 4, Column 2, Item (56), Line 23, under Other Publications, delete "5(4)" and insert --5(4):--.

In the Specification

In Column 2, Line 67, delete "body" and insert --body.--.

In Column 3, Line 8, delete "connection" and insert --connection.--.

In Column 6, Line 14, delete "body" and insert --body.--.

In Column 6, Line 23, delete "connection" and insert --connection.--.

In Column 10, Line 43, delete "dehydroxgenase;" and insert --dehydrogenase;--.

In Column 10, Line 49, delete "Kreb's cycle" and insert --Krebs cycle--.

In Column 10, Line 51, delete "carbamezepine," and insert --carbamazepine,--.

In Column 10, Line 56, delete "carbazepine," and insert --carbamazepine,--.

In Column 10, Lines 57-58, delete "andrenostenedione;" and insert --androstenedione;--.

In Column 11, Line 7, delete "diptheria" and insert --diphtheria--.

In Column 11, Line 14, delete "perioxidase;" and insert --peroxidase;--.

In Column 11, Line 28, delete "Giardia duodenalisa," and insert --Giardia duodenalis,--.

In Column 11, Line 36, delete "Trepenoma pallidium," and insert --Treponema pallidum,--.

In Column 11, Line 37, delete "stomatis virus," and insert --stomatitis virus,--.

In Column 11, Line 58, delete "(barbituates," and insert --(barbiturates,--.

In Column 12, Line 14, delete "and or" and insert --and/or--.

In Column 17, Line 31, delete "(poly" and insert --poly--.

CERTIFICATE OF CORRECTION (continued)
U.S. Pat. No. 10,667,733 B2

In Column 17, Line 32, delete "(PAA," and insert --PAA,--.

In Column 25, Line 20, delete "SYNPERONICS" and insert --SYNPERONIC--.

In Column 26, Line 53, delete "gluteraldehyde" and insert --glutaraldehyde--.

In Column 30, Line 2, delete "W-" and insert --XW- --.

In Column 30, Line 3, delete "W-" and insert --XW- --.

In Column 39, Line 12, delete "eugylcemia," and insert --euglycemia,--.

In Column 39, Line 46, delete "conditions" and insert --conditions.--.

In Column 45, Line 57, delete "in it" and insert --in its--.

In Column 50, Line 54, delete "senor" and insert --sensor--.